(12) United States Patent
Ivashchenko et al.

(10) Patent No.: US 8,618,114 B2
(45) Date of Patent: *Dec. 31, 2013

(54) SUBSTITUTED 3-ARYLSULFONYL-PYRAZOLO[1,5-A]PYRIMIDINES, SEROTONIN 5-HT6 RECEPTOR ANTAGONISTS AND METHODS FOR THE PRODUCTION AND USE THEREOF

(76) Inventors: Andrey Alexandrovich Ivashchenko, Moscow (RU); Nikolay Filippovich Savchuk, Rancho Santa Fe, CA (US); Alexander Vasilievich Ivashchenko, Encinitas, CA (US); Yan Lavrovsky, San Diego, CA (US); Oleg Dmitrievich Mitkin, Moscow reg. (RU); Madina Georgievna Kadieva, Moscow reg. (RU)

(*) Notice: Subject to any disclaimer, the term of this patent is extended or adjusted under 35 U.S.C. 154(b) by 0 days.

This patent is subject to a terminal disclaimer.

(21) Appl. No.: 13/122,152

(22) PCT Filed: Oct. 6, 2009

(86) PCT No.: PCT/RU2009/000518
§ 371 (c)(1),
(2), (4) Date: Apr. 20, 2011

(87) PCT Pub. No.: WO2010/041983
PCT Pub. Date: Apr. 15, 2010

(65) Prior Publication Data
US 2011/0178078 A1    Jul. 21, 2011

(30) Foreign Application Priority Data

Oct. 6, 2008  (RU) ................................. 2008139495
Oct. 6, 2008  (RU) ................................. 2008139496
Oct. 14, 2008 (RU) ................................. 2008140599
Oct. 14, 2008 (RU) ................................. 2008140601

(51) Int. Cl.
*A01N 43/90* (2006.01)
*A61K 31/519* (2006.01)
*C07D 487/00* (2006.01)

(52) U.S. Cl.
USPC ........................................ 514/259.3; 544/281

(58) Field of Classification Search
None
See application file for complete search history.

(56) References Cited

U.S. PATENT DOCUMENTS 8,309,559 B2 * 11/2012 Savchuk et al. ............ 514/259.3

FOREIGN PATENT DOCUMENTS

EP  0941994      3/1999
EP  0941944  *  9/1999  ............ C07D 487/04
RU  2369600     10/2009
WO  WO02/072585  9/2002
WO  WO03/057674  7/2003

OTHER PUBLICATIONS

Vippagunta et. al. Advanced Drug Delivery Reviews 48 (2001) 3-26.*
Slivchuk S.R. et al.: A convenient approach to the synthesis of 3-(arylsulfonyl) pyrazol [1,5-a] pyrimidines and their condensed analogs. Ukraine Zhurnal Organichonoi Ta Farmatsevtichnoi Khimii vol. 4, No. 3, 2006, pp. 62-68.
Lister R.G.: The use of a plus-maze to measure anxiety in the mouse. Psychopharmacology vol. 92, 1987, pp. 180-185.
Holenz J.; Pauwels P.J.; Diaz J.L.; Merce R.; Codony X.; Buschmann H.: Medicinal chemistry strategies to 5-HT6 receptor ligands as potential cognitive enhancers and antiobesity agents. Drug Disc. Today. vol. 11, 2006, pp. 283-299.
Gerard C.; Martres M.-P.; Lefevre K.; Miquel M.-C.; Verge D.; Lanfumey L.; Doucet E.; Hamon M.; El Mestikawy S.: Immuno-localisation of serotonin 5-HT6 receptor-like material in the rat central nervous system. Brain Research vol. 746, 1997, pp. 207-219.
Dawson L.A.; Nguyen H.Q.; Li P.: The 5-Ht(6) receptor antagonist SB-271046 selectively enhances excitatory neurotransmission in the rat frontal cortex and hippocampus. Neuropsychopharmacology vol. 25, 2001, pp. 662-668.

(Continued)

*Primary Examiner* — Jeffrey Murray

(57) ABSTRACT

The invention relates to the novel substituted 3-arylsulfonyl-pyrazolo[1,5-a]pyrimidines of the general formula 1, pharmaceutically acceptable salts and/or hydrates thereof, serotonin 5-HT$_6$ receptor antagonists and pharmaceutical compositions, and also to method for prophylaxis and treatment of various diseases of central nervous system at humans and warm-blooded animals pathogenesis of which is associated with serotonin 5-HT$_6$ receptors, in particular, Alzheimer's disease, Parkinson's disease, Huntington's disease, schizophrenia, and other neurodegenerative diseases, cognitive disorders and obesity.
In the general formula 1:

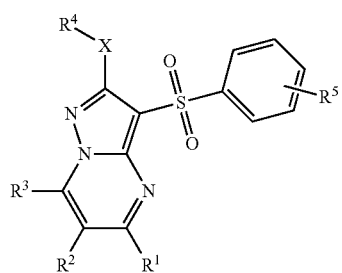

Figure 1:
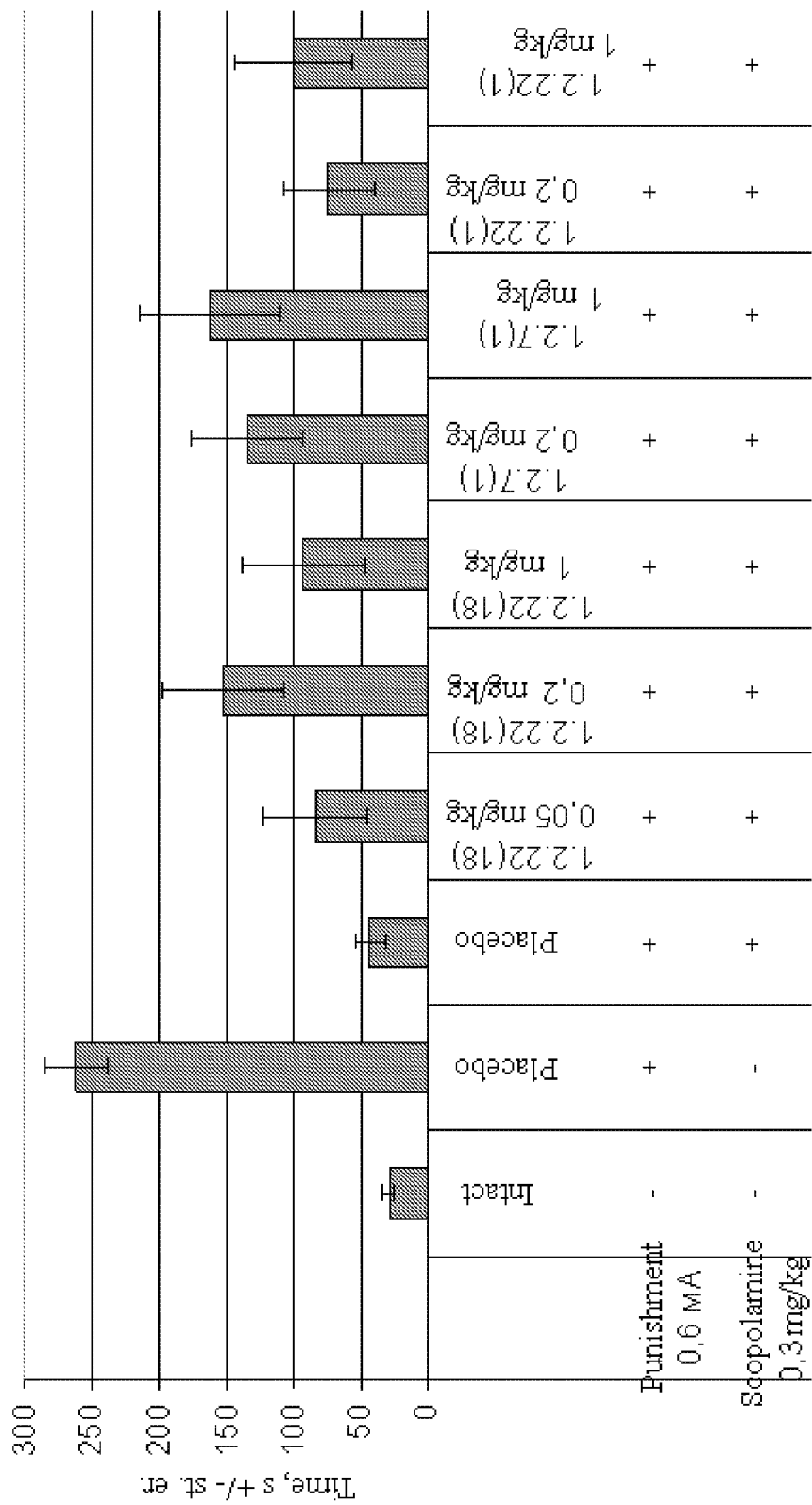

wherein: X=S, SO or NH; $R^1$ represents hydrogen, optionally substituted $C_1$-$C_3$alkyl, cycloalkyl, adamantyl, aryl or heterocyclyl; $R^2$ represents hydrogen, halogen, optionally substituted $C_1$-$C_3$alkyl, substituted hydroxyl, aryldiazenyl or optionally substituted amino group; $R^3$ represents hydrogen, optionally substituted $C_1$-$C_3$alkyl, substituted hydroxyl, pyridyl or optionally substituted amino group, besides, in cases when X=S or X=NH, at least one of $R^1$, $R^2$ or $R^3$ represent substituted $C_1$-$C_3$alkyl, cycloalkyl, adamantyl, aryl, heterocyclyl, halogen, substituted hydroxyl, optionally substituted amino group, aryldiazenyl, or at least two of $R^1$, $R^2$ or $R^3$ represent hydrogen; $R^4$ represents $C_1$-$C_3$alkyl; $R^5$ represents hydrogen, one or two halogens, $C_1$-$C_3$alkyl or optionally substituted hydroxyl.

13 Claims, 19 Drawing Sheets

(56) References Cited

OTHER PUBLICATIONS

Foley A.G.; Murphy K.J.; Hirst W.D.; Gallagher H.C.; Hagan J.J.; Upton N.; Walsh F.S.; Regan C.M.: The 5-HT(6) receptor antagonist SB-271046 reverses scopolamine-disrupted consolidation of a passive avoidance task and ameliorates spatial task deficits in aged rats. Neuropsychopharmacology vol. 29, 2004, pp. 93-100.

Riemer C.; Borroni E; Levet-Trafit B.; Martin J.R.; Poli S.; Porter R.H.; Bos M.: Influence of the 5-HT6 receptor on acetylcholine release in the cortex: pharmacological characterization of 4-(2-bromo-6-pyrroliclin-1-ylpyridine-4-sulfonyl)phenylarnine, a potent and selective 5-HT6 receptor antagonist. J Med. Chem. vol. 46, 2003, pp. 1273-1276.

King M.V.; Woolley M.L.; Topham I.A.; Sleight A.J.; Marsden C.A. Fone K.C. 5-HT6 receptor antagonists reverse delay-dependent deficits in novel object discrimination by enhancing consolidation an effect sensitive to NMDA receptor antagonism. Neuropharmacology vol. 47, 2004, pp. 195-204.

Vicker S.P.; Dourish C.T.: Serotonin receptor ligands and the treatment of obesity. Curr. Opin. Investig. Drugs. vol. 5, 2004, pp. 377-388.

Davies S.L.: Drug discovery targets: 5-HT6 receptor. Drug Future vol. 30, 2005, pp. 479-495.

Woolley M.L.: 5-HT6 receptors. Curr. Drug Targets CNS Neurol. Disord. vol. 3, 2004, pp. 59-79.

Monsma FJ Jr; Shen Y; Ward RP; Hamblin MW; Sibley DR: Cloning and expression of a novel serotonin receptor with high affinity for tricyclic psychotropic drugs. Mol Pharmacol. vol. 43, 1993, pp. 320-327.

Berge S.M. et al.: Pharmaceutical Salts. J.Pharm.Sci. vol. 66, 1977, pp. 1-19.

Kirkpatrick We et al.: 3-HALO-5,7-Dimethylpyrazolo[1,5-A] Pyrimidines, a Nonbenzodiazepinoid Class of Antianxiety Agents Devoid of Potentiation of Central Nervous System Depressant Effects of Ethanol or Barbiturates. Journal of Medicinal Chemistry, ACS, US, vol. 20, No. 3, Mar. 1, 1977, pp. 386-393.

\* cited by examiner

SUBSTITUTED 3-ARYLSULFONYL-PYRAZOLO[1,5-A]PYRIMIDINES, SEROTONIN 5-HT6 RECEPTOR ANTAGONISTS AND METHODS FOR THE PRODUCTION AND USE THEREOF

FIELD OF THE INVENTION

The invention relates to novel substituted 3-arylsulfonyl-pyrazolo[1,5-a]pyrimidines, serotonin 5-HT$_6$ receptor antagonists, active ingredients and pharmaceutical compositions, comprising the said compounds as active ingredients, method for treatment and prophylaxis of various central nervous system (CNS) diseases, cognitive and neurodegenerative diseases. The basis of pharmacological effect of novel drug substances is their ability to interact with serotonin 5-HT$_6$ receptors playing the key role in treatment of CNS diseases, in particular, Alzheimer's disease (AD), Huntington's disease, schizophrenia, other neurodegenerative diseases, cognitive disorders and obesity.

BACKGROUND OF THE INVENTION

Usefulness of selective serotonin 5-HT$_6$ receptor antagonists for treatment of CNS diseases, in particular, schizophrenia, AD and other neurodegenerative diseases and cognitive disorders was proved conclusively in clinical practice and is regarded to be very perspective in medicine of future [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. At mammals these receptors are localized exclusively in CNS, and mainly in parts of brain responsible for training and memory [Ge'rard C., Martres M.-P., Lefe'vre K., Miguel M.-C., Verge' D., Lanfumey L., Doucet E., Hamon M., El Mestikawy S. Immuno-localisation of serotonin 5-HT$_6$ receptor-like material in the rat central nervous system. *Brain Research.* 1997; 746:207-219]. Besides, it was shown, that 5-HT$_6$ receptors are modulators of the whole number of neuromediator systems, including cholinergic, noradrenergic, glutamatergic and dopaminergic [Dawson L. A., Nguyen H. Q., Li P. The 5-HT(6) receptor antagonist SB-271046 selectively enhances excitatory neurotransmission in the rat frontal cortex and hippocampus. *Neuropsychopharmacology.* 2001; 25:662-668]. Taking into account the fundamental role of these systems in normal cognitive processes and also their dysfunction at neurodegeneration, exclusive role of 5-HT$_6$ receptors in forming normal and "pathological" memory becomes obvious. In a large number of nowadays publications it was shown that blocking of 5-HT$_6$ receptors leads to considerable enhancement of memory consolidation in various animal models of training-memorizing-reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100. Riemer C., Borroni E., Levet-Trafit B., Martin J. R., Poli S., Porter R. H., Bos M. Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-HT$_6$ receptor antagonist. *J. Med. Chem.* 2003; 46:1273-1276. King M. V., Woolley M. L., Topham I. A., Sleight A. J., Marsden C. A., Fone K. C. 5-HT6 receptor antagonists reverse delay-dependent deficits in novel object discrimination by enhancing consolidation an effect sensitive to NMDA receptor antagonism. *Neuropharmacology* 2004; 47:195-204]. It was also demonstrated that considerable enhancement of cognitive functions in aged rats in Morrison's water maze experiment took place under the action of 5-HT$_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100]. Recently more thorough understanding of 5-HT$_6$ receptor function in cognitive processes and more accurate conceptions concerning possible pharmacophoric properties of their antagonists were achieved. [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. This resulted in preparation of highly affine selective ligands ("molecular tools"), and afterwards clinical candidates. At present a number of 5-HT$_6$ receptor antagonists are at various phases of clinical trial as potential ingredients for treatment of AD, Huntington's disease, schizophrenia (antipsychotic) and other neurodegenerative and cognitive diseases (Table 1) [http://integrity.prous.com].

TABLE 1

Antagonists of 5-HT$_6$ receptors as drug candidates

| Medicament | Clinical phase of testing | Developer | Therapeutic group |
| --- | --- | --- | --- |
| Dimebon ™ | Phase III | Medivation (USA) | Alzheimer's disease treatment |
| SGS-518 | Phase II | Lilly, Saegis | Cognitive diseases treatment |
| SB-742457 | Phase II | GlaxoSmithKline | Alzheimer's disease treatment; Antipsychotic |
| Dimebon* | Phase I/IIa | Medivation (USA) | Huntington's disease treatment |
| Dimebon* | Phase II | (Russia) | Schizophrenia |
| PRX-07034 | Phase I | Epix Pharm. | Obesity treatment; Antipsychotic; Cognitive diseases treatment |
| SB-737050A | Phase II | GlaxoSmithKline | Antipsychotic |
| BVT-74316 | Phase I | Biovitrum | Obesity treatment |
| SAM-315 | Phase I | Wyeth Pharm. | Alzheimer's disease treatment |
| SYN-114 | Phase I | Roche, Synosis Ther. | Cognitive diseases treatment |
| BGC-20-761 | Preclinical | BTG (London) | Antipsychotic; Cognitive diseases treatment |
| FMPO | Preclinical | Lilly | Antipsychotic |
| Dimebon ™ | Preclinical | (Russia) | Insult treatment |

Another attractive property of 5-HT$_6$ receptor antagonists is their ability to suppress appetite that can lead to preparation of essentially novel remedies for overweight lowering and obesity treatment on their basis. [Vicker S. P., Dourish C. T. Serotonin receptor ligands and the treatment of obesity. *Curr. Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. Davies S. L. Drug discovery targets: 5-HT$_6$ receptor. *Drug Future.* 2005; 30:479-495], the mechanism of it is based on the suppression of γ-aminobutyric acid signaling by 5-HT$_6$ receptor antagonists and increasing of α-melanocyte-stimulating hormone emission, that, finally, results in lowering of food demand [Woolley M. L. 5-HT$_6$ receptors. *Curr. Drug Targets CNS Neurol. Disord.* 2004; 3:59-79]. Now two antagonists of 5-HT$_6$ receptors are at the first phase of clinical testing as drug candidates for obesity treatment (Table 1) [http://integrity.prous.com].

In this context searching for new selective and effective serotonin 5-HT$_6$ receptor antagonists seems to be original and perspective approach to the development of novel drug substances for treatment of a great number of neurological and neurodegenerative diseases and cognitive disorders.

In scientific literature there are many publications dedicated to various biologically active arylsulfonyl substituted azaheterocycles, among them serotonin receptor ligands. For example, substituted 1-(2-aminoethyl)-4-(arylsulfonyl)pyrazoles of the general formula A1 were described as serotonin 5-HT$_{2c}$ receptor ligands [WO 2003057674 A1] and substituted 7-amino-3-(sulfonyl)pyrazolo[1,5-a]pyrimidines A2 as serotonin 5-HT$_6$ receptor antagonists [EP 9411994 A1, 1999]

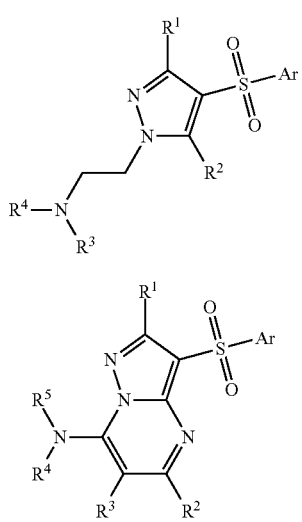

A1: Ar=alkyl, aryl; R$^1$ and R$^2$=H, OH, alkyl, alkoxy; R$^3$ and R$^4$=H, alkyl, aryl.
A2: Ar=aryl, heterocyclyl; R$^1$=H, alkyl, alkylthio; R$^2$=H, alkyl, halogen; R$^3$=H, alkyl, hydroxyalkyl; R$^4$ and R$^5$=H; NR$^4$R$^5$=piperazinyl.

With the aim of the development of novel highly effective medicament the authors of the invention carried out widespread investigation in the field of substituted 3-(arylsulfonyl)-pyrazolo[1,5-a]pyrimidines, as a result of which novel substituted 3-arylsulfonyl-pyrazolo[1,5-a]pyrimidines and novel drug substances which are selective 5-HT$_6$ receptor antagonists have been found.

DISCLOSURE OF THE INVENTION

In the context of the invention, the terms are generally defined as follows.
"Agonists" mean ligands being bound to the receptors of definite type actively promote transferring their specific signal and by that, cause the biological response of the cell.
"Alkyl" means aliphatic hydrocarbon straight or branched group with 1-12 carbon atoms. Branched means alkyl chain with one or more "lower alkyl" side substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k{}^aR_{k+1}{}^aN-$, $R_k{}^aR_{k+1}{}^aNC(=O)-$, $R_k{}^aR_{k+1}{}^aNC(=S)-$, $R_k{}^aR_{k+1}{}^aNSO_2-$, where $R_k{}^a$ and $R_{k+1}{}^a$ independently of each other represent "amino group substituent", the meanings of which are defined herein, for example, hydrogen, alkyl, aryl, aralkyl, heteroaralkyl, heterocyclyl or heteroaryl, or $R_k{}^a$ and $R_{k+1}{}^a$ together with the nitrogen atom, they are attached to, form through $R_k{}^a$ and $R_{k+1}{}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^aR_{k+1}{}^aN-$, $R_k{}^aR_{k+1}{}^aNC(=O)-$, annelated arylheterocyclenyl, annelated arylheterocyclyl.
"Alkoxy" means alkyl-O-group, in which alkyl is defined herein. The preferred alkoxy groups are methoxy, ethoxy, n-propoxy, iso-propoxy and n-butoxy.
"Alkyloxyalkyl" means $C_nH_{2n+1}OC_mH_{2m}$ group, in which alkyl is defined herein.
"Antagonists" mean ligands being bound to the definite receptors do not cause active cellular responses. Antagonists prevent linkage between agonists and receptors and by that block specific receptor signal transmission.
"Aryl" means aromatic mono- or polycyclic system with 6-14 carbon atoms, predominantly from 6 to 10 C-atoms. Aryl may have one or more "cyclic system substituents" of the same or different structure. Phenyl, substituted phenyl, naphthyl, or substituted naphthyl are the representatives of aryl groups. Aryl could be annelated with nonaromatic cyclic system or heterocycle.
"Arylsulfonyl" means aryl-SO$_2$-group, in which the meaning of aryl is defined herein.
"Halogen" means fluorine, chlorine, bromine and iodine. Preference is given to fluorine, chlorine and bromine.
"Hydroxyalkyl" means HOC$_m$H$_{2m}$—group, in which alkyl is defined herein.
"Substituent" means a chemical radical attached to the scaffold (fragment), for example, "alkyl substituent", "amino group substituent", "carbamoyl substituent", and "cyclic system substituent", the meanings of which are defined herein.
"Hydroxy group substitutent" means a substituent attached to hydroxyl, such as alkyl, aryl, heteroaryl, aralkyl, heteroaralkyl, hydroxyalkyl, acyl, aroyl, alkyloxyalkyl, aryloxyalkyl, heterocyclyloxyalkyl and others.
"Drug substance" means physiologically active compound of synthetic or other (biotechnological, vegetable, animal, microbe and so on) origin exhibiting pharmacological activity and being an active ingredient of pharmaceutical composition suitable for preparation and production of medicaments.

"Medicament"—is a compound or a mixture of compounds representing a pharmaceutical composition in the form of tablets, capsules, injections, ointments and other drug products intended for restoration, improvement or modification of physiological functions at humans and animals, and for prophylaxis and treatment of diseases, diagnostics, anesthesia, contraception, cosmetology and others.

"Ligands" (from Latin ligo) represent chemical compounds (small molecule, peptide, protein, inorganic ion, and so on) capable to interact with receptors which convert this interaction into specific signal.

"Lower alkyl" means straight or branched alkyl group with 1-4 carbon atoms.

"Sulfanyl group" means R—S-group in which R represents alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings of which are defined herein.

"Sulfinyl group" means R—SO-group, in which R represents alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings of which are defined herein.

"Sulfonyl group" means R—SO$_2$-group, in which R could be selected from alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings of which are defined herein.

"Therapeutic cocktail" is a simultaneously administered combination of two or more drug substances with different mechanisms of pharmacological action and aimed at different biotargets taking part in pathogenesis of the disease.

"Pharmaceutical composition" means a composition comprising, at least, one of the compounds of the general formula 1 and, at least, one of the components selected from pharmaceutically acceptable and pharmacologically compatible fillers, solvents, diluents, auxiliaries, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dosage. Examples of suitable suspending agents are: ethoxylated isostearyl alcohol, polyoxyethene, sorbitol and sorbitol ether, microcrystalline cellulose, aluminum metahydroxide, bentonite, agar-agar and tragacant and their mixtures as well. Protection against microorganism action can be provided by various antibacterial and antifungal agents, such as: parabens, chlorobutanol, sorbic acid, and similar compounds. Composition may also contain isotonic agents, such as: sugar, sodium chloride, and similar compounds. Prolonged effect of the composition may be achieved by the agents inhibiting absorption of the active ingredient, for example, aluminum monostearate and gelatin. Examples of suitable carriers, solvents, diluents and delivery agents include water, ethanol, polyalcohols and their mixtures, natural oils (such as olive oil) and injection-grade organic esters (such as ethyl oleate). Examples of fillers are: lactose, milk-sugar, sodium citrate, calcium carbonate, calcium phosphate and the like. Examples of disintegrators and distributors are: starch, alginic acid and its salts, and silicates. Examples of suitable lubricants are: magnesium stearate, sodium lauryl sulfate, talc and polyethylene glycol of high molecular weight. Pharmaceutical composition for peroral, sublingual, transdermal, intramuscular, intravenous, subcutaneous, local or rectal administration of active ingredient, alone or in combination with another active compound, may be administered to humans and animals in standard administration form, or mixture with traditional pharmaceutical carriers. Suitable standard administration forms include peroral forms such as tablets, gelatin capsules, pills, powders, granules, chewing-gums and peroral solutions or suspensions, for example, therapeutic cocktail; sublingual and transbuccal administration forms; aerosols; implants; local, transdermal, subcutaneous, intramuscular, intravenous, intranasal or intraocular forms and rectal administration forms.

Pharmaceutical compositions, as a rule, are prepared by means of conventional procedures which imply mixing of active compound with liquid or overgrounded solid carrier.

"Pharmaceutically acceptable salt" means relatively nontoxic organic or inorganic salts of acids and bases disclosed in this invention. Salts could be prepared in situ in process of synthesis, isolation or purification of compounds or prepared specially. In particular, salts of bases could be prepared starting from purified bases disclosed in the invention and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulfonates, malonates, salicylates, propionates, ethane sulfonates, benzene sulfonates, sulfamates and the like (Detailed description of the properties of such salts is given in: Berge S. M., et al., "Pharmaceutical Salts" J. Pharm. Sci., 1977, 66: 1-19). Salts of the disclosed acids may be prepared by the reaction of purified acids with a suitable base; moreover, metal salts and amine salts may be synthesized too. Metal salts are salts of sodium, potassium, calcium, barium, magnesium, lithium and aluminum; sodium and potassium salts being preferred. Suitable inorganic compounds from which metal salts can be prepared are: sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of the disclosed acid salts are amines and amino acids the basicity of which is high enough to produce stable salts suitable for medicinal purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl) aminomethane and the like. Besides, salts can be prepared using some tetraalkylammonium hydroxides, such as: holine, tetramethylammonium, tetraethylammonium, and the like. Amino acids may be selected from the main amino acids—lysine, ornithine and arginine.

The subject of the present invention is novel substituted 3-arylsulfonyl-pyrazolo[1,5-a]pyrimidines or the general formula 1 and pharmaceutically acceptable salts and/or hydrates thereof,

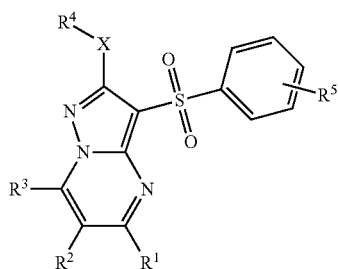

1 wherein: X=S, SO or NH,
$R^1$ represents hydrogen, optionally substituted $C_1$-$C_3$alkyl, cycloalkyl, adamantyl, aryl or heterocyclyl;
$R^2$ represents hydrogen, halogen, optionally substituted $C_1$-$C_3$alkyl, substituted hydroxyl, aryldiazenyl or optionally substituted amino group;
$R^3$ represents hydrogen, optionally substituted $C_1$-$C_3$alkyl, substituted hydroxyl, pyridyl or optionally substituted amino group, at that in cases when X=S or X=NH, at least one of $R^1$,
$R^2$ or $R^3$ represents substituted $C_1$-$C_3$alkyl, cycloalkyl, adamantyl, aryl, heterocyclyl, halogen, substituted hydroxyl, optionally substituted amino group, aryldiazenyl or, at least two of $R^1$, $R^2$ or $R^3$ represent hydrogen;
$R^4$ represents $C_1$-$C_3$alkyl;
$R^5$ represents hydrogen, one or two halogens, $C_1$-$C_3$alkyl or optionally substituted hydroxyl.

The preferred substituted 3-arylsulfonyl-pyrazolo[1,5-a]pyrimidines of the general formula 1 are the compounds of the general formulas 1.1, 1.2 and pharmaceutically acceptable salts and/or hydrates thereof,

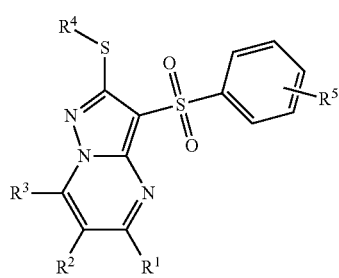

1.1

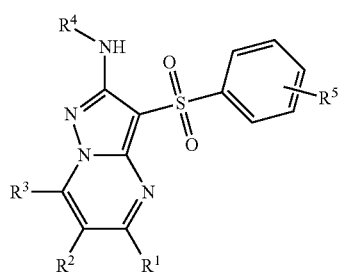

1.2 wherein: $R^1$, $R^2$, $R^3$, $R^4$ and $R^5$ have the above meanings.

The preferred substituted 3-arylsulfonyl-2-alkylsulfanyl-pyrazolo[1,5-a]pyrimidines of the general formula 1.1 are the compounds of the general formulas 1.1.1, 1.1.2, 1.1.3, 1.1.4, 1.1.5, 1.1.6, 1.1.7, 1.1.8, 1.1.9 and 1.1.10, and pharmaceutically acceptable salts and/or hydrates thereof,

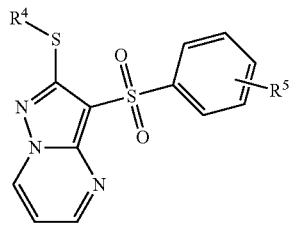

1.1.1

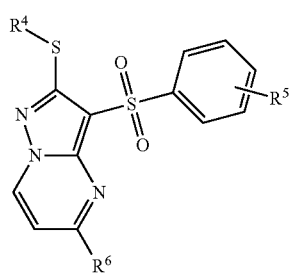

1.1.2

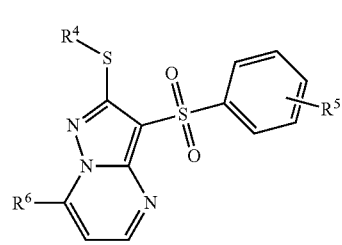

1.1.3

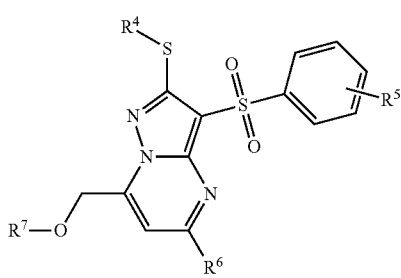

1.1.4

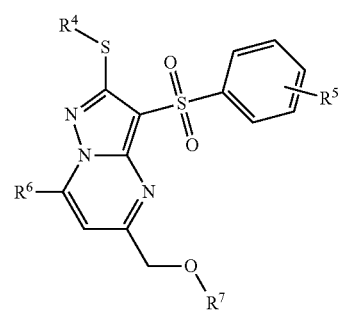

1.1.5

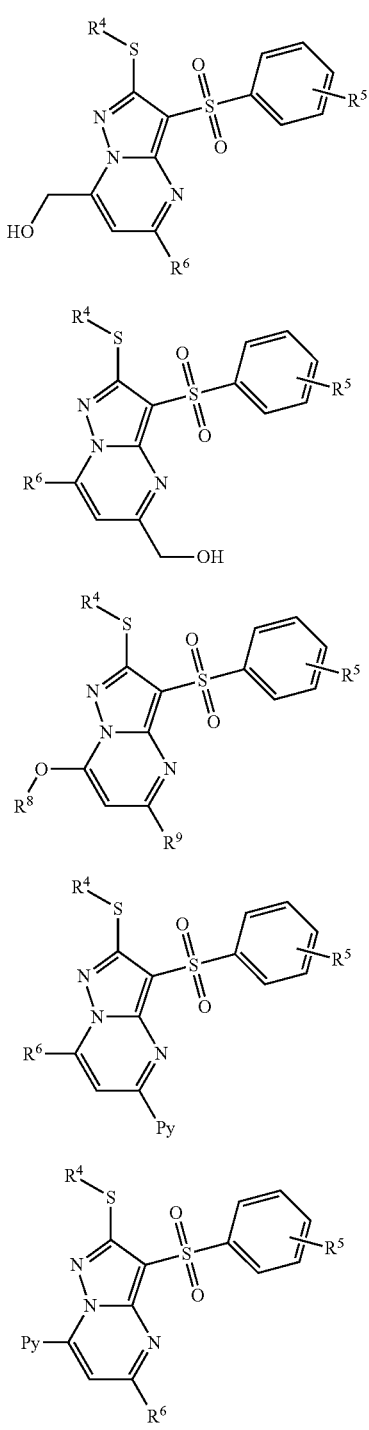

wherein: $R^4$ and $R^5$ have the above meanings; $R^6$ and $R^7$ independently of each other represent hydrogen or $C_1$-$C_3$alkyl; $R^8$ represents hydroxyl group substituent; $R^9$ represents $C_1$-$C_3$alkyl or pyridyl; Py represents pyridyl.

The preferred substituted 2-methylsulfanyl-3-arylsulfonyl-pyrazolo[1,5-a]pyrimidines of the general formulas 1.1.1 and 1.1.1-1.1.10 are the compounds selected from the group consisting of: 2-methylsulfanyl-3-phenylsulfonyl-pyrazolo[1,5-a]pyrimidine 1.1.1(1), 2-methylsulfanyl-3-(4-fluorophenylsulfonyl)-pyrazolo[1,5-a]pyrimidine 1.1.1(2), 2-methylsulfanyl-3-(3-fluorophenylsulfonyl)-pyrazolo[1,5-a]pyrimidine 1.1.1(3), 2-methylsulfanyl-3-(3-chlorophenylsulfonyl)-pyrazolo[1,5-a]pyrimidine 1.1.1(4), 2-methylsulfanyl-3-(4-fluoro-3-chlorophenylsulfonyl)-pyrazolo[1,5-a]pyrimidine 1.1.1(5), 5-methyl-2-methylsulfanyl-3-phenylsulfonyl-pyrazolo[1,5-a]pyrimidine 1.1.2(1), 5-methyl-2-methylsulfanyl-3-(4-fluorophenylsulfonyl)-pyrazolo[1,5-a]pyrimidine 1.1.2(2), 5-methyl-2-methylsulfanyl-3-(3-fluorophenylsulfonyl)-pyrazolo[1,5-a]pyrimidine 1.1.2(3), 5-methyl-2-methylsulfanyl-3-(3-chlorophenylsulfonyl)-pyrazolo[1,5-a]pyrimidine 1.1.2(4), 5-methyl-2-methylsulfanyl-3-(4-fluoro-3-chlorophenylsulfonyl)-pyrazolo[1,5-a]pyrimidine 1.1.2(5), 7-methyl-2-methylsulfanyl-3-phenylsulfonyl-pyrazolo[1,5-a]pyrimidine 1.1.3(1), 7-methyl-2-methylsulfanyl-3-(4-fluorophenylsulfonyl)-pyrazolo[1,5-a]pyrimidine 1.1.3(2), 7-methyl-2-methylsulfanyl-3-(3-fluorophenylsulfonyl)-pyrazolo[1,5-a]pyrimidine 1.1.3(3), 7-methyl-2-methylsulfanyl-3-(3-chlorophenylsulfonyl)-pyrazolo[1,5-a]pyrimidine 1.1.3(4), 7-methyl-2-methylsulfanyl-3-(4-fluoro-3-chlorophenylsulfonyl)-pyrazolo[1,5-a]pyrimidine 1.1.3(5), 5-methyl-2-methylsulfanyl-7-(methoxymethyl)-3-phenylsulfonyl-pyrazolo[1,5-a]pyrimidine 1.1.4(1), 5-methyl-2-methylsulfanyl-7-(methoxymethyl)-3-(4-fluoro phenylsulfonyl)-pyrazolo[1,5-a]pyrimidine 1.1.4(2), 5-methyl-2-methylsulfanyl-7-(methoxymethyl)-3-(3-fluorophenylsulfonyl)-pyrazolo[1,5-a]pyrimidine 1.1.4(3), 5-methyl-2-methylsulfanyl-7-(methoxymethyl)-3-(3-chlorophenylsulfonyl)-pyrazolo[1,5-a]pyrimidine 1.1.4(4), 5-methyl-2-methylsulfanyl-7-(methoxymethyl)-3-(4-fluoro-3-chlorophenylsulfonyl)-pyrazolo[1,5-a]pyrimidine 1.1.4(5), 7-methyl-2-methylsulfanyl-5-(methoxymethyl)-3-phenylsulfonyl-pyrazolo[1,5-a]pyrimidine 1.1.5(1), 7-methyl-2-methylsulfanyl-5-(methoxymethyl)-3-(4-fluorophenylsulfonyl)-pyrazolo[1,5-a]pyrimidine 1.1.5(2), 7-methyl-2-methylsulfanyl-5-(methoxymethyl)-3-(3-fluorophenylsulfonyl)-pyrazolo[1,5-a]pyrimidine 1.1.5(3), 7-methyl-2-methylsulfanyl-5-(methoxymethyl)-3-(3-chlorophenylsulfonyl-pyrazolo[1,5-a]pyrimidine 1.1.5(4), 7-methyl-2-methylsulfanyl-5-(methoxymethyl)-3-(4-fluoro-3-chlorophenylsulfonyl)-pyrazolo[1,5-a]pyrimidine 1.1.5(5), 7-(hydroxymethyl)-5-methyl-2-methylsulfanyl-3-phenylsulfonyl-pyrazolo[1,5-a]pyrimidine 1.1.6(1), 7-(hydroxymethyl)-5-methyl-2-methylsulfanyl-3-(4-fluorophenylsulfonyl)-pyrazolo[1,5-a]pyrimidine 1.1.6(2), 7-(hydroxymethyl)-5-methyl-2-methylsulfanyl-3-(3-fluorophenylsulfonyl)-pyrazolo[1,5-a]pyrimidine 1.1.6(3), 7-(hydroxymethyl)-5-methyl-2-methylsulfanyl-3-(3-chlorophenylsulfonyl)-pyrazolo[1,5-a]pyrimidine 1.1.6(4), 7-(hydroxymethyl)-5-methyl-2-methylsulfanyl-3-(4-fluoro-3-chlorophenylsulfonyl)-pyrazolo[1,5-a]pyrimidine 1.1.6(5), 5-(hydroxymethyl)-7-methyl-2-methylsulfanyl-3-phenylsulfonyl-pyrazolo[1,5-a]pyrimidine 1.1.7(1), 5-(hydromethyl)-7-methyl-2-methylsulfanyl-3-(4-fluorophenylsulfonyl)-pyrazolo[1,5-a]pyrimidine 1.1.7(2), 5-(hydroxymethyl)-7-methyl-2-methylsulfanyl-3-(3-fluorophenylsulfonyl)-pyrazolo[1,5-a]pyrimidine 1.1.7(3), 5-(hydroxymethyl)-7-methyl-2-methylsulfanyl-3-(3-chlorophenylsulfonyl)-pyrazolo[1,5-a]pyrimidine 1.1.7(4), 5-(hydroxymethyl)-7-methyl-2-methylsulfanyl-3-(4-fluoro-3-chlorophenylsulfonyl)-pyrazolo[1,5-a]pyrimidine 1.1.7(5), 2-methylsulfanyl-7-methoxy-5-(pyridin-2-yl)-3-phenylsulfonyl-pyrazolo[1,5-a]pyrimidine 1.1.8(1), 2-methylsulfanyl-7-methoxy-5-(pyridin-2-yl)-3-phenylsulfonyl-pyrazolo[1,5-a]pyrimidine 1.1.8(2), 2-methylsulfanyl-7-methoxy-5-(pyridin-3-yl)-3-phenylsulfonyl-pyrazolo[1,5-a]pyrimidine 1.1.8(3), 2-methylsulfanyl-7-methoxy-5-

(pyridin-4-yl)-3-phenylsulfonyl-pyrazolo[1,5-a]pyrimidine 1.1.8(4), 5-methyl-2-methylsulfanyl-7-methoxy-3-(4-fluorophenylsulfonyl)-pyrazolo[1,5-a]pyrimidine 1.1.8(5), 2-methylsulfanyl-5-(pyridin-2-yl)-3-phenylsulfonyl-pyrazolo[1,5-a]pyrimidine 1.1.9(1), 2-methylsulfanyl-5-(pyridin-3-yl)-3-phenylsulfonyl-pyrazolo[1,5-a]pyrimidine 1.1.9(2), 2-methylsulfanyl-5-(pyridin-4-yl)-3-phenylsulfonyl-pyrazolo[1,5-a]pyrimidine 1.1.9(3), 2-methylsulfanyl-5-(pyridin-4-yl)-3-(3-fluorophenylsulfonyl)-pyrazolo[1,5-a]pyrimidine 1.1.9(4), 2-methylsulfanyl-5-(pyridin-4-yl)-3-(3-chlorophenylsulfonyl)-pyrazolo[1,5-a]pyrimidine 1.1.9(5), 7-methyl-2-methylsulfanyl-5-(pyridin-2-yl)-3-phenylsulfonyl-pyrazolo[1,5-a]pyrimidine 1.1.9(6), 7-methyl-2-methylsulfanyl-5-(pyridin-3-yl)-3-phenylsulfonyl-pyrazolo[1,5-a]pyrimidine 1.1.9(7), 7-methyl-2-methylsulfanyl-5-(pyridin-4-yl)-3-phenylsulfonyl-pyrazolo[1,5-a]pyrimidine 1.1.9(8), 7-methyl-2-methylsulfanyl-5-(pyridin-4-yl)-3-(3-fluorophenylsulfonyl)-pyrazolo[1,5-a]pyrimidine 1.1.9(9), 7-methyl-2-methylsulfanyl-5-(pyridin-4-yl)-3-(3-chlorophenylsulfonyl)-pyrazolo[1,5-a]pyrimidine 1.1.9(10), 2-methylsulfanyl-7-(pyridin-2-yl)-3-phenylsulfonyl-pyrazolo[1,5-a]pyrimidine 1.1.10(1), 2-methylsulfanyl-7-(pyridin-3-yl)-3-phenylsulfonyl-pyrazolo[1,5-a]pyrimidine 1.1.10(2), 2-methylsulfanyl-7-(pyridin-4-yl)-3-phenylsulfonyl-pyrazolo[1,5-a]pyrimidine 1.1.10(3), 2-methylsulfanyl-7-(pyridin-4-yl)-3-(3-fluorophenylsulfonyl)-pyrazolo[1,5-a]pyrimidine 1.1.10(4), 2-methylsulfanyl-7-(pyridin-4-yl)-3-(3-chlorophenylsulfonyl)-pyrazolo[1,5-a]pyrimidine 1.1.10(5), 5-methyl-2-methylsulfanyl-7-(pyridin-2-yl)-3-phenylsulfonyl-pyrazolo[1,5-a]pyrimidine 1.1.10(6), 5-methyl-2-methylsulfanyl-7-(pyridin-3-yl)-3-phenylsulfonyl-pyrazolo[1,5-a]pyrimidine 1.1.10(7), 5-methyl-2-methylsulfanyl-7-(pyridin-4-yl)-3-phenylsulfonyl-pyrazolo[1,5-a]pyrimidine 1.1.10(8), 5-methyl-2-methylsulfanyl-7-(pyridin-4-yl)-3-(3-fluorophenylsulfonyl)-pyrazolo[1,5-a]pyrimidine 1.1.10(9), 5-methyl-2-methylsulfanyl-7-(pyridin-4-yl)-3-(3-chlorophenylsulfonyl)-pyrazolo[1,5-a]pyrimidine 1.1.10(10) and pharmaceutically acceptable salts and/or hydrates thereof.

The preferred substituted 2-alkylsulfanyl-3-arylsulfonyl-pyrazolo[1,5-a]pyrimidines of the general formula 1.1 are the esters of the general formulas 1.1.11, 1.1.12 and 1.1.13, and pharmaceutically acceptable salts and/or hydrates thereof,

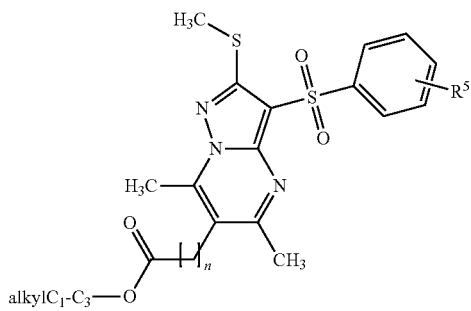

1.1.11

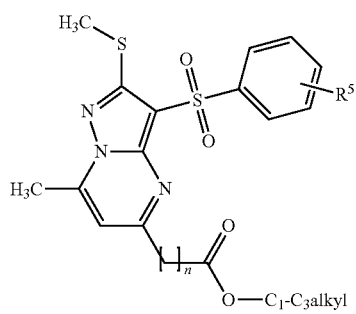

1.1.12

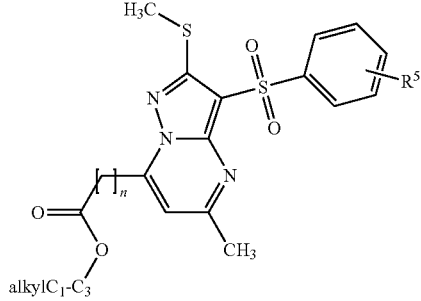

1.1.13 wherein: $R^5$ has the above meaning, n=0, 1, 2 or 3.

The preferred substituted 2-alkylsulfanyl-3-arylsulfonyl-pyrazolo[1,5-a]pyrimidines of the general formula 1.1 are the acids of the general formulas 1.1.14, 1.1.15 and 1.1.16, and pharmaceutically acceptable salts and/or hydrates thereof,

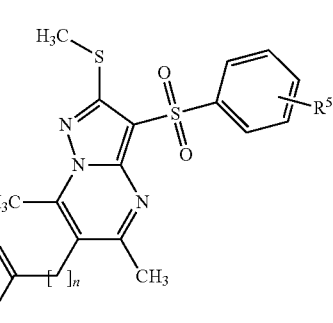

1.1.14

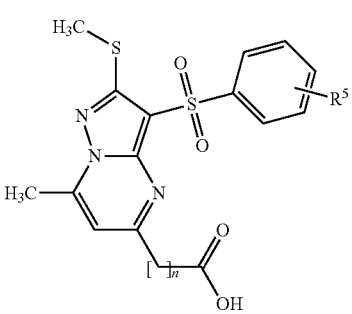

1.1.15

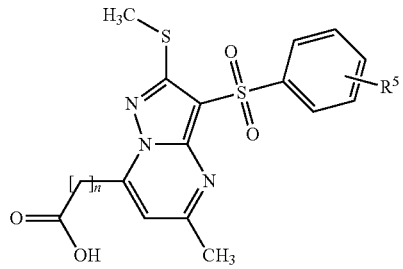

1.1.16 wherein: n and $R^5$ have the above meanings.

The preferred substituted 2-alkylsulfanyl-3-arylsulfonyl-pyrazolo[1,5-a]pyrimidines of the general formula 1.1 are the amides of the general formulas 1.1.17, 1.1.18 and 1.1.19, and pharmaceutically acceptable salts and/or hydrates thereof,

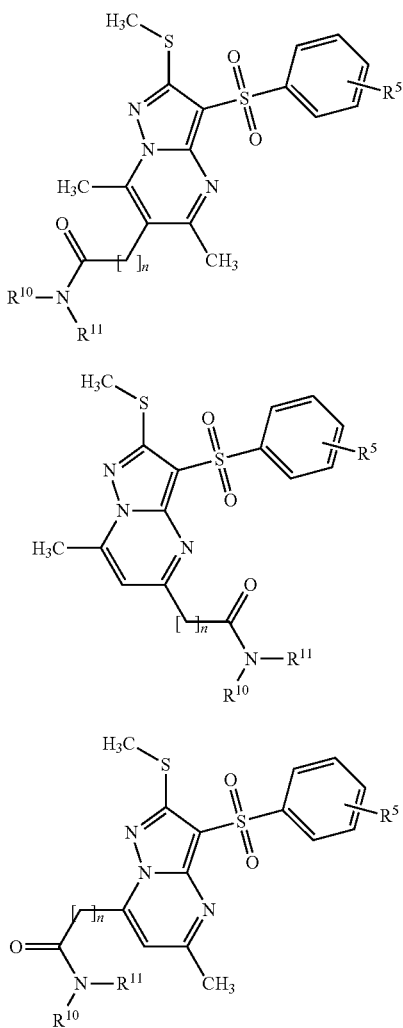

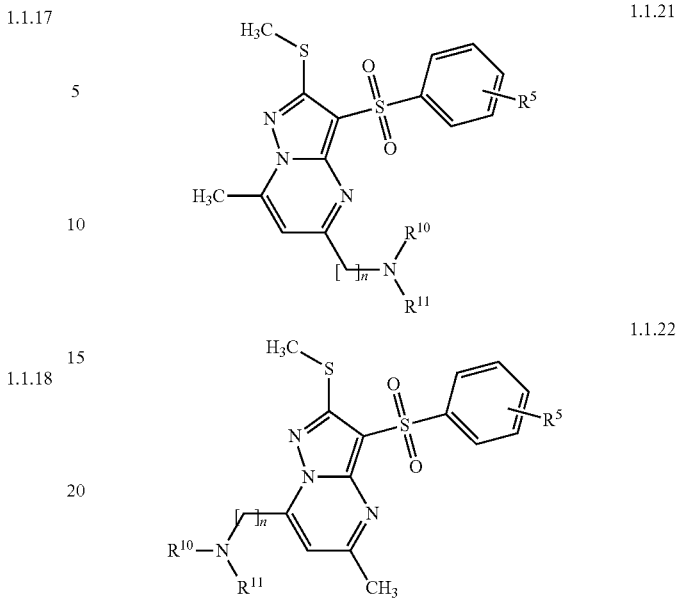

wherein: n and $R^5$ have the above meanings; $R^{10}$ and $R^{11}$ represent hydrogen, optionally substituted $C_1$-$C_3$alkyl or $R^{10}$ and $R^{11}$ together with the nitrogen atom they are attached to form optionally substituted azaheterocyclyl.

The preferred substituted 2-alkylsulfanyl-3-arylsulfonyl-pyrazolo[1,5-a]pyrimidines of the general formula 1.1 are the compounds of the general formulas 1.1.20, 1.1.21 and 1.1.22, and pharmaceutically acceptable salts and/or hydrates thereof,

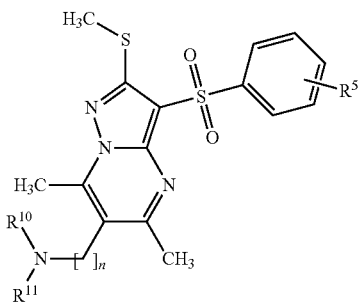

wherein: n and $R^5$, $R^{10}$ and $R^{11}$ have the above meanings.

The preferred compounds of the general formulas 1.1.20, 1.1.21 and 1.1.22 are the compounds selected from the group consisting of: 6-amino-5,7-dimethyl-2-methylsulfanyl-3-phenylsulfonyl-pyrazolo[1,5-a]pyrimidine 1.1.20(1), 6-(aminomethyl)-5,7-dimethyl-2-methylsulfanyl-3-phenylsulfonyl-pyrazolo[1,5-a]pyrimidine 1.1.20(2), 6-(2-aminoethyl)-5,7-dimethyl-2-methylsulfanyl-3-phenylsulfonyl-pyrazolo[1,5-a]pyrimidine 1.1.20(3), 6-(3-aminopropyl)-5,7-dimethyl-2-methylsulfanyl-3-phenylsulfonyl-pyrazolo[1,5-a]pyrimidine 1.1.20(4), 6-(aminomethyl)-5,7-dimethyl-2-methylsulfanyl-3-(3-chlorophenylsulfonyl)-pyrazolo[1,5-a]pyrimidine 1.1.20(5), 6-(aminomethyl)-5,7-dimethyl-2-methylsulfanyl-3-(3-fluorophenylsulfonyl)-pyrazolo[1,5-a]pyrimidine 1.1.20(6), 6-(aminomethyl)-5,7-dimethyl-2-methylsulfanyl-3-(4-fluoro-3-chlorophenylsulfonyl)-pyrazolo[1,5-a]pyrimidine 1.1.20(7), 6-(2-aminoethyl)-5,7-dimethyl-2-methylsulfanyl-3-(3-chlorophenylsulfonyl)-pyrazolo[1,5-a]pyrimidine 1.1.20(8), 6-(2-aminoethyl)-5,7-dimethyl-2-methylsulfanyl-3-(3-fluorophenylsulfonyl)-pyrazolo[1,5-a]pyrimidine 1.1.20(9), 5,7-dimethyl-6-(dimethylaminomethyl)-2-methylsulfanyl-3-phenylsulfonyl-pyrazolo[1,5-a]pyrimidine 1.1.20(10), 5,7-dimethyl-6-dimethylaminomethyl-2-methylsulfanyl-3-(3-chlorophenylsulfonyl)-pyrazolo[1,5-a]pyrimidine 1.1.20(11), 5,7-dimethyl-6-(dimethylaminomethyl)-2-methylsulfanyl-3-(3-fluorophenylsulfonyl)-pyrazolo[1,5-a]pyrimidine 1.1.20(12), 5,7-dimethyl-6-(dimethylaminomethyl)-2-methylsulfanyl-3-(4-fluoro-3-chlorophenylsulfonyl)-pyrazolo[1,5-a]pyrimidine 1.1.20(13), 5,7-dimethyl-6-(2-dimethylamino)ethyl-2-methylsulfanyl-3-phenylsulfonyl-pyrazolo[1,5-a]pyrimidine 1.1.20(14), 5,7-dimethyl-6-(2-dimethylamino)ethyl-2-methylsulfanyl-3-(3-chlorophenylsulfonyl)-pyrazolo[1,5-a]pyrimidine 1.1.20(15), 5,7-dimethyl-6-(2-dimethylamino)ethyl-2-methylsulfanyl-3-(3-fluorophenylsulfonyl)-pyrazolo[1,5-a]pyrimidine 1.1.20(16), 5,7-dimethyl-6-(2-dimethylamino)ethyl-2-methylsulfanyl-3-(4-fluoro-3-chlorophenylsulfonyl)-pyrazolo[1,5-a]pyrimidine 1.1.20(17), 5-(aminomethyl)-7-methyl-2-methylsulfanyl-3-phenylsulfonyl-pyrazolo[1,5-a]pyrimidine 1.1.21(1), 5-(2-aminoethyl)-7-methyl-2- methylsulfanyl-3-phenylsulfonyl-pyrazolo[1,5-a]pyrimidine 1.1.21(2), 5-(dimethylaminomethyl)-7-methyl-2-methylsulfanyl-3-phenylsulfonyl-pyrazolo[1,5-a]pyrimidine 1.1.21(3), 5-(dimethylaminomethyl)-7-methyl-2-methylsulfanyl-3-(4-fluoro-3-chlorophenylsulfonyl)-pyrazolo[1,5-a]pyrimidine 1.1.21(4), 5-(2-dimethylamino)ethyl-7-methyl-2-methylsulfanyl-3-phenylsulfonyl-pyrazolo[1,5-a]pyrimidine 1.1.21(5), 7-(aminomethyl)-5-methyl-2-methylsulfanyl-3-phenylsulfonyl-pyrazolo[1,5-a]pyrimidine 1.1.22(1), 7-(2-amino)ethyl-5-methyl-2-methylsulfanyl-3-phenylsulfonyl-pyrazolo [1,5-a]pyrimidine 1.1.22(2), 7-(dimethylaminomethyl)-5-methyl-2-methylsulfanyl-3-phenylsulfonyl-pyrazolo[1,5-a]pyrimidine 1.1.22(3), 7-(dimethylaminomethyl)-5-methyl-2-methylsulfanyl-3-(4-fluoro-3-chlorophenylsulfonyl)-pyrazolo[1,5-a]pyrimidine 1.1.22(4), 7-(2-dimethylamino)ethyl-5-methyl-2-methylsulfanyl-3-phenylsulfonyl-pyrazolo[1,5-a]pyrimidine 1.1.22(5) and pharmaceutically acceptable salts and/or hydrates thereof.

The preferred substituted 2-alkylamino-3-arylsulfonyl-pyrazolo[1,5-a]pyrimidines of the general formula 1.2 are the compounds of the general formulas 1.2.1, 1.2.2, 1.2.3, 1.2.4, 1.2.5, 1.2.6, 1.2.7, 1.2.8, 1.2.9, 1.2.10, 1.2.11 and 1.2.12 and pharmaceutically acceptable salts and/or hydrates thereof.

1.2.1
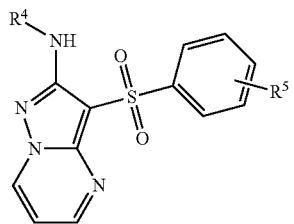

1.2.2
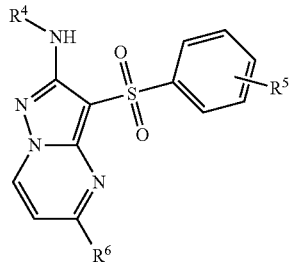

1.2.3
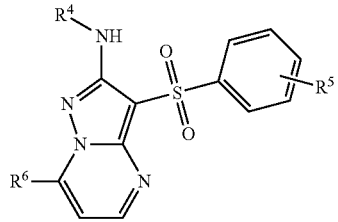

1.2.4
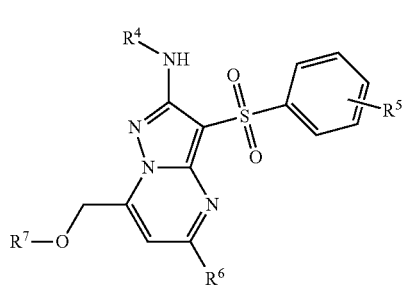

-continued 1.2.5
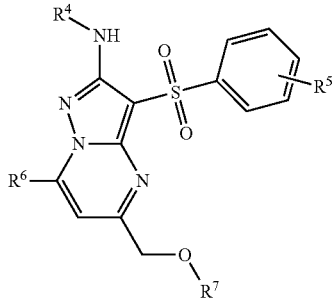

1.2.6
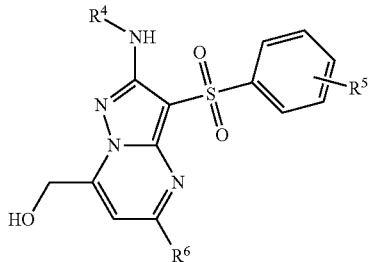

1.2.7
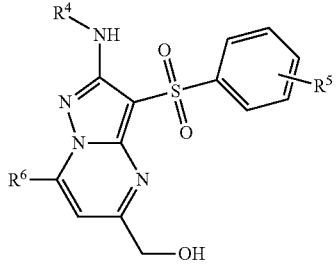

1.2.8
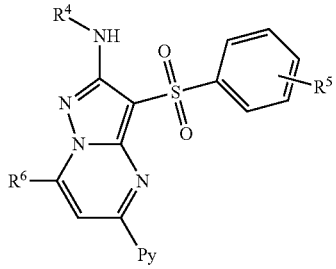

1.2.9
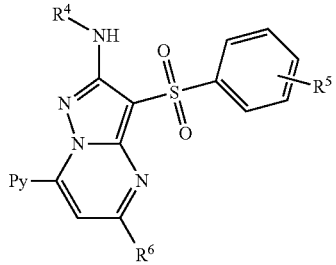

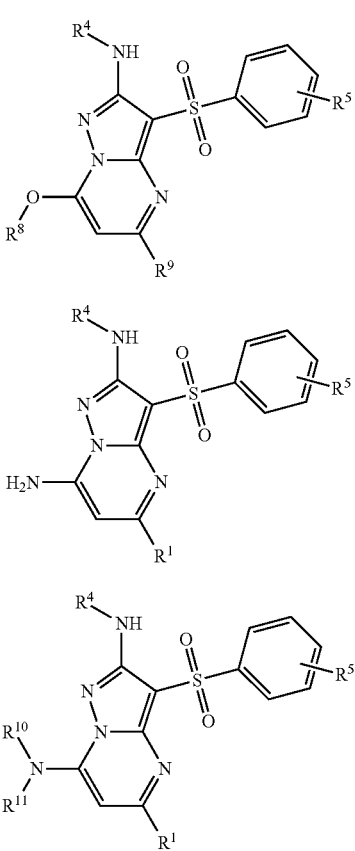

wherein: $R^1$, $R^4$, $R^5$, $R^6$, $R^7$, $R^8$, $R^9$ and Py have the above meanings;

$R^{10}$ and $R^{11}$ independently of each other represent hydrogen or $C_1$-$C_3$alkyl or $R^{10}$ and $R^{11}$ together with the nitrogen atom they are attached to form azaheterocyclyl.

The preferred substituted 2-alkylamino-3-arylsulfonyl-pyrazolo[1,5-a]pyrimidines of the general formula 1.2 are the compounds selected from the group consisting of: 2-methylamino-3-phenylsulfonyl-pyrazolo[1,5-a]pyrimidine 1.2.1(1), 2-methylamino-3-(4-fluorophenylsulfonyl)-pyrazolo[1,5-a]pyrimidine 1.2.1(2), 2-methylamino-3-(3-fluorophenylsulfonyl)-pyrazolo[1,5-a]pyrimidine 1.2.1(3), 2-methylamino-3-(3-chlorophenylsulfonyl)-pyrazolo[1,5-a]pyrimidine 1.2.1(4), 2-methylamino-3-(4-fluoro-3-chlorophenylsulfonyl)-pyrazolo[1,5-a]pyrimidine 1.2.1(5), 5-methyl-2-methylamino-3-phenylsulfonyl-pyrazolo[1,5-a]pyrimidine 1.2.2(1), 5-methyl-2-methylamino-3-(4-fluorophenylsulfonyl)-pyrazolo[1,5-a]pyrimidine 1.2.2(2), 5-methyl-2-methylamino-3-(3-fluorophenylsulfonyl)-pyrazolo[1,5-a]pyrimidine 1.2.2(3), 5-methyl-2-methylamino-3-(3-chlorophenylsulfonyl)-pyrazolo[1,5-a]pyrimidine 1.2.2(4), 5-methyl-2-methylamino-3-(4-fluoro-3-chlorophenyl)-pyrazolo[1,5-a]pyrimidine 1.2.2(5), 7-methyl-2-methylamino-3-phenylsulfonyl-pyrazolo[1,5-a]pyrimidine 1.2.3(1), 7-methyl-2-methylamino-3-(4-fluorophenylsulfonyl)-pyrazolo[1,5-a]pyrimidine 1.2.3(2), 7-methyl-2-methylamino-3-(3-fluorophenylsulfonyl)-pyrazolo[1,5-a]pyrimidine 1.2.3(3), 7-methyl-2-methylamino-3-(3-chlorophenylsulfonyl)-pyrazolo[1,5-a]pyrimidine 1.2.3(4), 7-methyl-2-methylamino-3-(4-fluoro-3-chlorophenylsulfonyl)-pyrazolo[1,5-a]pyrimidine 1.2.3(5), 5-methyl-2-methylamino-7-(methoxymethyl)-3-phenylsulfonyl-pyrazolo[1,5-a]pyrimidine 1.2.4(1), 5-methyl-2-methylamino-7-(methoxymethyl)-3-(4-fluorophenylsulfonyl)-pyrazolo[1,5-a]pyrimidine 1.2.4(2), 5-methyl-2-methylamino-7-(methoxymethyl)-3-(3-fluorophenylsulfonyl)-pyrazolo[1,5-a]pyrimidine 1.2.4(3), 5-methyl-2-methylamino-7-(methoxymethyl)-3-(3-chlorophenylsulfonyl)-pyrazolo[1,5-a]pyrimidine 1.2.4(4), 5-methyl-2-methylamino-7-(methoxymethyl)-3-(4-fluoro-3-chlorophenylsulfonyl)-pyrazolo[1,5-a]pyrimidine 1.2.4(5), 7-methyl-2-methylamino-5-(methoxymethyl)-3-phenylsulfonyl-pyrazolo[1,5-a]pyrimidine 1.2.5(1), 7-methyl-2-methylamino-5-(methoxymethyl)-3-(4-fluorophenylsulfonyl)-pyrazolo[1,5-a]pyrimidine 1.2.5(2), 7-methyl-2-methylamino-5-(methoxymethyl)-3-(3-fluorophenylsulfonyl)-pyrazolo[1,5-a]pyrimidine 1.2.5(3), 7-methyl-2-methylamino-5-(methoxymethyl)-3-(3-chlorophenylsulfonyl)-pyrazolo[1,5-a]pyrimidine 1.2.5(4), 7-methyl-2-methylamino-5-(methoxymethyl)-3-(4-fluoro-3-chlorophenylsulfonyl)-pyrazolo[1,5-a]pyrimidine 1.2.5(5), 7-(hydroxymethyl)-5-methyl-2-methylamino-3-phenylsulfonyl-pyrazolo[1,5-a]pyrimidine 1.2.6(1), 7-(hydroxymethyl)-5-methyl-2-methylamino-3-(4-fluorophenylsulfonyl)-pyrazolo[1,5-a]pyrimidine 1.2.6(2), 7-(hydroxymethyl)-5-methyl-2-methylamino-3-(3-fluorophenylsulfonyl)-pyrazolo[1,5-a]pyrimidine 1.2.6(3), 7-(hydroxymethyl)-5-methyl-2-methylamino-3-(3-chlorophenylsulfonyl)-pyrazolo[1,5-a]pyrimidine 1.2.6(4), 7-(hydroxymethyl)-5-methyl-2-methylamino-3-(4-fluoro-3-chlorophenylsulfonyl)-pyrazolo[1,5-a]pyrimidine 1.2.6(5), 5-(hydroxymethyl)-7-methyl-2-methylamino-3-phenylsulfonyl-pyrazolo[1,5-a]pyrimidine 1.2.7(1), 5-(hydroxymethyl)-7-methyl-2-methylamino-3-(4-fluorophenylsulfonyl)-pyrazolo[1,5-a]pyrimidine 1.2.7(2), 5-(hydroxymethyl)-7-methyl-2-methylamino-3-(3-fluorophenylsulfonyl)-pyrazolo[1,5-a]pyrimidine 1.2.7(3), 5-(hydroxymethyl)-7-methyl-2-methylamino-3-(3-chlorophenylsulfonyl)-pyrazolo[1,5-a]pyrimidine 1.2.7(4), 5-(hydroxymethyl)-7-methyl-2-methylamino-3-(4-fluoro-3-chlorophenylsulfonyl)-pyrazolo[1,5-a]pyrimidine 1.2.7(5). 2-methylamino-5-(pyridin-2-yl)-3-phenylsulfonyl-pyrazolo[1,5-a]pyrimidine 1.2.8(1), 2-methylamino-5-(pyridin-3-yl)-3-phenylsulfonyl-pyrazolo[1,5-a]pyrimidine 1.2.8(2), 2-methylamino-5-(pyridin-4-yl)-3-phenylsulfonyl-pyrazolo[1,5-a]pyrimidine 1.2.8(3), 2-methylamino-5-(pyridin-4-yl)-3-(3-fluorophenylsulfonyl)-pyrazolo[1,5-a]pyrimidine 1.2.8(4), 2-methylamino-5-(pyridin-4-yl)-3-(3-chlorophenylsulfonyl)-pyrazolo[1,5-a]pyrimidine 1.21.8(5), 7-methyl-2-methylamino-5-(pyridin-2-yl)-3-phenylsulfonyl-pyrazolo[1,5-a]pyrimidine 1.2.8(6), 7-methyl-2-methylamino-5-(pyridin-3-yl)-3-phenylsulfonyl-pyrazolo[1,5-a]pyrimidine 1.2.8(7), 7-methyl-2-methylamino-5-(pyridin-4-yl)-3-phenylsulfonyl-pyrazolo[1,5-a]pyrimidine 1.2.8(8), 7-methyl-2-methylamino-5-(pyridin-4-yl)-3-(3-fluorophenylsulfonyl)-pyrazolo[1,5-a]pyrimidine 1.2.8(9), 7-methyl-2-methylamino-5-(pyridin-4-yl)-3-(3-chlorophenylsulfonyl)-pyrazolo[1,5-a]pyrimidine 1.2.8(10), 2-methylamino-7-(pyridin-2-yl)-3-phenylsulfonyl-pyrazolo[1,5-a]pyrimidine 1.2.9(1), 2-methylamino-7-(pyridin-3-yl)-3-phenylsulfonyl-pyrazolo[1,5-a]pyrimidine 1.2.9(2), 2-methylamino-7-(pyridin-4-yl)-3-phenylsulfonyl-pyrazolo[1,5-a]pyrimidine 1.2.9(3), 2-methylamino-7-(pyridin-4-yl)-3-(3-fluorophenylsulfonyl)-pyrazolo[1,5-a]pyrimidine 1.2.9(4), 2-methylamino-7-(pyridin-4-yl)-3-(3-chlorophenylsulfonyl)-pyrazolo[1,5-a]pyrimidine 1.2.9(5), 5-methyl-2-methylamino-7-(pyridin-2-yl)-3-phenylsulfonyl-pyrazolo[1,5-a]pyrimidine 1.2.9(6), 5-methyl-2-methylamino-7-(pyridin-3-yl)-3-phenylsulfonyl-pyrazolo[1,5-a]pyrimidine 1.2.9(7), 5-methyl-2-methylamino-7-(pyridin-4-yl)-3-phenylsulfonyl-pyrazolo[1,5-a]pyrimidine 1.2.9(8), 5-methyl-2-methylamino-7-(pyridin-4-yl)-3-(3-fluorophenylsulfonyl)-pyrazolo[1,5-a]pyrimidine 1.2.9(9), 5-methyl-2-methylamino-7-(pyridin-4-yl)-3-(3-chlorophenylsulfonyl)-pyrazolo[1,5-a]pyrimidine 1.2.9(10), 2-methylamino-7-methoxy-5-(pyridin-2-yl)-3-phenylsulfonyl-pyrazolo[1,5-a]pyrimidine 1.2.10(1), 2-methylamino-7-methoxy-5-(pyridin-2-yl)-3-phenylsulfonyl-pyrazolo[1,5-a]pyrimidine 1.2.10(2), 2-methylamino-7-methoxy-5-(pyridin-3-yl)-3-phenylsulfonyl-pyrazolo[1,5-a]pyrimidine 1.2.10(3), 2-methylamino-7-methoxy-5-(pyridin-4-yl)-3-phenylsulfonyl-pyrazolo[1,5-a]pyrimidine 1.2.10(4), 5-methyl-2-methylamino-7-methoxy-3-(4-fluorophenylsulfonyl)-pyrazolo[1,5-a]pyrimidine 1.2.10(5), 7-amino-5-methyl-2-methylamino-3-phenylsulfonyl-pyrazolo[1,5-a]pyrimidine 1.2.11(1), 7-amino-5-methyl-2-methylamino-3-(3-chlorophenylsulfonyl)-pyrazolo[1,5-a]pyrimidine 1.2.11(2), 5-(adamantan-1-yl)-7-amino-2-methylamino-3-phenylsulfonyl-pyrazolo[1,5-a]pyrimidine 1.2.11(3), 7-amino-2-methylamino-5-phenyl-3-phenylsulfonyl-pyrazolo[1,5-a]pyrimidine 1.2.11(4), 7-amino-2-methylamino-3-phenylsulfonyl-5-(3-chlorophenyl)-pyrazolo[1,5-a]pyrimidine 1.2.11(5), 7-amino-2-methylamino-3-phenylsulfonyl-5-(furan-2-yl)-pyrazolo[1,5-a]pyrimidine 1.2.11(6), 7-amino-2-methylamino-5-(furan-2-yl)-3-(3-chlorophenylsulfonyl)-pyrazolo[1,5-a]pyrimidine 1.2.11(7), 7-amino-2-methylamino-5-(1-methylindol-3-yl)-3-phenylsulfonyl-pyrazolo[1,5-a]pyrimidine 1.2.11(8), 7-amino-2-methylamino-5-(1-methylindol-3-yl)-3-(3-chlorophenylsulfonyl)-pyrazolo[1,5-a]pyrimidine 1.2.11(9), 7-amino-2-methylamino-5-(1-methylindol-3-yl)-3-(3-fluorophenylsulfonyl)-pyrazolo[1,5-a]pyrimidine 1.2.11(10), 2,7-di(methylamino)-5-methyl-3-phenylsulfonyl-pyrazolo[1,5-a]pyrimidine 1.2.12(1), 7-dimethylamino-5-methyl-2-methylamino-3-phenylsulfonyl-pyrazolo[1,5-a]pyrimidine 1.2.12(2), 7-(2-dimethylamino)ethylamino-5-methyl-2-methylamino-3-phenylsulfonyl-pyrazolo[1,5-a]pyrimidine 1.2.12(3), 5-methyl-2-methylamino-7-(4-methylpiperidin-1-yl)-3-phenylsulfonyl-pyrazolo[1,5-a]pyrimidine 1.2.12(4), 5-methyl-2-methylamino-7-(morfolin-4-yl)-3-phenylsulfonyl-pyrazolo[1,5-a]pyrimidine 1.2.12(5), 7-[(2-dimethylaminoethyl)-methylamino]-2-methylamino-5-phenyl-3-phenylsulfonyl-pyrazolo[1,5-a]pyrimidine 1.2.12(6), 7-(2-dimethylaminoethyl)-amino-2-methylamino-3-phenylsulfonyl-5-(furan-2-yl)-pyrazolo[1,5-a]pyrimidine 1.2.12(7), 7-dimethylamino-2-methylamino-5-(pyridin-2-yl)-3-phenylsulfonyl-pyrazolo[1,5-a]pyrimidine 1.2.12(8), 7-dimethylamino-2-methylamino-5-(pyridin-3-yl)-3-phenylsulfonyl-pyrazolo[1,5-a]pyrimidine 1.2.12(9), 7-dimethylamino-2-methylamino-5-(pyridin-4-yl)-3-phenylsulfonyl-pyrazolo[1,5-a]pyrimidine 1.2.12(10) and pharmaceutically acceptable salts and/or hydrates thereof.

The preferred substituted 2-alkylamino-3-arylsulfonyl-pyrazolo[1,5-a]pyrimidines of the general formula 1.2 are the esters of the general formulas 1.2.13, 1.2.14 and 1.2.15 and pharmaceutically acceptable salts and/or hydrates thereof,

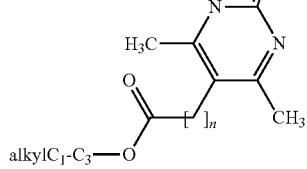

1.2.13

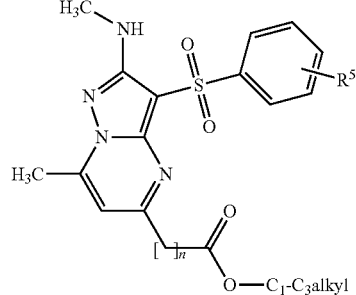

1.2.14

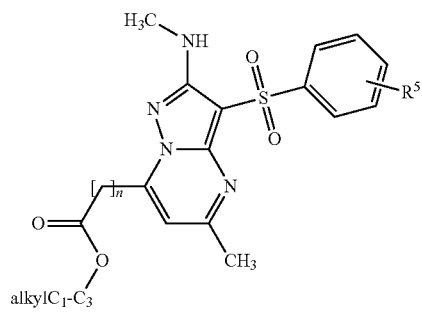

1.2.15 wherein: n and $R^5$ have the above meanings.

The preferred substituted 2-alkylamino-3-arylsulfonyl-pyrazolo[1,5-a]pyrimidines of the general formula 1.2 are the acids of the general formulas 1.2.16, 1.2.17 and 1.2.18 and pharmaceutically acceptable salts and/or hydrates thereof,

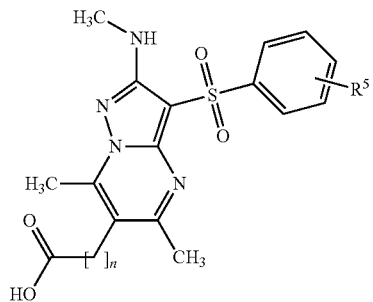

1.2.16

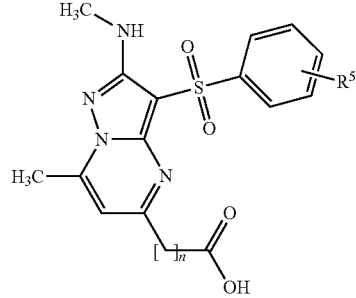

1.2.17

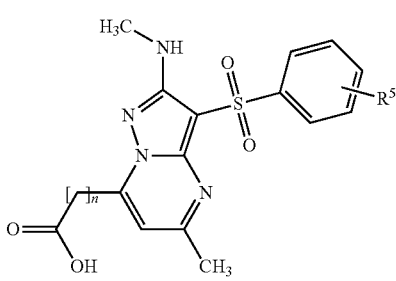

1.2.18 wherein: n and $R^5$ have the above meanings.

The preferred substituted 2-alkylamino-3-arylsulfonyl-pyrazolo[1,5-a]pyrimidines of the general formula 1.2 are the amides of the general formulas 1.2.19, 1.2.20 and 1.2.21 and pharmaceutically acceptable salts and/or hydrates thereof,

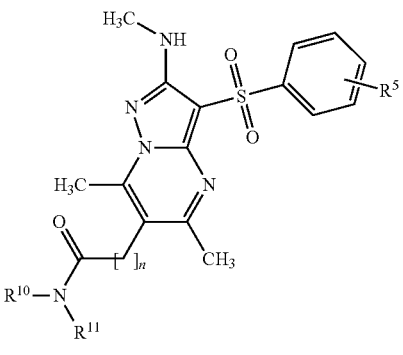

1.2.19

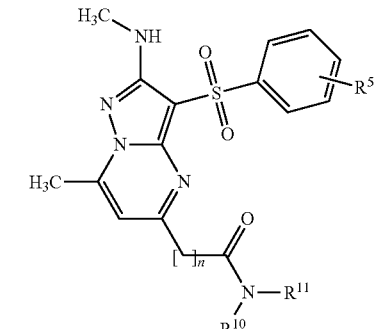

1.2.20

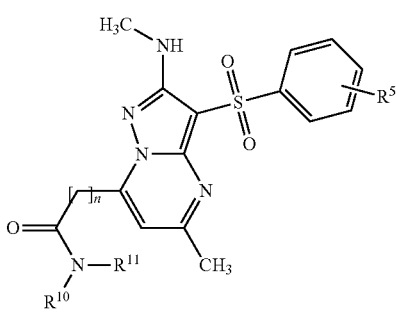

1.2.21 wherein: n, $R^5$, $R^{10}$ and $R^{11}$ have the above meanings.

The preferred substituted 2-alkylamino-3-arylsulfonyl-pyrazolo[1,5-a]pyrimidines of the general formula 1.2 are the diamines of the general formulas 1.2.22, 1.2.23 or 1.2.24 and pharmaceutically acceptable salts and/or hydrates thereof, 1.2.22

1.2.23

1.2.24 wherein: n, $R^5$, $R^{10}$ and $R^{11}$ have the above meanings.

The preferred diamines of the general formulas 1.2 and 1.2.22 are the compounds selected from the group consisting of: 6-amino-5,7-dimethyl-2-methylamino-3-phenylsulfonyl-pyrazolo[1,5-a]pyrimidine 1.2.22(1), 6-aminomethyl-5,7-dimethyl-2-methylamino-3-phenylsulfonyl-pyrazolo[1,5-a]pyrimidine 1.2.22(2), 6-(2-aminoethyl)-5,7-dimethyl-2-methylamino-3-phenylsulfonyl-pyrazolo[1,5-a]pyrimidine 1.2.22(3), 6-(3-aminopropyl)-5,7-dimethyl-2-methylamino-3-phenylsulfonyl-pyrazolo[1,5-a]pyrimidine 1.2.22(4), 6-(aminomethyl)-5,7-dimethyl-2-methylamino-3-(3-chlorophenylsulfonyl)-pyrazolo[1,5-a]pyrimidine 1.2.22(5), 6-(aminomethyl)-5,7-dimethyl-2-methylamino-3-(3-fluorophenylsulfonyl)-pyrazolo[1,5-a]pyrimidine 1.2.22(6), 6-(aminomethyl)-5,7-dimethyl-2-methylamino-3-(4-fluoro-3-chlorophenylsulfonyl)-pyrazolo[1,5-a]pyrimidine 1.2.22(7), 6-(2-aminoethyl)-5,7-dimethyl-2-methylamino-3-(3-chlorophenylsulfonyl)-pyrazolo[1,5-a]pyrimidine 1.2.22(8), 6-(2-aminoethyl)-5,7-dimethyl-2-methylamino-3-(3-fluorophenylsulfonyl)-pyrazolo[1,5-a]pyrimidine 1.2.22(9), 5,7-dimethyl-6-(dimethylaminomethyl)-2-methylamino-3-phenylsulfonyl-pyrazolo[1,5-a]pyrimidine 1.2.22(10), 5,7-dimethyl-6-(dimethylaminomethyl)-2-methylamino-3-(3-chlorophenylsulfonyl)-pyrazolo[1,5-a]pyrimidine 1.2.22(11), 5,7-dimethyl-6-(dimethylaminomethyl)-2-methylamino-3-(3-fluorophenylsulfonyl)-pyrazolo[1,5-a]pyrimidine 1.2.22(12), 5,7-dimethyl-6-(dimethylaminomethyl)-2-methylamino-3-(4-fluoro-3-chlorophenylsulfonyl)-pyrazolo[1,5-a]pyrimidine 1.2.22(13), 5,7-dimethyl-6-(2-dimethylamino)ethyl-2-methylamino-3-phenylsulfonyl-pyrazolo[1,5-a]pyrimidine 1.2.22(14), 5,7-dimethyl-6-(2-dimethylamino)ethyl-2-methylamino-3-(3-chlorophenylsulfonyl)-pyrazolo[1,5-a]pyrimidine 1.2.22(15), 5,7-dimethyl-6-(2-dimethylamino)ethyl-2-methylamino-3-(3-fluorophenylsulfonyl)-pyrazolo[1,5-a]pyrimidine 1.2.22(16), 5,7-dimethyl-6-(2-dimethylamino)ethyl-2-methylamino-3-(4-fluoro-3-chlorophenylsulfonyl)-pyrazolo[1,5-a]pyrimidine 1.2.22(17) and pharmaceutically acceptable salts and/or hydrates thereof.

The preferred diamines of the general formulas 1.2 and 1.2.23 are the compounds selected from the group consisting of: 5-(aminomethyl)-5,7-dimethyl-2-methylamino-3-phenylsulfonyl-pyrazolo[1,5-a]pyrimidine 1.2.23(1), 5-(aminomethyl)-5,7-dimethyl-2-methylamino-3-(4-fluorophenylsulfonyl)-pyrazolo[1,5-a]pyrimidine 1.2.23(2), 5-(2-aminoethyl)-5,7-dimethyl-2-methylamino-3-phenylsulfonyl-pyrazolo[1,5-a]pyrimidine 1.2.23(3), 5-(3-aminopropyl)-5,7-dimethyl-2-methylamino-3-phenylsulfonyl-pyrazolo[1,5-a]pyrimidine 1.2.23(4), 5-(aminomethyl)-5,7-dimethyl-2-methylamino-3-(3-chlorophenylsulfonyl)-pyrazolo[1,5-a]pyrimidine 1.2.23(5), 5-(aminomethyl)-5,7-dimethyl-2-methylamino-3-(3-fluorophenylsulfonyl)-pyrazolo[1,5-a]pyrimidine 1.2.23(6), 5-(aminomethyl)-5,7-dimethyl-2-methylamino-3-(4-fluoro-3-chlorophenylsulfonyl)-pyrazolo[1,5-a]pyrimidine 1.2.23(7), 5-(2-aminoethyl)-5,7-dimethyl-2-methylamino-3-(3-chlorophenylsulfonyl)-pyrazolo[1,5-a]pyrimidine 1.2.23(8), 5-(2-aminoethyl)-5,7-dimethyl-2-methylamino-3-(3-fluorophenylsulfonyl)-pyrazolo[1,5-a]pyrimidine 1.2.23(9), 5,7-dimethyl-5-(dimethylaminomethyl)-2-methylamino-3-phenylsulfonyl-pyrazolo[1,5-a]pyrimidine 1.2.23(10), 5,7-dimethyl-5-(dimethylaminomethyl)-2-methylamino-3-(3-chlorophenylsulfonyl)-pyrazolo[1,5-a]pyrimidine 1.2.23(11), 5,7-dimethyl-5-(dimethylaminomethyl)-2-methylamino-3-(3-fluorophenylsulfonyl)-pyrazolo[1,5-a]pyrimidine 1.2.23(12), 5,7-dimethyl-5-(dimethylaminomethyl)-2-methylamino-3-(4-fluoro-3-chlorophenylsulfonyl)-pyrazolo[1,5-a]pyrimidine 1.2.23(13), 5,7-dimethyl-5-(2-dimethylamino)ethyl-2-methylamino-3-phenylsulfonyl-pyrazolo[1,5-a]pyrimidine 1.2.23(14), 5,7-dimethyl-5-(2-dimethylamino)ethyl-2-methylamino-3-(3-chlorophenylsulfonyl)-pyrazolo[1,5-a]pyrimidine 1.2.23(15), 5,7-dimethyl-5-(2-dimethylamino)ethyl-2-methylamino-3-(3-fluorophenylsulfonyl)-pyrazolo[1,5-a]pyrimidine 1.2.23(16), 5,7-dimethyl-5-(2-dimethylamino)ethyl-2-methylamino-3-(4-fluoro-3-chlorophenylsulfonyl)-pyrazolo[1,5-a]pyrimidine 1.2.23(17) and pharmaceutically acceptable salts and/or hydrates thereof.

The preferred diamines of the general formulas 1.2 and 1.2.24 are the compounds selected from the group consisting of: 7-(aminomethyl)-5,7-dimethyl-2-methylamino-3-phenylsulfonyl-pyrazolo[1,5-a]pyrimidine 1.2.24(1), 7-(aminomethyl)-5,7-dimethyl-2-methylamino-3-(4-fluorophenylsulfonyl)-pyrazolo[1,5-a]pyrimidine 1.2.24(2), 7-(2-aminoethyl)-5,7-dimethyl-2-methylamino-3-phenylsulfonyl-pyrazolo[1,5-a]pyrimidine 1.2.24(3), 7-(3-aminopropyl)-5,7-dimethyl-2-methylamino-3-phenylsulfonyl-pyrazolo[1,5-a]pyrimidine 1.2.24(4), 7-(aminomethyl)-5,7-dimethyl-2-methylamino-3-(3-chlorophenylsulfonyl)-pyrazolo[1,5-a]pyrimidine 1.2.24(5), 7-(aminomethyl)-5,7-dimethyl-2-methylamino-3-(3-fluorophenylsulfonyl)-pyrazolo[1,5-a]pyrimidine 1.2.24(6), 7-(aminomethyl)-5,7-dimethyl-2-methylamino-3-(4-fluoro-3-chlorophenylsulfonyl)-pyrazolo[1,5-a]pyrimidine 1.2.24(7), 7-(2-aminoethyl)-5,7-dimethyl-2-methylamino-3-(3-chlorophenylsulfonyl)-pyrazolo[1,5-a]pyrimidine 1.2.24(8), 7-(2-aminoethyl)-5,7-dimethyl-2-methylamino-3-(3-fluorophenylsulfonyl)-pyrazolo[1,5-a]pyrimidine 1.2.24(9), 5,7-dimethyl-7-(dimethylaminomethyl)-2-methylamino-3-phenylsulfonyl-pyrazolo[1,5-a]pyrimidine 1.2.24(10), 5,7-dimethyl-7-(dimethylaminomethyl)-2-methylamino-3-(3-chlorophenylsulfonyl)-pyrazolo[1,5-a]pyrimidine 1.2.24(11), 5,7-dimethyl-7-(dimethylaminomethyl)-2-methylamino-3-(3-fluorophenylsulfonyl)-pyrazolo[1,5-a]pyrimidine 1.2.24(12), 5,7-dimethyl-7-(dimethylaminomethyl)-2-methylamino-3-(4-fluoro-3-chlorophenylsulfonyl)-pyrazolo[1,5-a]pyrimidine 1.2.24(13), 5,7-dimethyl-7-(2-dimethylamino)ethyl-2-methylamino-3-phenylsulfonyl-pyrazolo[1,5-a]pyrimidine 1.2.24(14), 5,7-dimethyl-7-(2-dimethylamino)ethyl-2-methylamino-3-(3-chlorophenylsulfonyl)-pyrazolo[1,5-a]pyrimidine 1.2.24(15), 5,7-dimethyl-7-(2-dimethylamino)ethyl-2-methylamino-3-(3-fluorophenylsulfonyl)-pyrazolo[1,5-a]pyrimidine 1.2.24(16), 5,7-dimethyl-7-(2-dimethylamino)ethyl-2-methylamino-3-(4-fluoro-3-chlorophenylsulfonyl)-pyrazolo[1,5-a]pyrimidine 1.2.24(17) and pharmaceutically acceptable salts and/or hydrates thereof.

The subject of the present invention is a method for the preparation of substituted 3-arylsulfonyl-pyrazolo[1,5-a]pyrimidines of the general formula 1 and pharmaceutically acceptable salts and/or hydrates thereof by interaction of 3-amino-4-sulfonyl-2H-pyrazoles of the general formula 2 with the corresponding β-diketones of the general formula 3 and subsequent isolation or separation of the reaction products (A, B) according to the scheme given below. In the case of symmetrically substituted β-diketones of the general formula 3, where $R^1=R^3$, only one substituted 2-alkylamino-3-arylsulfonyl-pyrazolo[1,5-a]pyrimidine, 1A=1B, is formed. If nonsymmetrically substituted β-diketones ($R^1 \neq R^3$) of the general formula 3 are employed, a mixture of two isomeric 2-alkylamino-3-arylsulfonyl-pyrazolo[1,5-a]pyrimidines 1A and 1B is usually obtained which is separated by crystallization or by means of chromatography,

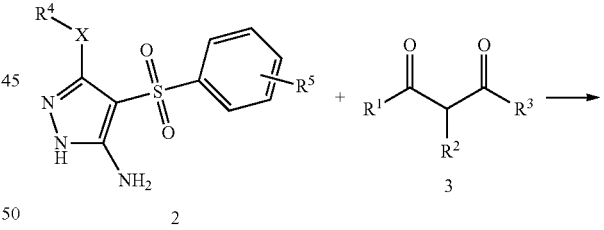

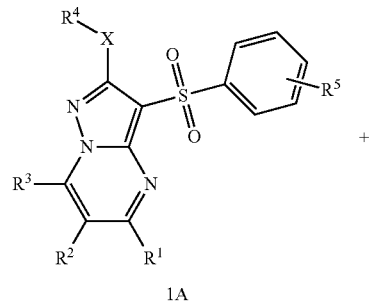

1A

-continued

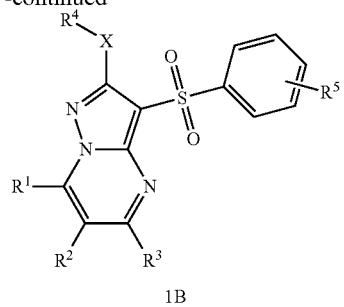

1B wherein: $R^1$, $R^2$, $R^3$, $R^4$ and $R^5$ have the above meanings.

The subject of the present invention is a method for the preparation of substituted 2-sulfinyl-3-arylsulfonyl-pyrazolo[1,5-a]pyrimidines of the general formula 1, where X=SO, by oxidation of 2-sulfanyl-3-arylsulfonyl-pyrazolo[1,5-a]pyrimidines of the general formula 1 where X=S according to the scheme given below,

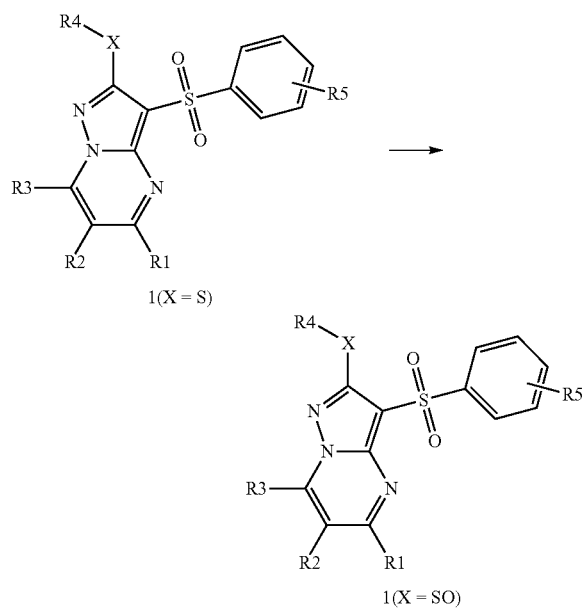

wherein: $R^1$, $R^2$, $R^3$, $R^4$ and $R^5$ have the above meanings.

The subject of the present invention is also a method for the preparation of substituted 3-arylsulfonyl-pyrazolo[1,5-a]pyrimidines of the general formulas 1.1.1, 1.2.1 by interaction of 3-amino-4-sulfonyl-2H-pyrazoles of the general formula 2 with tetraacetales of malonic aldehyde 3.1 according to the scheme given below,

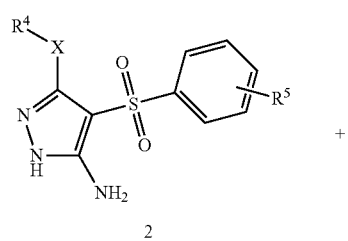

-continued

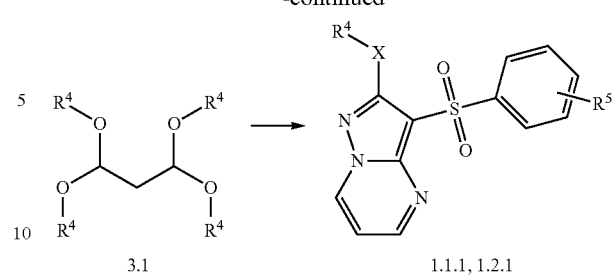

wherein: X, $R^4$ and $R^5$ have the above meanings.

The subject of the present invention is also a method for the preparation of substituted 3-arylsulfonyl-pyrazolo[1,5-a]pyrimidines of the general formulas 1.1.2, 1.2.2 by the reduction of chloro-derivatives of the general formula 4,

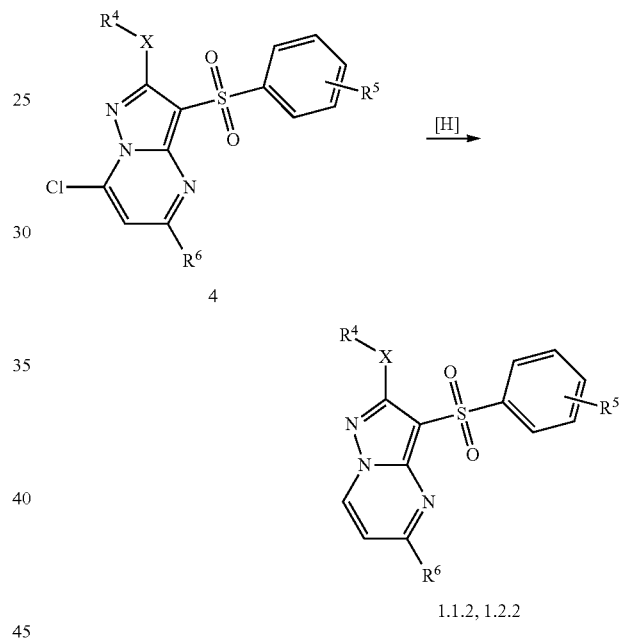

wherein: X, $R^4$, $R^5$ and $R^6$ have the above meanings.

The subject of the present invention is also a method for the preparation of substituted 3-arylsulfonyl-pyrazolo[1,5-a]pyrimidines of the general formulas 1.1.2, 1.1.3, 1.2.2, 1.2.3 by interaction of 3-amino-4-sulfonyl-2H-pyrazoles of the general formula 2 with 1-substituted 3,3-dialkyloxy-propanone 3.2 and subsequent isolation or separation of the reaction products according to the scheme given below,

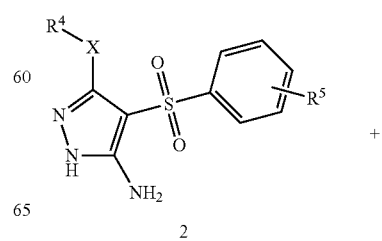

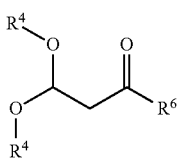

3.2

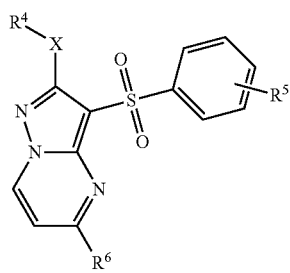

1.1.2, 1.2.2

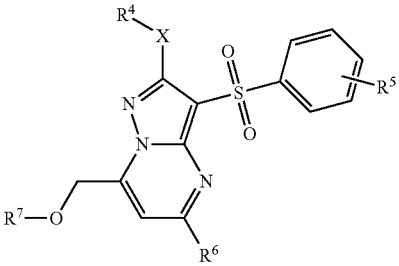

1.1.4, 1.2.4

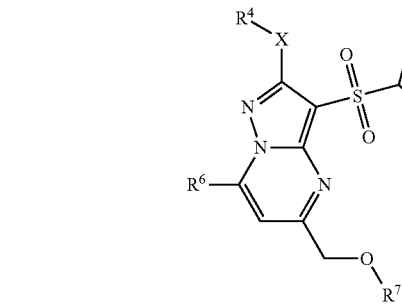

1.1.5, 1.2.5 wherein: X, R⁴, R⁵, R⁶ and R⁷ have the above meanings.

The subject of the present invention is also a method for the preparation of substituted 7-hydroxymethyl-3-arylsulfonyl-pyrazolo[1,5-a]pyrimidines of the general formulas 1.1.6, 1.2.6 by the action of boron tribromide on 3-arylsulfonyl-pyrazolo[1,5-a]pyrimidines of the general formula 1.1.4, 1.2.4 according to the scheme given below,

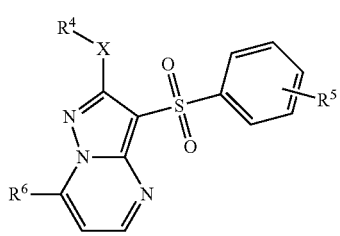

1.1.3, 1.2.3 wherein: X, R⁴, R⁵ and R⁶ have the above meanings.

The subject of the present invention is also a method for the preparation of alkyloxysubstituted 3-arylsulfonyl-pyrazolo[1,5-a]pyrimidines of the general formulas 1.1.4, 1.1.5, 1.2.4, 1.2.5 by interaction of 3-amino-4-sulfonyl-2H-pyrazoles of the general formula 2 with 1-methoxy-pentan-2,4-dione 3.3 and subsequent isolation or separation of the reaction products according to the scheme given below,

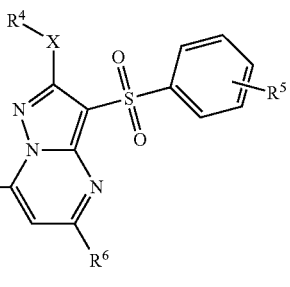

1.1.4, 1.2.4

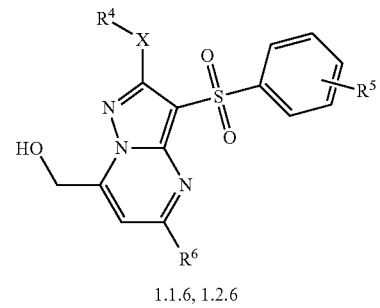

1.1.6, 1.2.6 wherein: X, R⁴, R⁵, R⁶ and R⁷ have the above meanings.

The subject of the present invention is also a method for the preparation of substituted 3-arylsulfonyl-5-hydroxymethyl-pyrazolo[1,5-a]pyrimidines of the general formulas 1.1.7, 1.2.7 by the action of boron tribromide on 3-arylsulfonyl-pyrazolo[1,5-a]pyrimidines of the general formulas 1.1.5, 1.2.5 according to the scheme given below,

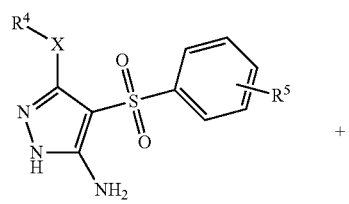

2

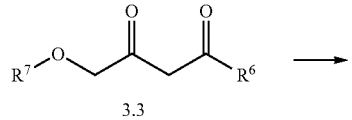

3.3

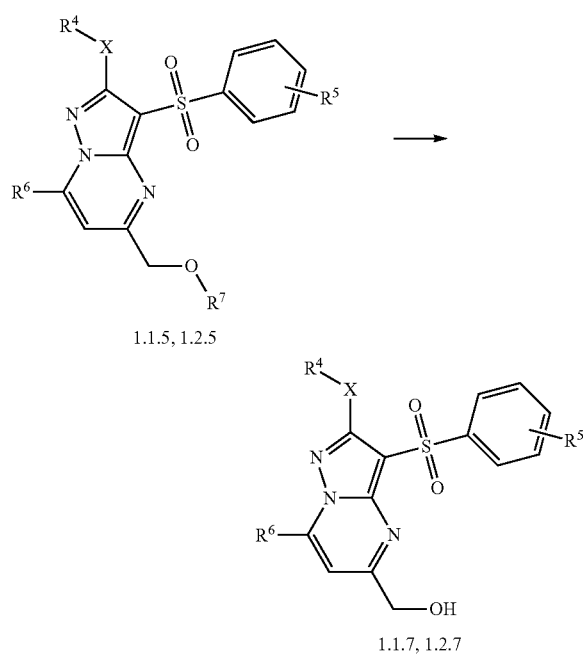

1.1.5, 1.2.5

1.1.7, 1.2.7 wherein: X, $R^4$, $R^5$, $R^6$ and $R^7$ have the above meanings.

The subject of the present invention is also a method for the preparation of substituted 3-arylsulfonyl-pyrazolo[1,5-a]pyrimidines of the general formulas 1.1.8, 1.2.10 by interaction of chloro-substituted derivatives of the general formula 4 with alkali metal alcoholates of the general formula 6,

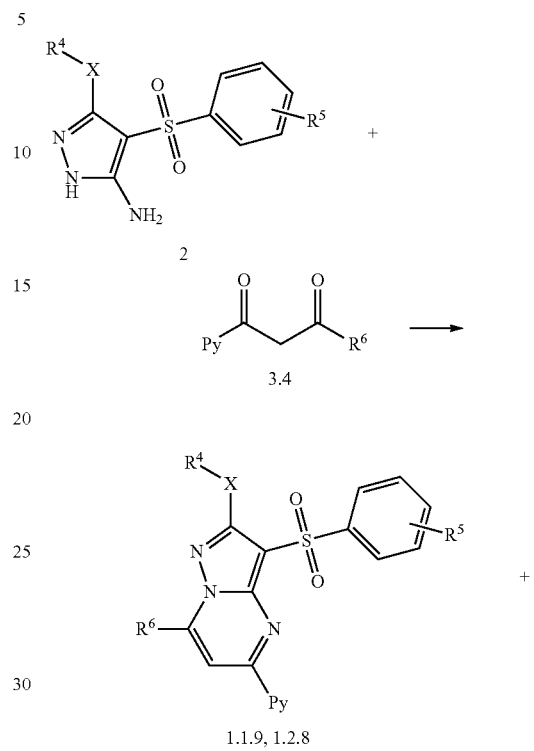

1.1.8, 1.2.10 wherein: X, $R^4$, $R^5$, $R^8$ and $R^9$ have the above meanings; M represents alkali metal cation.

The subject of the present invention is also a method for the preparation of pyridyl-substituted 3-arylsulfonyl-pyrazolo[1,5-a]pyrimidines of the general formulas 1.1.9, 1.1.10, 1.2.8, 1.2.9 by interaction of 3-amino-4-arylsulfonyl-2H-pyrazoles of the general formula 2 with diketones 3.4 and subsequent isolation or separation of the reaction products according to the scheme given below,

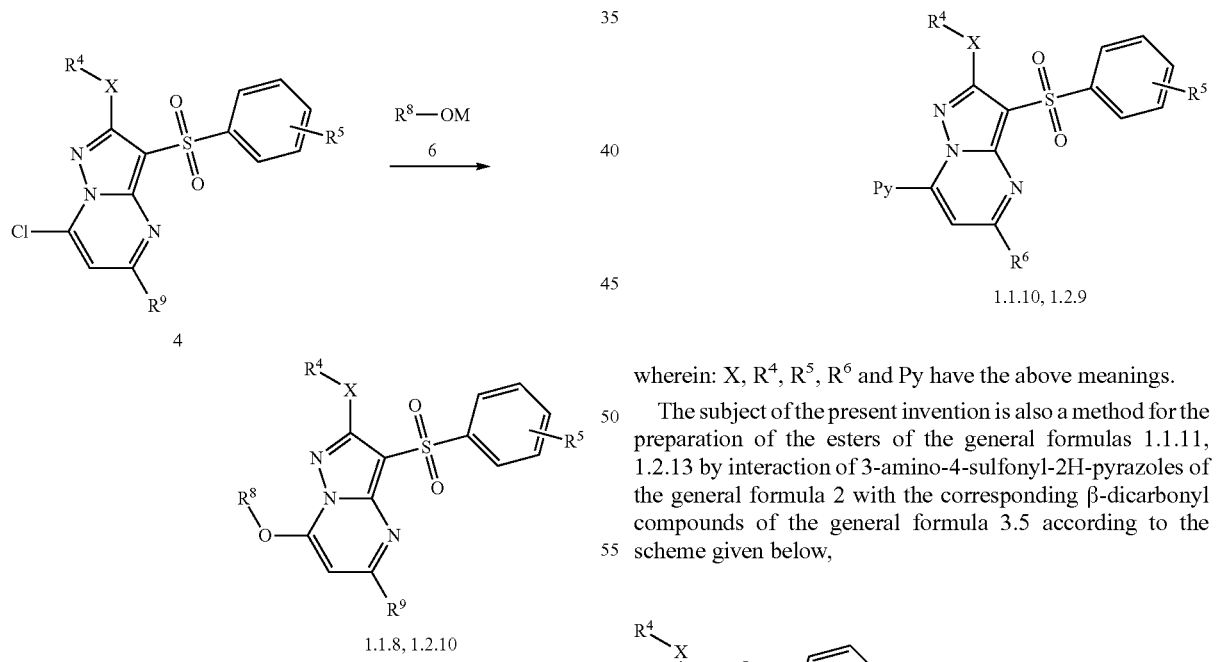

1.1.9, 1.2.8

1.1.10, 1.2.9 wherein: X, $R^4$, $R^5$, $R^6$ and Py have the above meanings.

The subject of the present invention is also a method for the preparation of the esters of the general formulas 1.1.11, 1.2.13 by interaction of 3-amino-4-sulfonyl-2H-pyrazoles of the general formula 2 with the corresponding β-dicarbonyl compounds of the general formula 3.5 according to the scheme given below,

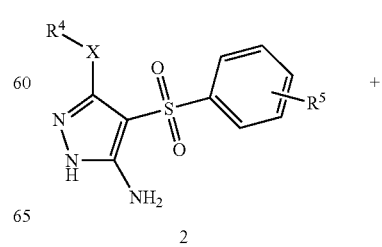

2

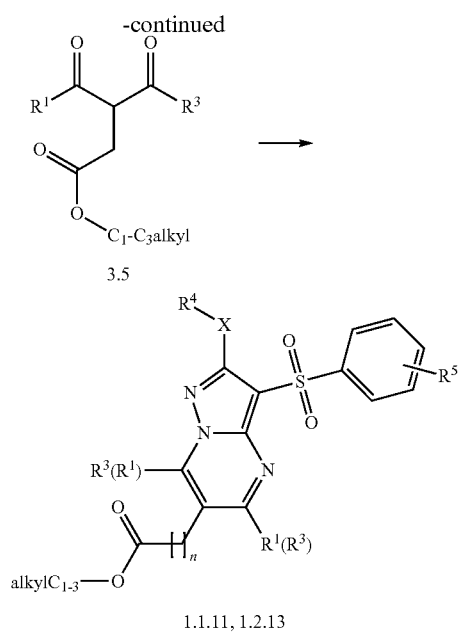

3.5

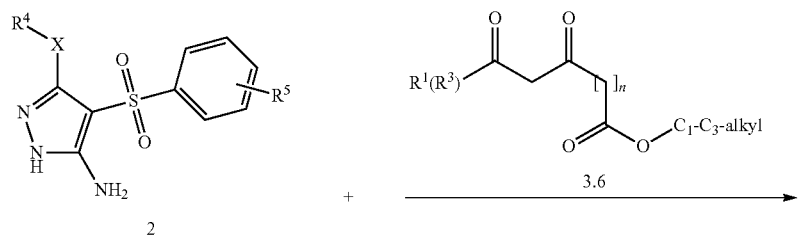

1.1.11, 1.2.13 wherein: n, X, $R^1$, $R^3$, $R^4$ and $R^5$ have the above meanings.

The subject of the present invention is also a method for the preparation of the esters of the general formulas 1.1.12, 1.1.13, 1.2.14, 1.2.15 by interaction of 3-amino-4-sulfonyl-2H-pyrazoles of the general formula 2 with the corresponding β-dicarbonyl compounds of the general formula 3.6 and subsequent isolation or separation of the reaction products according to the scheme given below,

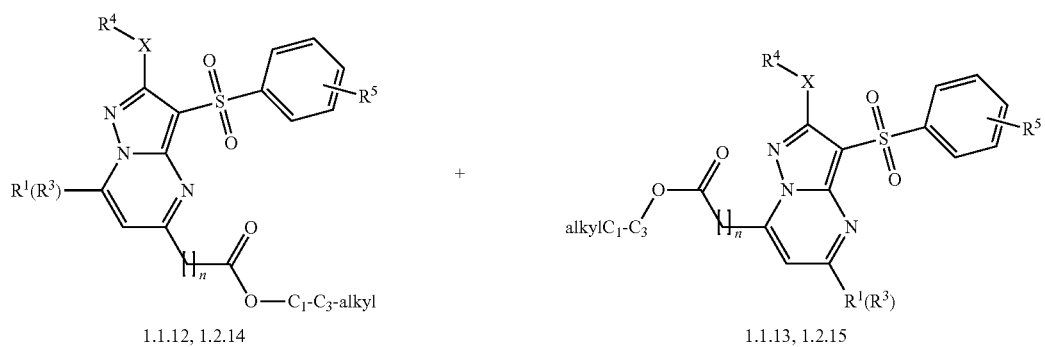

1.1.12, 1.2.14

1.1.13, 1.2.15 wherein: n, $R^1$, $R^3$, $R^4$ and $R_i^5$ have the above meanings.

The subject of the present invention is also a method for the preparation of the acids of the general formulas 1.1.14, 1.1.15, 1.1.16, 1.2.16, 1.2.17, 1.2.18 by hydrolysis of the corresponding esters of the general formulas 1.1.11, 1.1.12, 1.1.13, 1.2.13, 1.2.14, 1.2.15.

The subject of the present invention is also a method for the preparation of the amides of the general formulas 1.1.17, 1.1.18, 1.1.1.19, 1.2.19, 1.2.20, 1.2.21 by interaction of the corresponding acids of the general formulas 1.1.14, 1.1.15, 1.1.16, 1.2.16, 1.2.17, 1.2.18 or their derivatives with amines of the general formula 5,

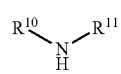

5 wherein: $R^{10}$ and $R^{11}$ have the above meanings.

The subject of the present invention is also a method for the preparation of the amides of the general formulas 1.1.17, 1.2.19 by interaction of 3-amino-4-sulfonyl-2H-pyrazoles of the general formula 2 with the corresponding β-dicarbonyl compounds of the general formula 6,

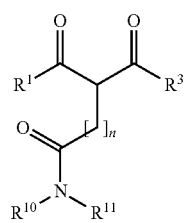

6 wherein: n, $R^1$, $R^3$, $R^{10}$ and $R^{11}$ have the above meanings.

The subject of the present invention is also a method for the preparation of amides of the general formulas 1.1.18, 1.1.1.19, 1.2.20, 1.2.21 by interaction of 3-amino-4-sulfonyl-2H-pyrazoles of the general formula 2 with the corresponding β-dicarbonyl compounds of the general formula 3.7 and subsequent isolation and purification or separation of the reaction products according to the scheme given below,

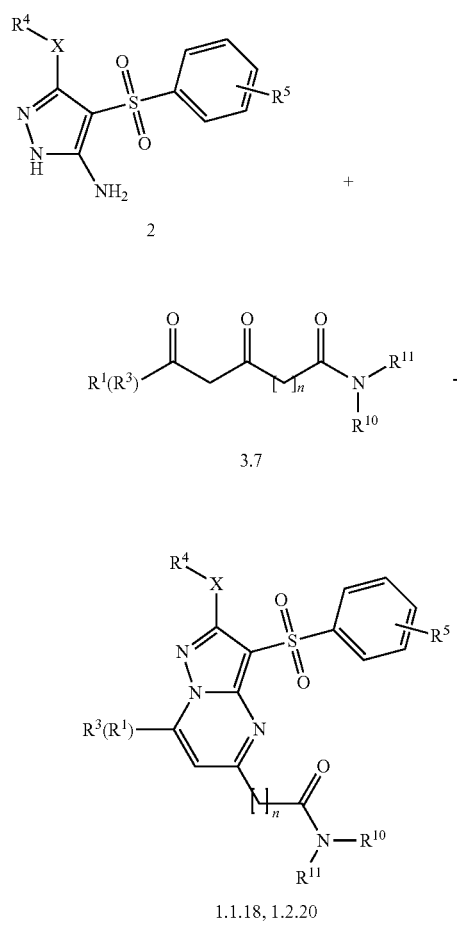

1.1.18, 1.2.20

1.1.19, 1.2.21 wherein: n, X, $R^1$, $R^3$, $R^4$, $R_1^5$, $R^{10}$ and $R^{11}$ have the above meanings.

The subject of the present invention is also a method for the preparation of the amines of the general formulas 1.1.20, 1.2.22, 1.1.21, 1.2.23, 1.1.22, 1.2.24, and pharmaceutically acceptable salts and/or hydrates thereof by consecutive transformations of the acids 1.1.14, 1.1.15, 1.1.16, 1.2.16, 1.2.17, 1.2.18 into acylazides 7.1, 7.2, 7.3, isocyanates 8.1, 8.2, 8.3, and amines 1.1.20, 1.2.22, 1.1.21, 1.2.23, 1.1.22, 1.2.24 according to the schemes given below, 1.1.14, 1.2.16 ⟶

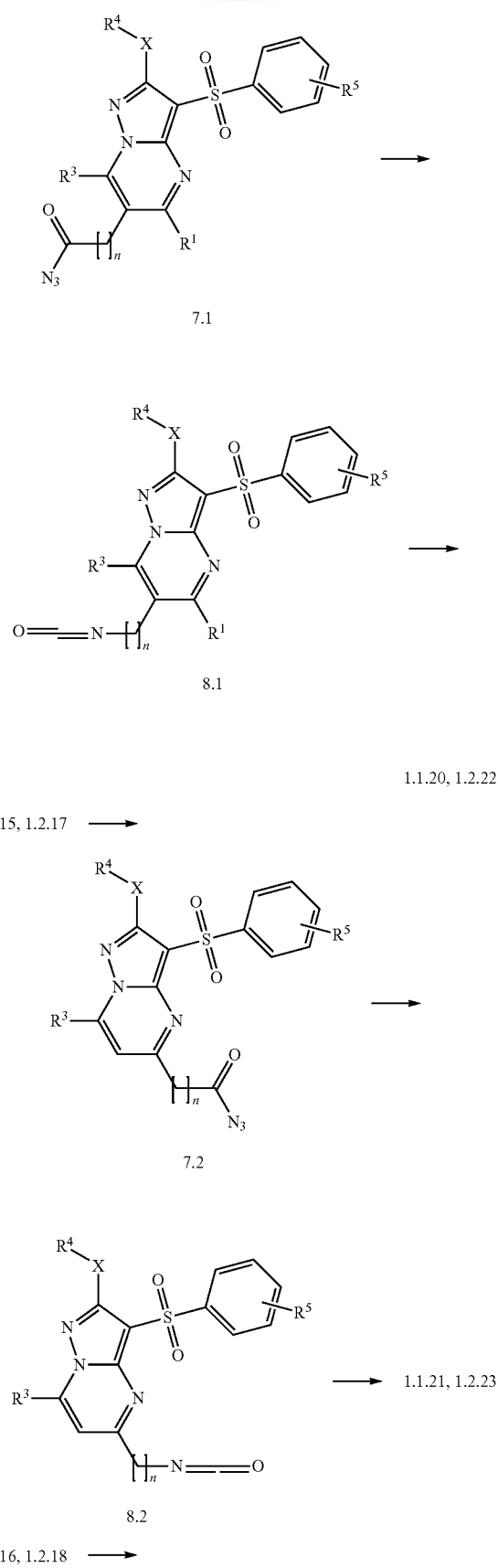

1.1.15, 1.2.17 ⟶

1.1.16, 1.2.18 ⟶

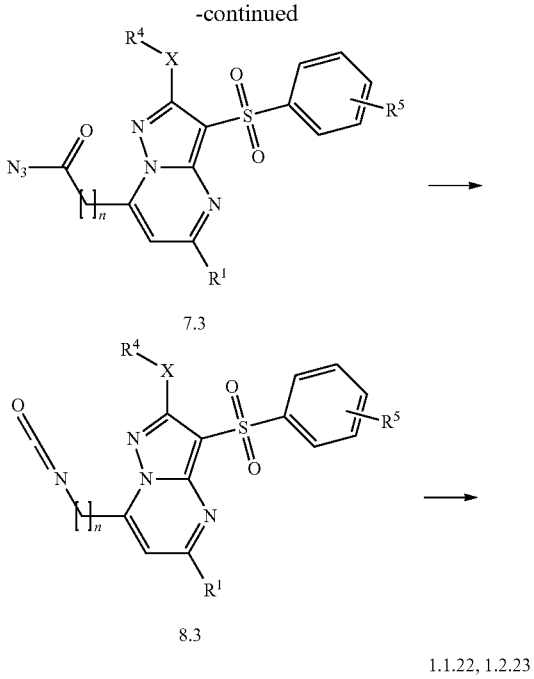

wherein: n, X, $R^1$, $R^3$, $R^4$ and $R^5$ have the above meanings.

The subject of the present invention is also a method for the preparation of the amines of the general formula 1.1.20, 1.2.22, 1.1.21, 1.2.23, 1.1.22, 1.2.24 and pharmaceutically acceptable salts and/or hydrates by reductive alkylation of the amines 1.1.20, 1.2.22, 1.1.21, 1.2.23, 1.1.22, 1.2.24, where $R^{10}=R^{11}=H$, with carbonyl compounds of the general formula 9,

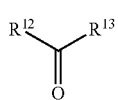

wherein: $R^{12}$ and $R^{13}$ represent hydrogen, optionally substituted $C_1$-$C_3$alkyl, optionally substituted aryl or $R^{12}$ and $R^{13}$ together with the carbon atom they are attached to form optionally substituted $C_5$-$C_7$cycloalkyl or heterocyclyl comprising one heteroatom and 4-6 carbon atoms.

The subject of the present invention is a method for the preparation of the amines of the general formula 1.1.20, 1.2.22 and pharmaceutically acceptable salts and/or hydrates thereof where concurrently (at n=0, $R^{10}=R^{11}=H$,) by hydrogenation of 6-(aryldiazenyl)-3-arylsulfonyl-pyrazolo[1,5-a]pyrimidines of the general formula 1 where $R^2$=aryldiazenyl in organic solvent or by alkaline hydrolysis of N-(3-arylsulfonyl)-pyrazolo[1,5-a]pyrimidin-6-yl)acetamides of the general formula 1, in which $R^2$=acylamino group.

The subject of the present invention is a method for the preparation of the amines of the general formulas 1.1.20, 1.2.22 and pharmaceutically acceptable salts and/or hydrates thereof where simultaneously n=0, $R^{10}=R^{11}=C_1$-$C_3$-alkyl by alkylation of the amines of general formulas 1.1.20, 1.2.22, where concurrently n=0, $R^{10}=R^{11}=H$.

The subject of the present invention is also serotonin 5-HT$_6$ receptor antagonists representing 3-arylsulfonyl-pyrazolo[1,5-a]pyrimidines of the general formula 1.

The subject of the present invention is also "molecular tools" for investigation of peculiarities of physiologically active compounds possessing the property to interact with serotonin 5-HT$_6$ receptors representing 3-arylsulfonyl-pyrazolo[1,5-a]pyrimidines of the general formula 1.

The subject of the present invention is also a pharmaceutical composition for prophylaxis and treatment of various conditions and diseases of CNS at humans and warm-blooded animals, comprising pharmaceutically effective amount of 3-arylsulfonyl-pyrazolo[1,5-a]pyrimidine of the general formula 1 or pharmaceutically acceptable salts and/or hydrate thereof.

Pharmaceutical compositions may include pharmaceutically acceptable excipients. Pharmaceutically acceptable excipients mean diluents, auxiliary agents and/or carriers applied in the sphere of pharmaceutics. According to the invention, pharmaceutical composition in addition to the drug substance of general formula 1 may include other active ingredients provided that, they do not give rise to undesirable effects, such as allergic reactions.

If needed, according to the present invention pharmaceutical compositions could be used in clinical practice in various forms prepared by mixing the said compositions with traditional pharmaceutical carries, for example, peroral forms (such as, tablets, gelatinous capsules, pills, solutions, or suspensions); forms for injections (such as, solutions or suspensions for injections, or a dry powder for injections, which requires only addition of water for injections before utilization); local forms (such as, ointments or solutions).

According to the present invention the carriers used in pharmaceutical compositions represent carriers, which are used in the sphere of pharmaceutics for preparation of commonly used forms. Binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The subject of the present invention is also a method for the preparation of pharmaceutical composition by mixing at least one 3-arylsulfonyl-pyrazolo[1,5-a]pyrimidine of the general formula 1 or pharmaceutically acceptable salts and/or hydrates thereof with inert exicipient and/or solvent.

The subject of the present invention is also a medicament in the form of tablets, capsules, or injections, placed in pharmaceutically acceptable packing intended for prophylaxis and treatment of cognitive disorders and neurodegenerative diseases, pathogenesis of which is associated with 5-HT$_6$ receptors, comprising pharmaceutically effective amount of at least one 3-arylsulfonyl-pyrazolo[1,5-a]pyrimidine of the general formula 1, or pharmaceutically acceptable salts and/ or hydrates thereof, or pharmaceutical composition.

The preferable medicament is a medicament in the form of tablets, capsules, or injections, placed in pharmaceutically acceptable packing, intended for prophylaxis and treatment of Alzheimer's disease, Parkinson's disease, Huntington's diseases, psychotic disorders, schizophrenia, anxious disorders, hyperkinetic disorders, for mental ability enhancing, for prophylaxis and treatment of obesity.

The subject of the present invention is also a therapeutic cocktail intended for prophylaxis and treatment of various diseases, pathogenesis of which is associated with serotonin 5-HT$_6$ receptors at humans and animals, including pharmaceutically effective amount of at least one 3-arylsulfonyl-pyrazolo[1,5-a]pyrimidine of the general formula 1, or pharmaceutically acceptable salts and/or hydrates thereof, or pharmaceutical composition.

The subject of the present invention is also a therapeutic cocktail intended for prophylaxis and treatment of neurological disorders, neurodegenerative and cognitive diseases at humans and animals, among them Alzheimer's disease, Parkinson's disease, Huntington's disease, psychotic disorders, schizophrenia, hypoxia-ischemia, hypoglycemia, convulsive states, brain injuries, lathyrism, amyotrophic lateral sclerosis, obesity or insult, including pharmaceutically effective amount of at least one 3-arylsulfonyl-pyrazolo[1,5-a]pyrimidine of the general formula 1, or pharmaceutically acceptable salts and/or hydrates thereof, or pharmaceutical composition.

Therapeutic cocktail for prophylaxis and treatment of neurological disorders, neurodegenerative and cognitive diseases at humans and animals, among them for prophylaxis and treatment of Alzheimer's disease, Parkinson's disease, Huntington's disease, psychotic disorders, schizophrenia, hypoxia-ischemia, hypoglycemia, convulsive states, brain injuries, lathyrism, amyotrophic lateral sclerosis, obesity or insult, along with the drug substances disclosed in the invention, may include other active ingredients such as: nonsteroidal anti-inflammatory drugs (Orthophene, Indomethacin, Ibuprophen and others); acetyl cholinesterase inhibitors (Tacrine, Amiridine, Fizostigmine, Aricept, Phenserine and others); estrogens (for example, Estradiol); NMDA-receptor antagonists (for example, Memantine, Neramexane); nootropic drugs (for example, Pyracetam, Fenibut and others); AMPA receptor modulators (for example, Ampalex); cannabinoid CB-1 receptor antagonists (for example, Rimonabant); monoaminooxidase inhibitors MAO-B and/or MAO-A (for example, Rasagiline); antiamyloidogenic drugs (for example, Tramiprosate); lowering β-amyloidal neurotoxicity compounds (for example, Indole-3-propionic acid); γ- and/or β-secretase inhibitors; M1-muscarinic receptor agonists (for example, Cevimeline); metal helates (for example, Clioquinol); GABA(A) receptor antagonists (for example, CGP-36742); monoclonal antibodies (for example, Bapineuzumab); antioxidants; neurotrophic agents (for example, Cerebrolisine); antidepressants (for example, Imipramine, Sertraline and others) and others.

The therapeutic cocktail for overweight lowering and obesity treatment along with the drug substances disclosed in the invention, may include other active ingredients such as: anorectic drugs (for example, Fepranon, Desopimon, Masindole), hormone drugs (for example, Tireoidine), hypolipidemic remedies, such as fibrates (for example, Fenofibrate), statines (for example, Lovastatine, Simvastatine, Pravastatine and Probucol), and also hypoglycemic drugs (sulfonylurea—for example, Butamide, Glibenclamide; biguanidines—for example, Buformine, Metamorphine), and drugs with some other mechanism of action, such as cannabinoid CB-1 receptor antagonists (Rimonabant), inhibitors of norepinephrine, and serotonin reuptake (Sibutramine), inhibitors of ferments of fatty acids synthesis (Orlistat) and others, along with antioxidants, food additives and others.

According to the present invention method for prophylaxis and treatment of various diseases, pathogenesis of which is associated with serotonin 5-$HT_6$ receptors at humans and animals, consists in introduction of novel pharmaceutical composition in the form of tablets, capsules, or injections, comprising pharmaceutically effective amount of at least one 3-arylsulfonyl-pyrazolo[1,5-a]pyrimidine of the general formula 1 or pharmaceutically acceptable salts and/or hydrates thereof.

Clinical dose of pharmaceutical composition comprising an effective amount of at least one 3-arylsulfonyl-pyrazolo[1,5-a]pyrimidine of the general formula 1, or pharmaceutically acceptable salts and/or hydrates thereof, or pharmaceutical composition, comprising pharmaceutically effective amount of at least one 3-arylsulfonyl-pyrazolo[1,5-a]pyrimidine of the general formula 1 or pharmaceutically acceptable salts and/or hydrates thereof, may be corrected depending on: therapeutic efficiency and bio-accessibility of active ingredients in patients' organism, rate of their exchange and removal from organism, and age, gender, and severity of patient's symptoms. Thus, the daily intake for adults is normally being 10~500 mg, preferably 50~300 mg. Therefore the above effective doses are to be taken into consideration while preparing pharmaceutical compositions in the form of dose unit according to the present invention; each dose unit of medicament should contain 10~500 mg of at least one 3-arylsulfonyl-pyrazolo[1,5-a]pyrimidine of the general formula 1 or pharmaceutically acceptable salts and/or hydrates thereof. Following the instructions of physician or pharmacist, the medicaments may be taken several times over specified periods of time (preferably, from one to six times).

BEST EMBODIMENT OF THE INVENTION

The invention is illustrated by the following figures.

FIG. 1 The latent period of first entries into the dark arms in 24 hours after training of rats to avoid entering the dark arms in the shuttle chamber (average value±standard error). The number in brackets is a dose of tested compound in mg/kg. The tested compounds 1.2.7(1), 1.2.22(1) and 1.2.22(18) were injected 60 minutes before the test. The difference from the group of animals received Scopolamine: *—$p<0.05$; —$p<0.01$; *—$p<0.001$.

Figure 2:
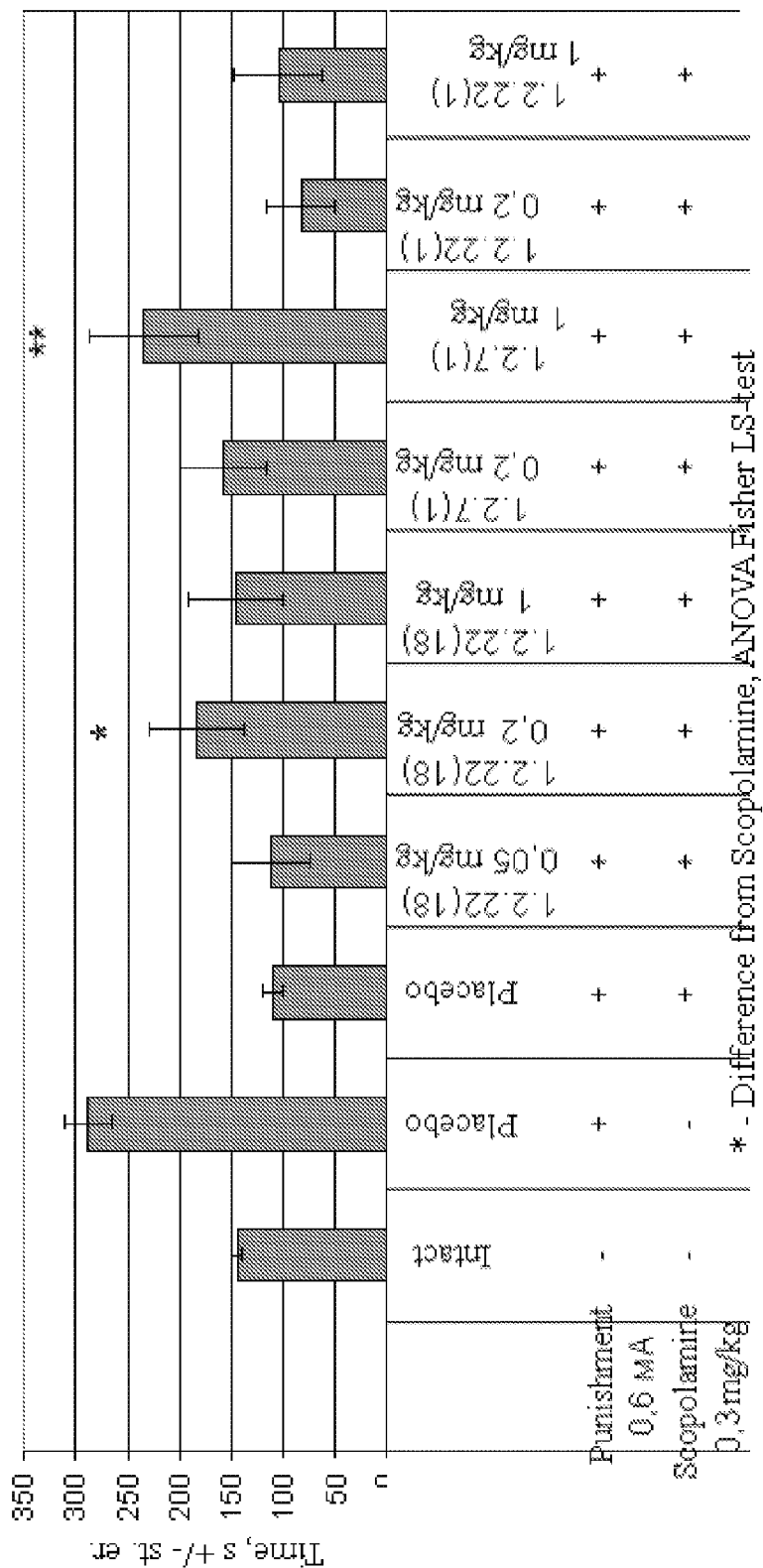

FIG. 2 Duration of light arm stays in 24 hours after training of rats to avoid dark arms in the shuttle chamber (average value±standard error). The number in brackets is a dose of tested compound in mg/kg. The tested compounds 1.2.7(1), 1.2.22(1) and 1.2.22(18) were injected 60 minutes before the test. Difference from the group of animals received Scopolamine: *—$p<0.05$; —$p<0.01$; *—$p<0.001$.

Figure 3:
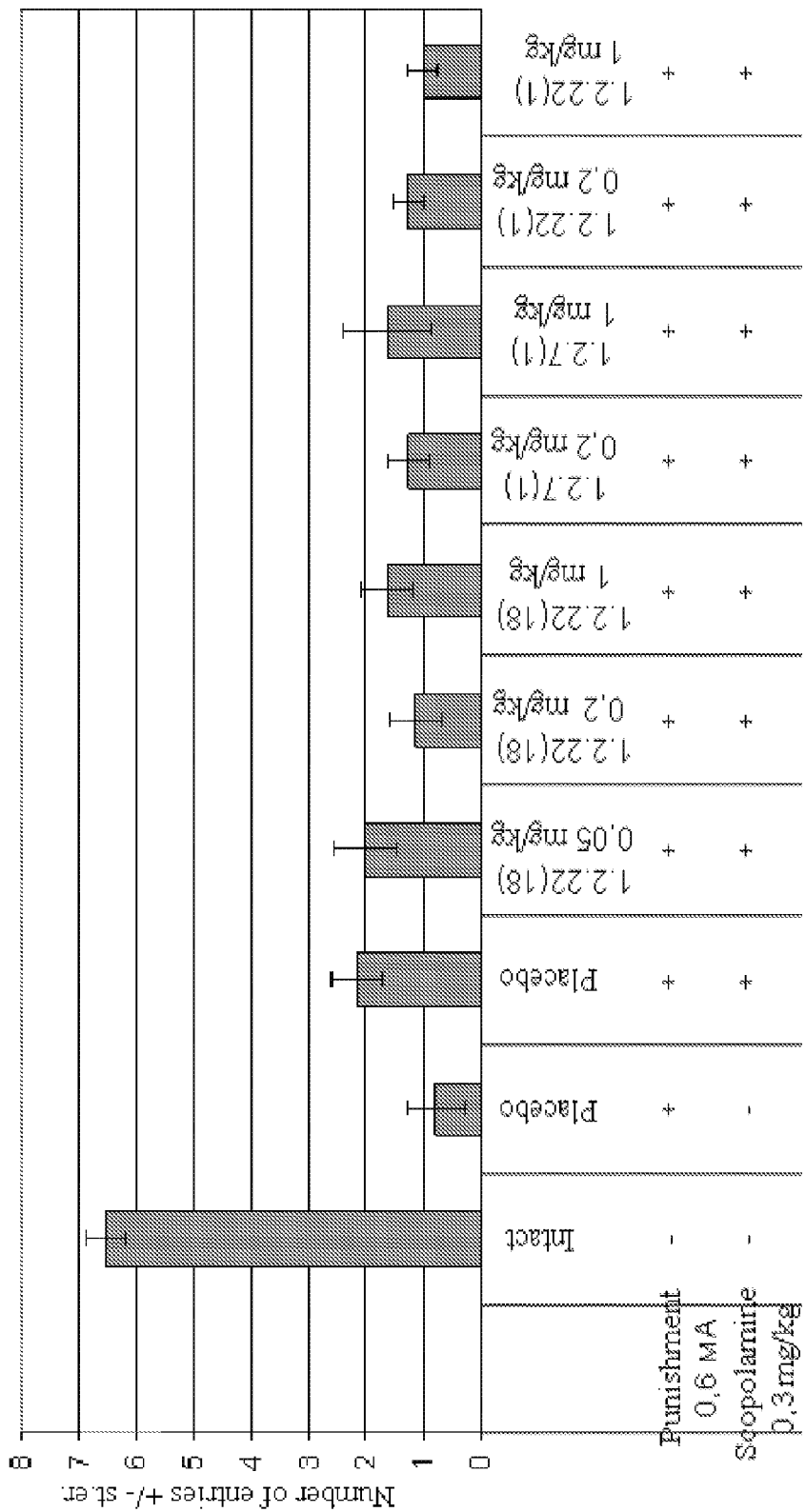

FIG. 3 The number of dark arm entries in 24 hours after training of rats to avoid dark arms in the shuttle chamber (average value±standard error). The number in brackets is a dose of tested compound in mg/kg. The tested compounds 1.2.7(1), 1.2.22(1) and 1.2.22(18) were injected 60 minutes before the test. The difference from the group of animals received Scopolamine: *—$p<0.05$; *** $p<0.001$.

Figure 4:
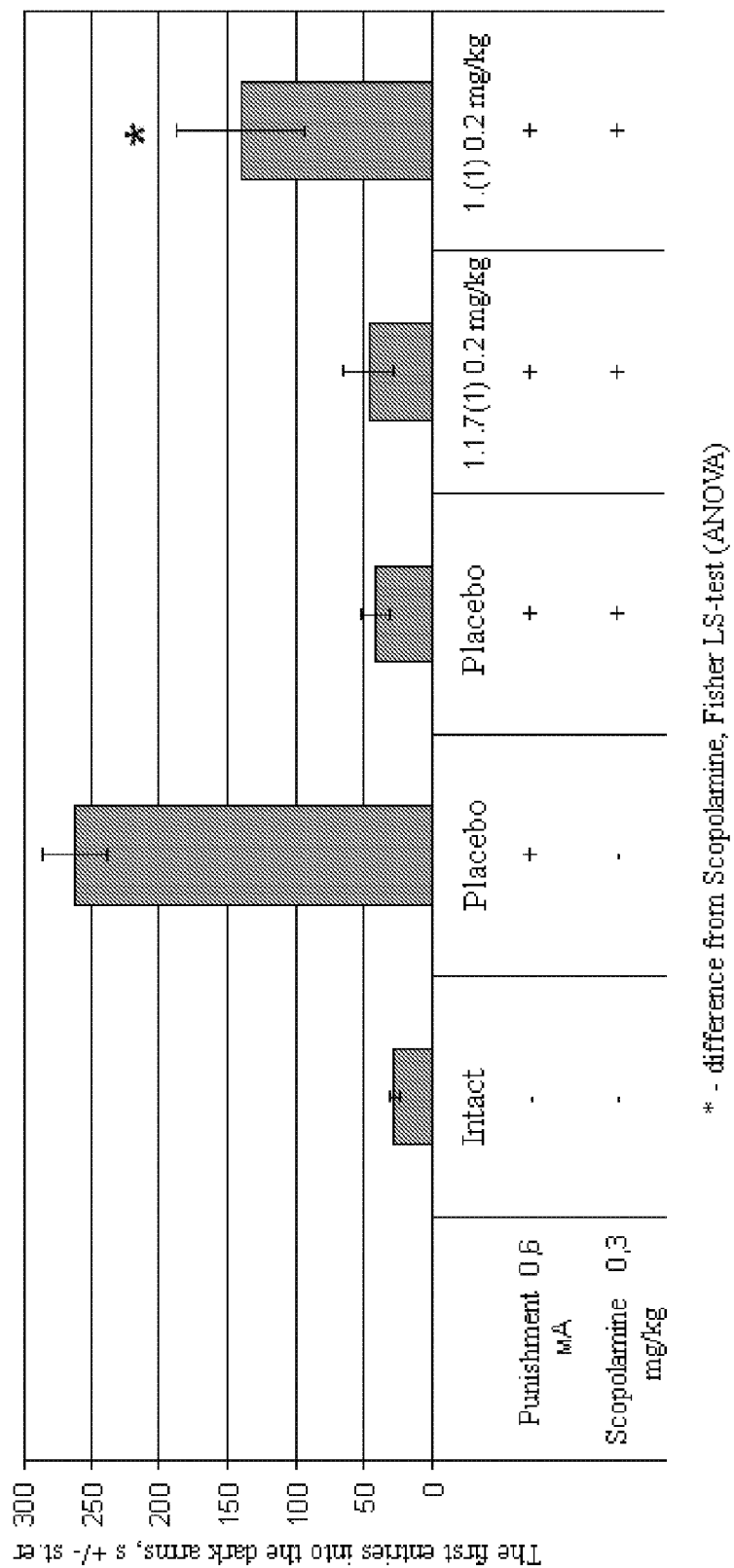

FIG. 4 The latent period of first entries into the dark arms in 24 hours after training of mice to avoid entering the dark arms in the shuttle chamber (average value±standard error). The number in brackets is a dose of compounds 1(1) and 1.1.7(1) in mg/kg. The tested compounds 1(1) and 1.1.7(1) were injected 30 minutes before the test. The difference from the group of animals received Scopolamine: *—$p<0.05$; —$p<0.01$; *—$p<0.001$.

Figure 5:
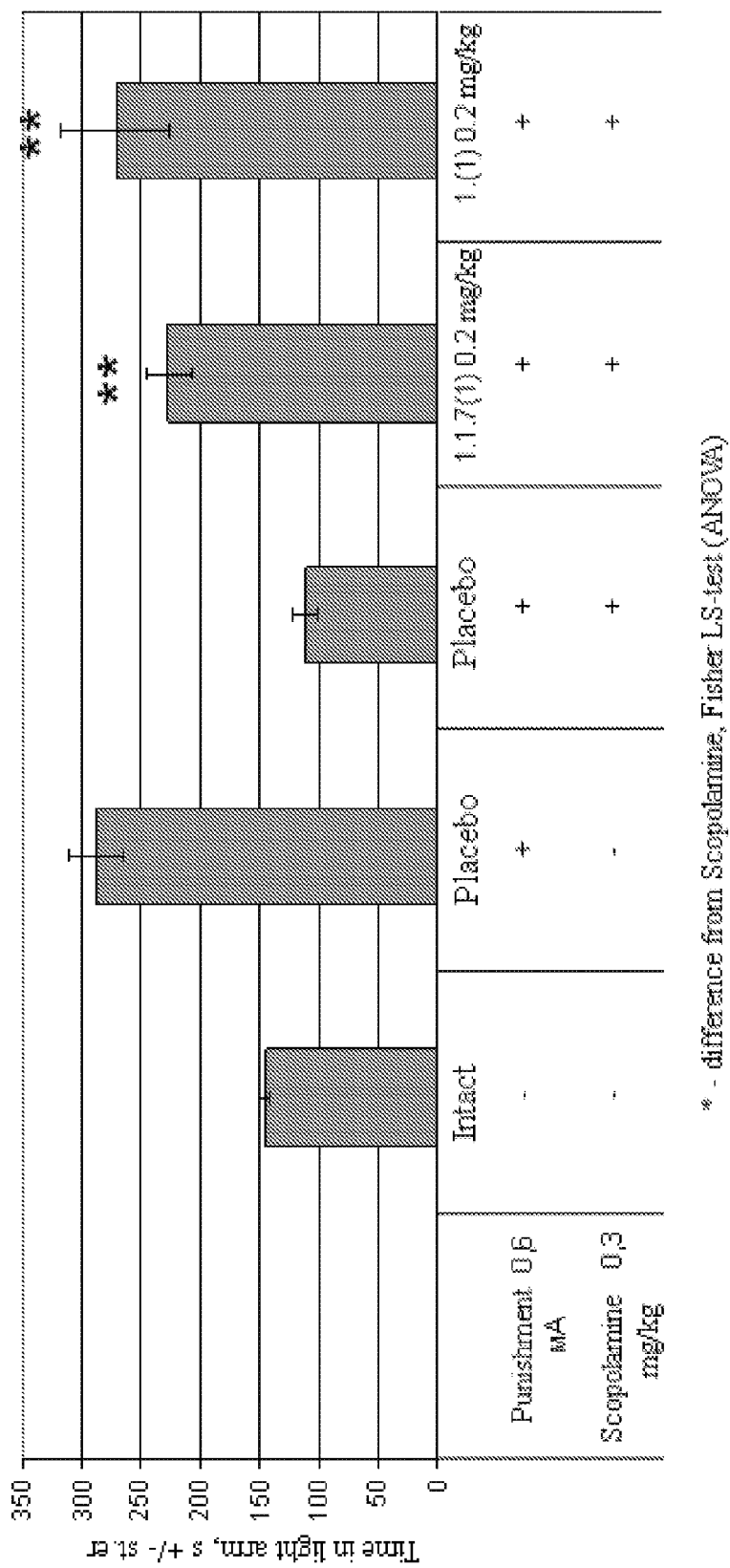

FIG. 5 Duration of light arm stays in 24 hours after training of mice to avoid dark arms in the shuttle chamber (average value±standard error). The number in brackets is a dose of tested compound in mg/kg. The tested compounds 1(1) and 1.1.7(1) were injected 30 minutes before the test. The difference from the group of animals received Scopolamine: *—$p<0.05$; —$p<0.01$; *—$p<0.001$.

Figure 6:
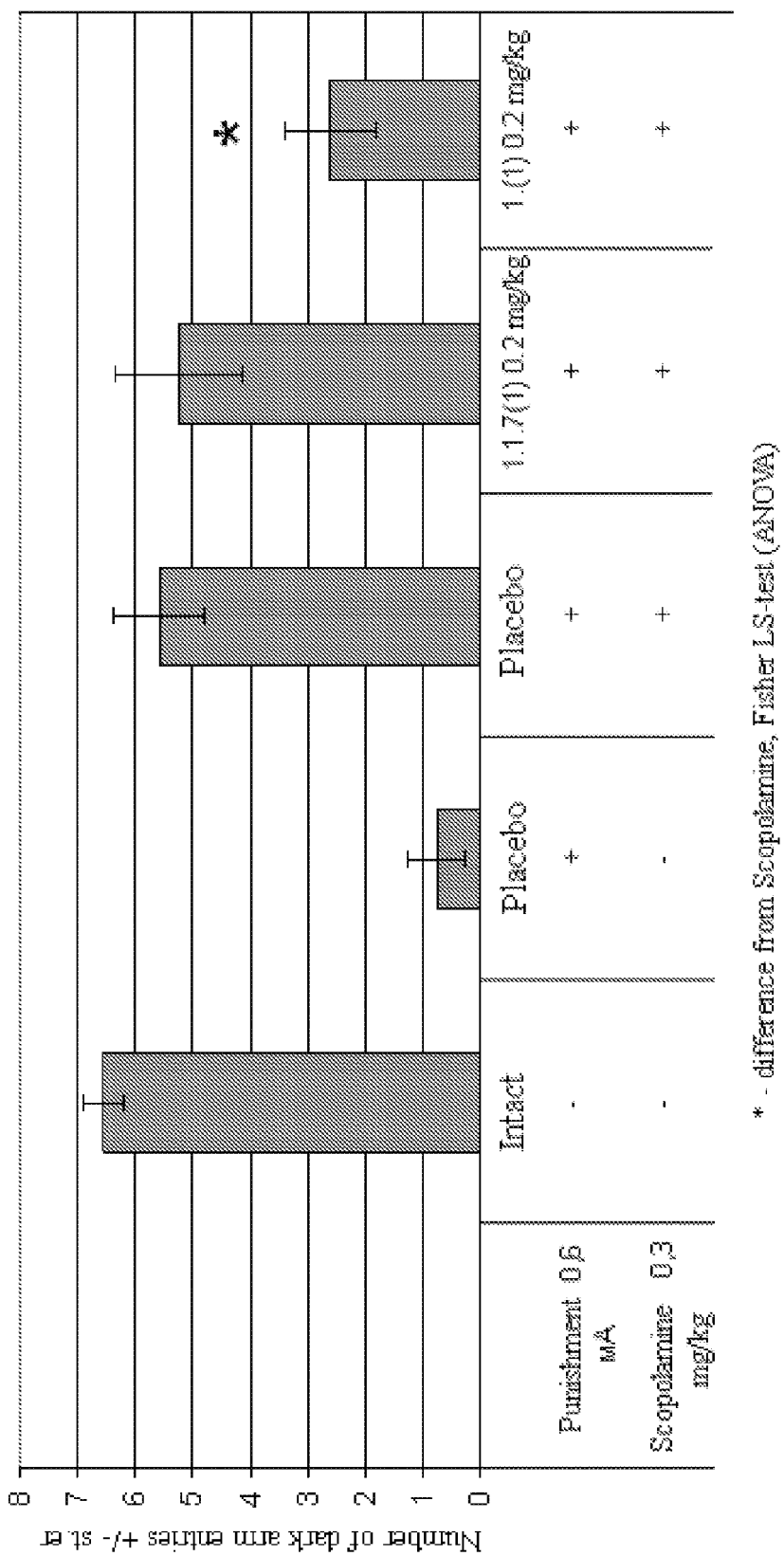

FIG. 6 The number of dark arm entries in 24 hours after training of mice to avoid dark arms in the shuttle chamber (average value±standard error). The number in brackets is a dose of compounds 1(1) and 1.1.7(1) in mg/kg. The tested compounds 1(1) and 1.1.7(1) were injected 60 minutes before the test. The difference from the group of animals received Scopolamine: *—$p<0.05$; —$p<0.01$; *—$p<0.001$.

Figure 7:
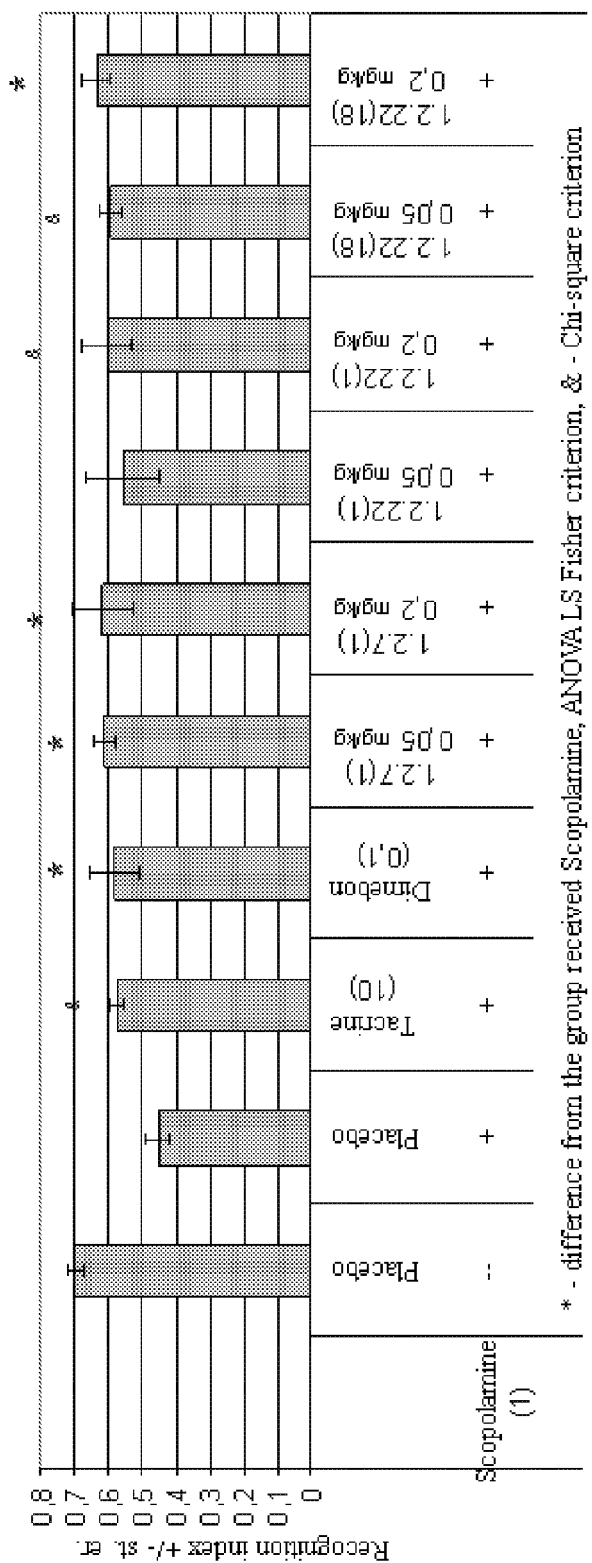

FIG. 7 Results for novel object recognition test in mice (average value±standard error). Doses of compounds 1.2.7(1), 1.2.22(1) and 1.2.22(18) in mg/kg are given in brackets. The tested compounds 1.2.7(1), 1.2.22(1) and 1.2.22(18) were injected 60 minutes before the test. The difference from the group of animals received Scopolamine: *—p<0.05 in accordance with criterium $\chi^2$.

Figure 8:
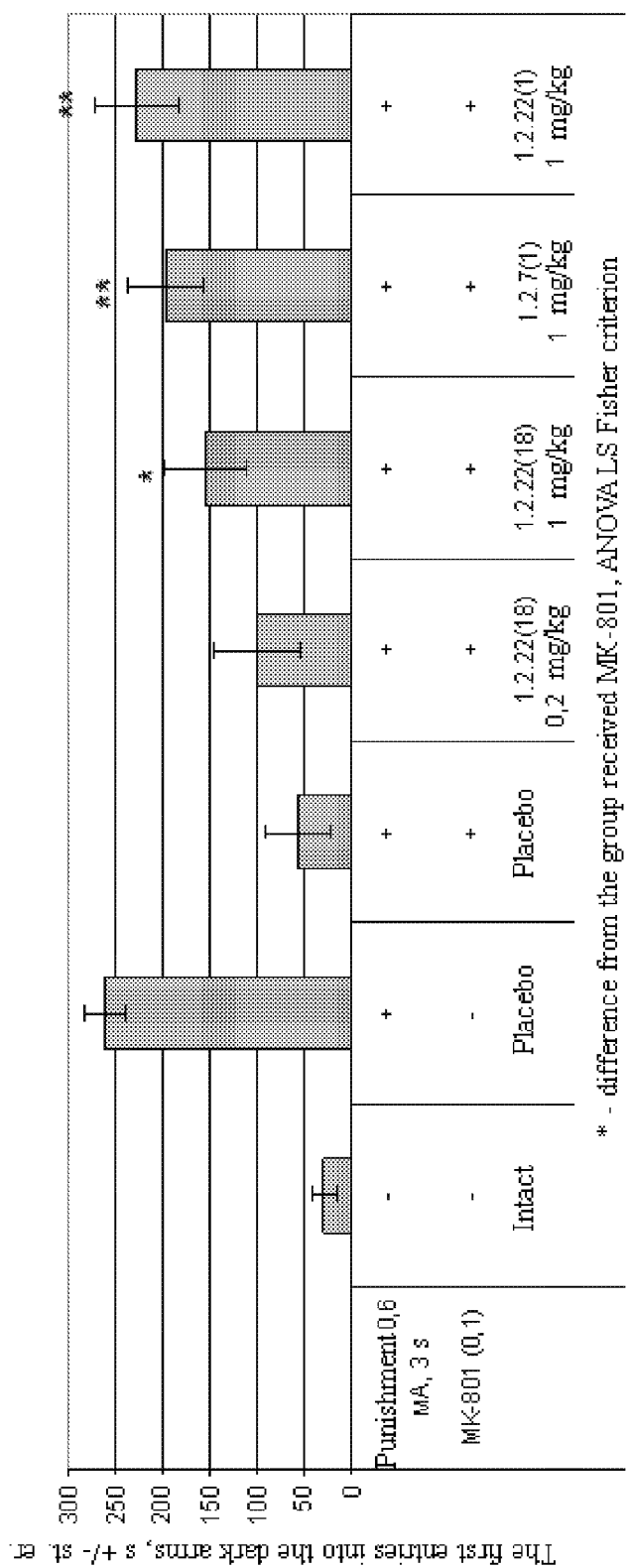

FIG. 8 The latent period of the first entries into the dark arms in 24 hours after training of rats to avoid entering the dark arms in the shuttle chamber (average value±standard error). The numbers in brackets are doses of compounds 1.2.7(1), 1.2.22(1) and 1.2.22(18) in mg/kg. The tested compounds 1.2.7(1), 1.2.22(1) and 1.2.22(18) were injected 60 minutes before the test. The difference from the group of animals received MK-801: *—p<0.05; —p<0.01; *—p<0.001.

Figure 9:
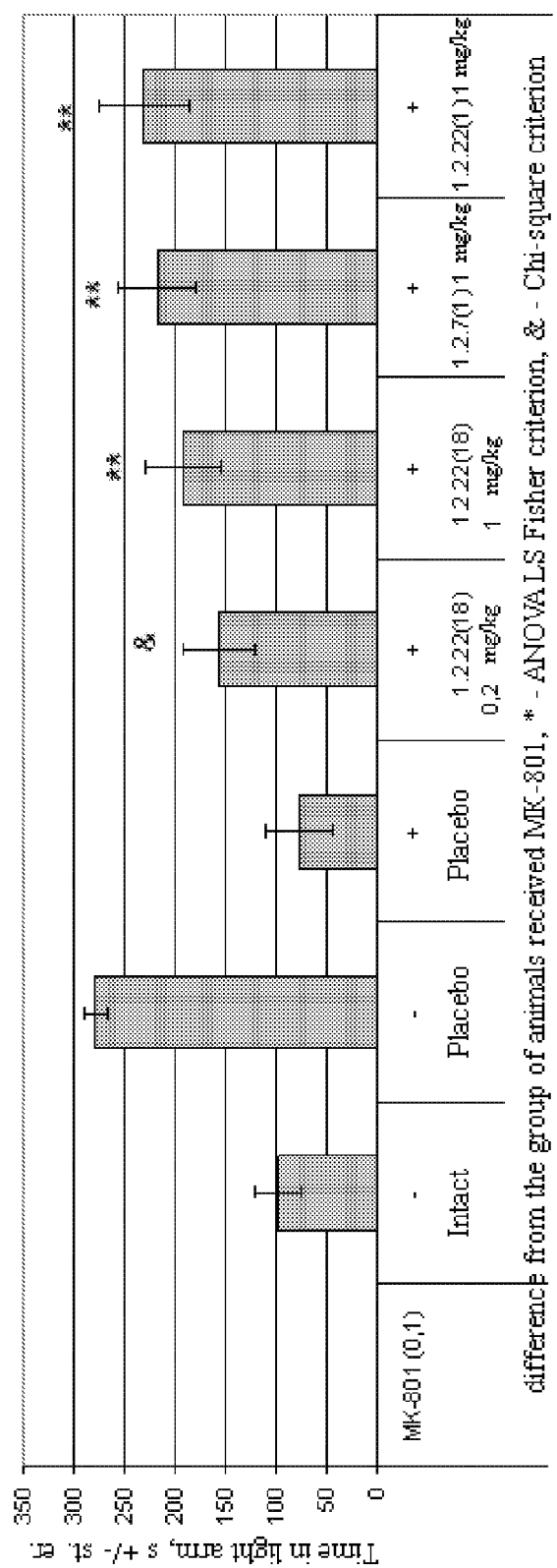

FIG. 9 Duration of light arm stays in 24 hours after training of rats to avoid dark arms in the shuttle chamber (average value±standard error). The numbers in brackets are doses of compounds 1.2.7(1), 1.2.22(1) and 1.2.22(18) in mg/kg. The tested compounds 1.2.7(1), 1.2.22(1) and 1.2.22(18) were injected 60 minutes before the test. The difference from the group of animals received MK-801: *—p<0.05; —p<0.01; *—p<0.001.

Figure 10:
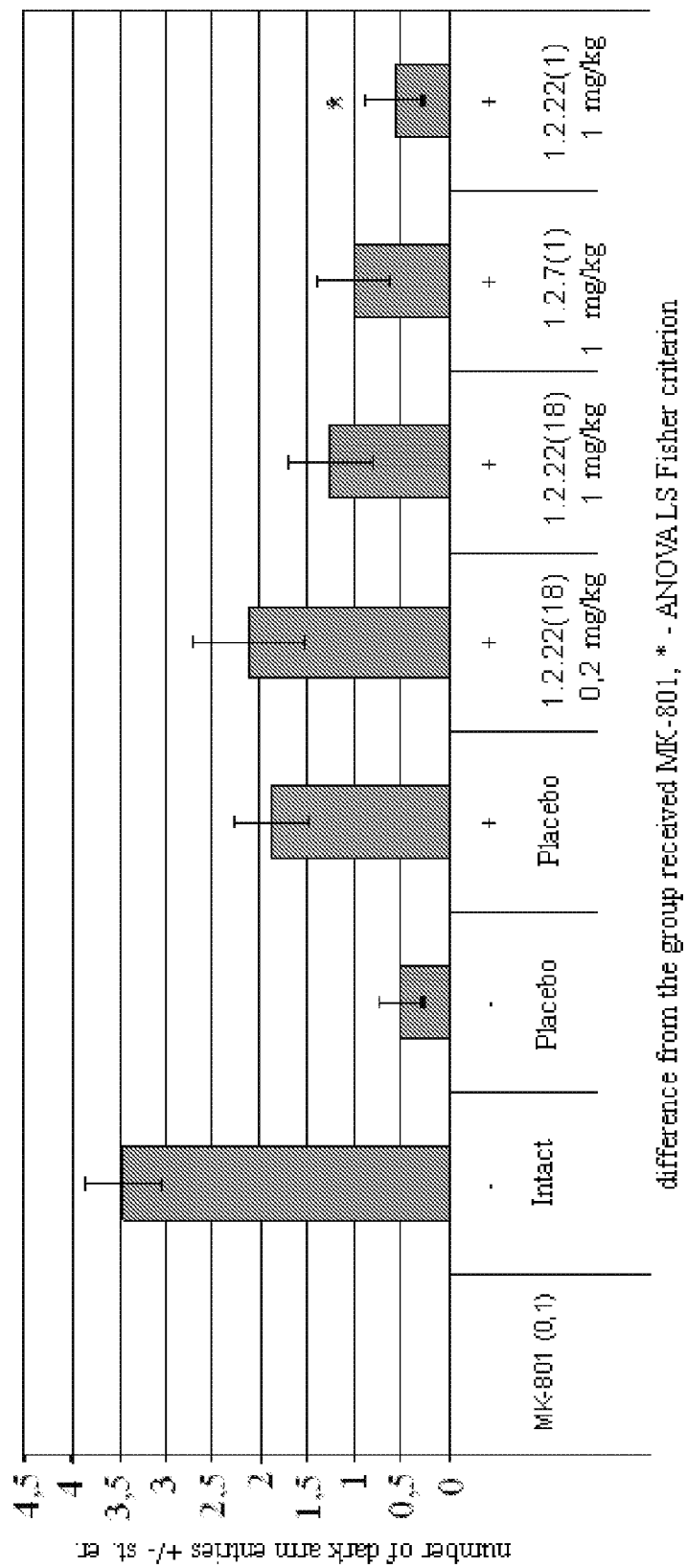

FIG. 10 The number of dark arm entries in 24 hours after training of rats to avoid dark arms in the shuttle chamber (average value±standard error). The numbers in brackets are doses of compounds 1.2.7(1), 1.2.22(1) and 1.2.22(18) in mg/kg. The tested compounds 1.2.7(1), 1.2.22(1) and 1.2.22(18) were injected 60 minutes before the test. The difference from the group of animals received MK-801: *—p<0.05; ***—p<0.001.

Figure 11:
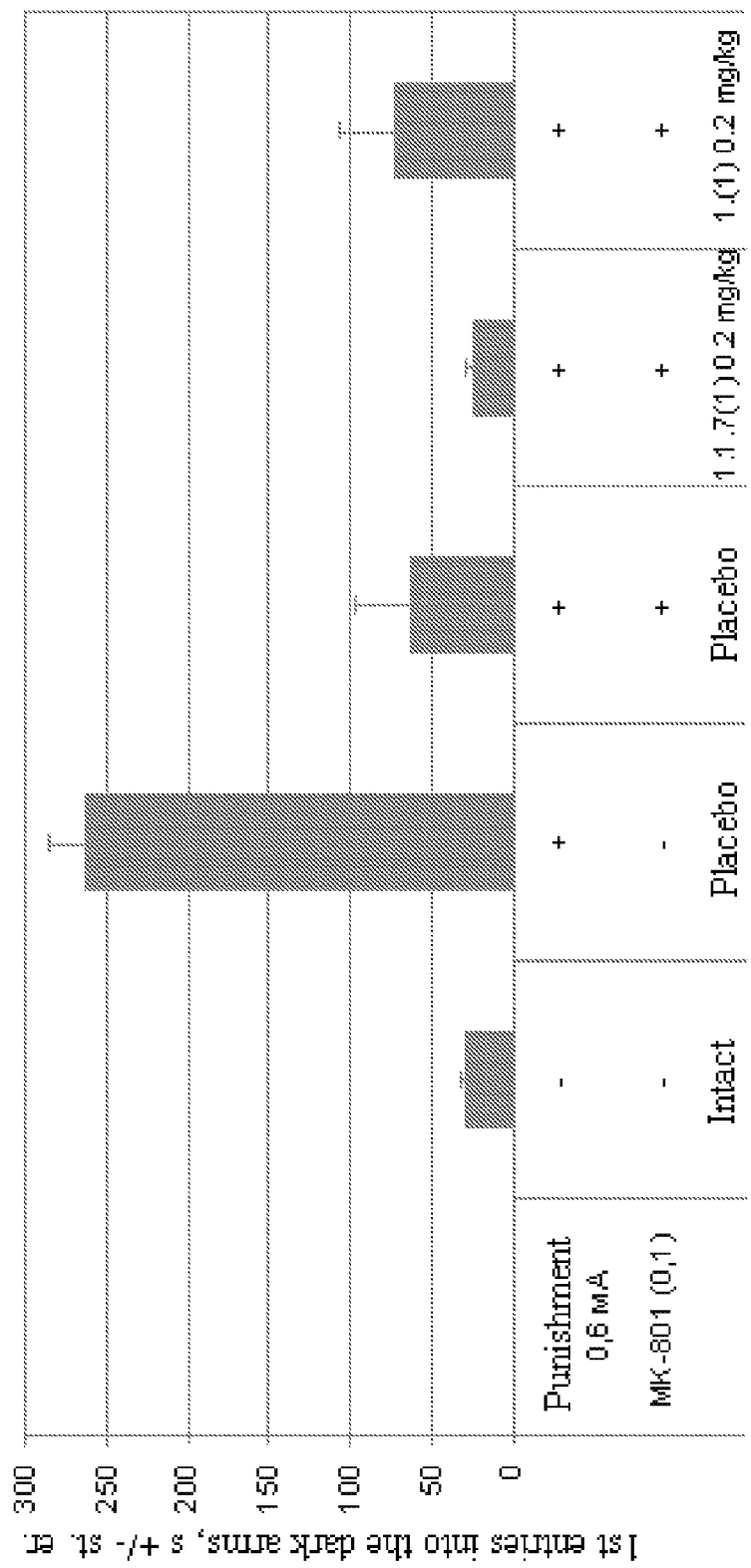

FIG. 11 The latent period of first entries into the dark arms in 24 hours after training of mice to avoid entering the dark arms in the shuttle chamber (average value±standard error). The numbers in brackets are doses of compounds 1(1) and 1.1.7(1) in mg/kg. The tested compounds 1(1) and 1.1.7(1) were injected 30 minutes before the test. The difference from the group of animals received MK-801: *—p<0.05; —p<0.01; *—p<0.001.

Figure 12:
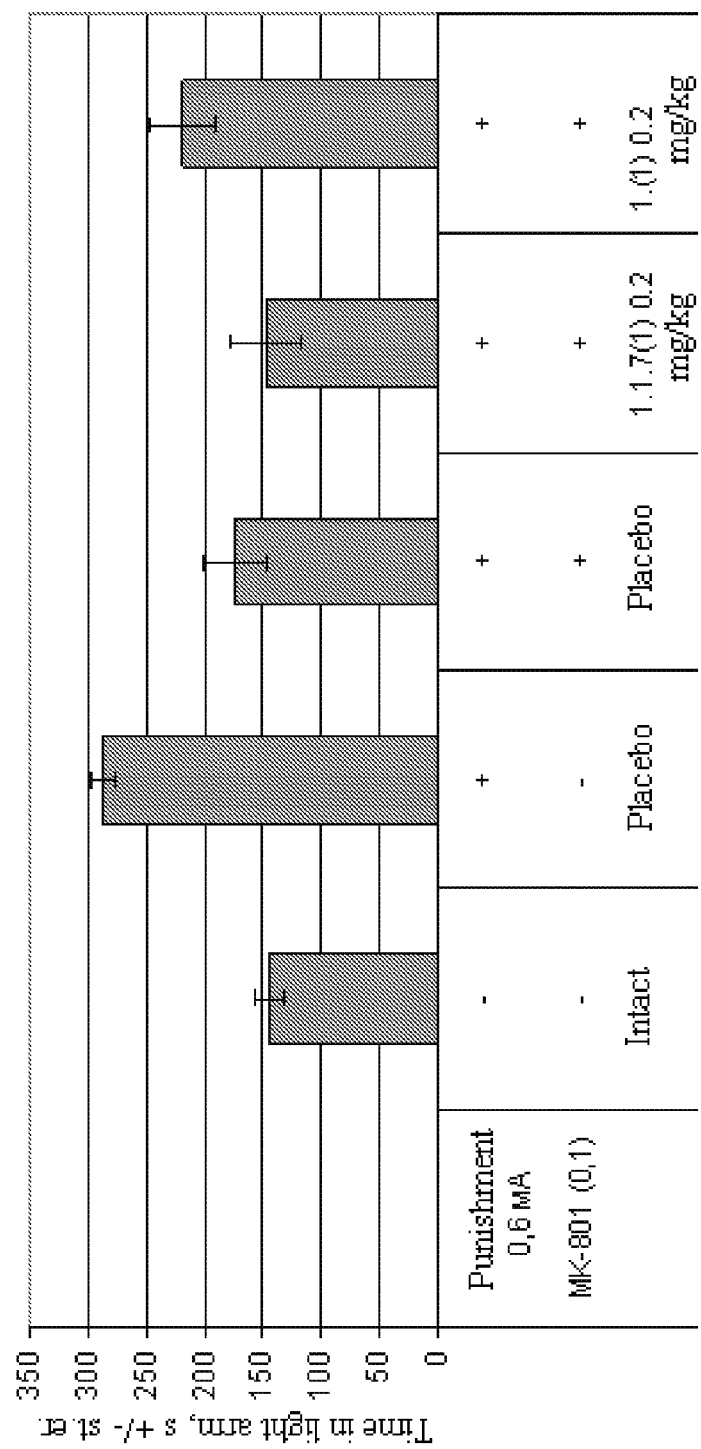

FIG. 12 Duration of light arm stays in 24 hours after training of mice to avoid dark arms in the shuttle chamber (average value±standard error). The numbers in brackets are doses of compounds 1(1) and 1.1.7(1) in mg/kg. The tested compounds 1(1) and 1.1.7(1) were injected 30 minutes before the test. The difference from the group of animals received MK-801: *—p<0.05; —p<0.01; *—p<0.001.

Figure 13:
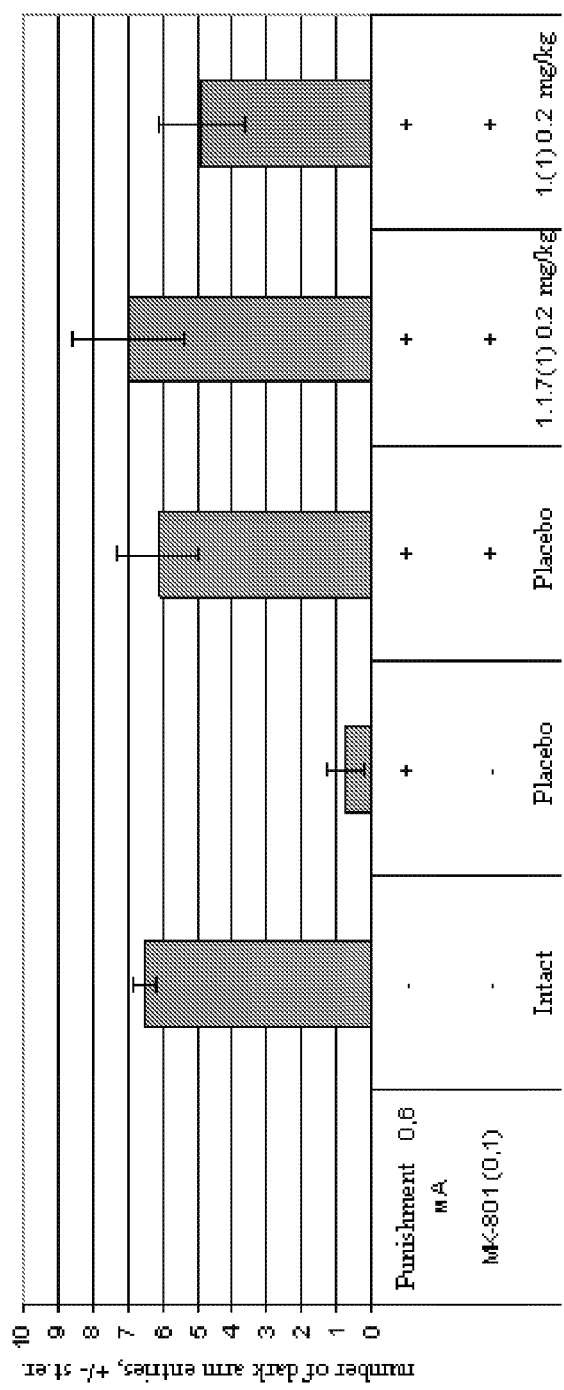

FIG. 13 The number of dark arm entries in 24 hours after training of mice to avoid dark arms in the shuttle chamber (average value±standard error). The numbers in brackets are doses of compounds 1(1) and 1.1.7(1) in mg/kg. The tested compounds 1(1) and 1.1.7(1) were injected 30 minutes before the test. The difference from the group of animals received MK-801: *—p<0.05; —p<0.01; *—p<0.001.

Figure 14:
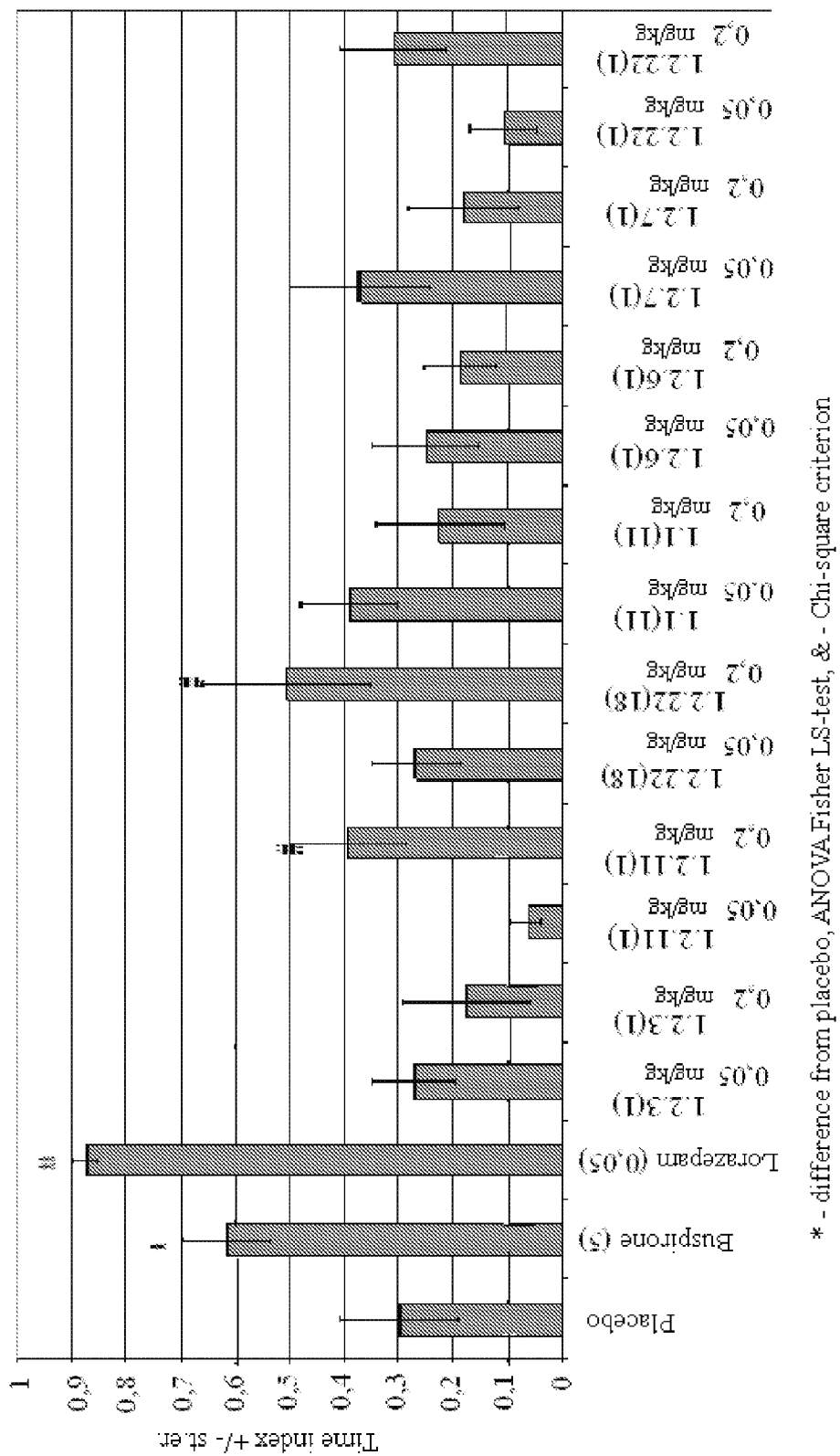

FIG. 14 Ratio of time spent by animals in the opened arms to the total time spent in the arms of both types (average value±standard error). Doses of compounds 1.1(11), 1.2.3(1), 1.2.6(1), 1.2.7(1), 1.2.11(1), 1.2.22(1), 1.2.22(18) (mg/kg) are given in brackets. The difference from the group of animals received placebo: *—p<0.05; —p<0.01; *—p<0.001.

Figure 15:
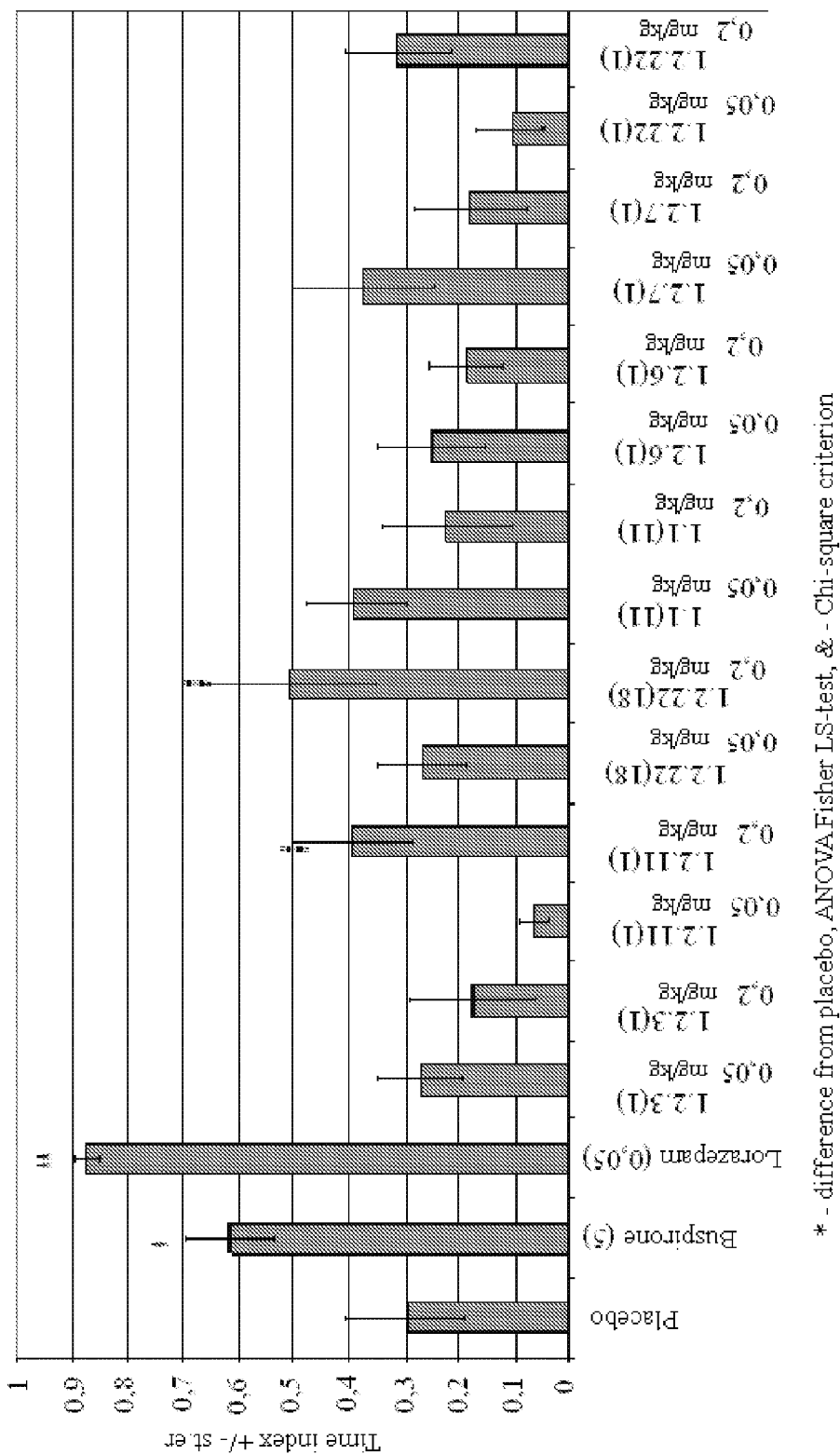

FIG. 15 Ratio of the opened arm entry numbers to the whole numbers of entries into the arms of both types (average value±standard error). Doses of compounds 1.1(11), 1.2.3(1), 1.2.6(1), 1.2.7(1), 1.2.11(1), 1.2.22(1), 1.2.22(18) (mg/kg) are given in brackets. The difference from the group of animals received placebo: *—p<0.05; —p<0.01; *—p<0.001.

Figure 16:
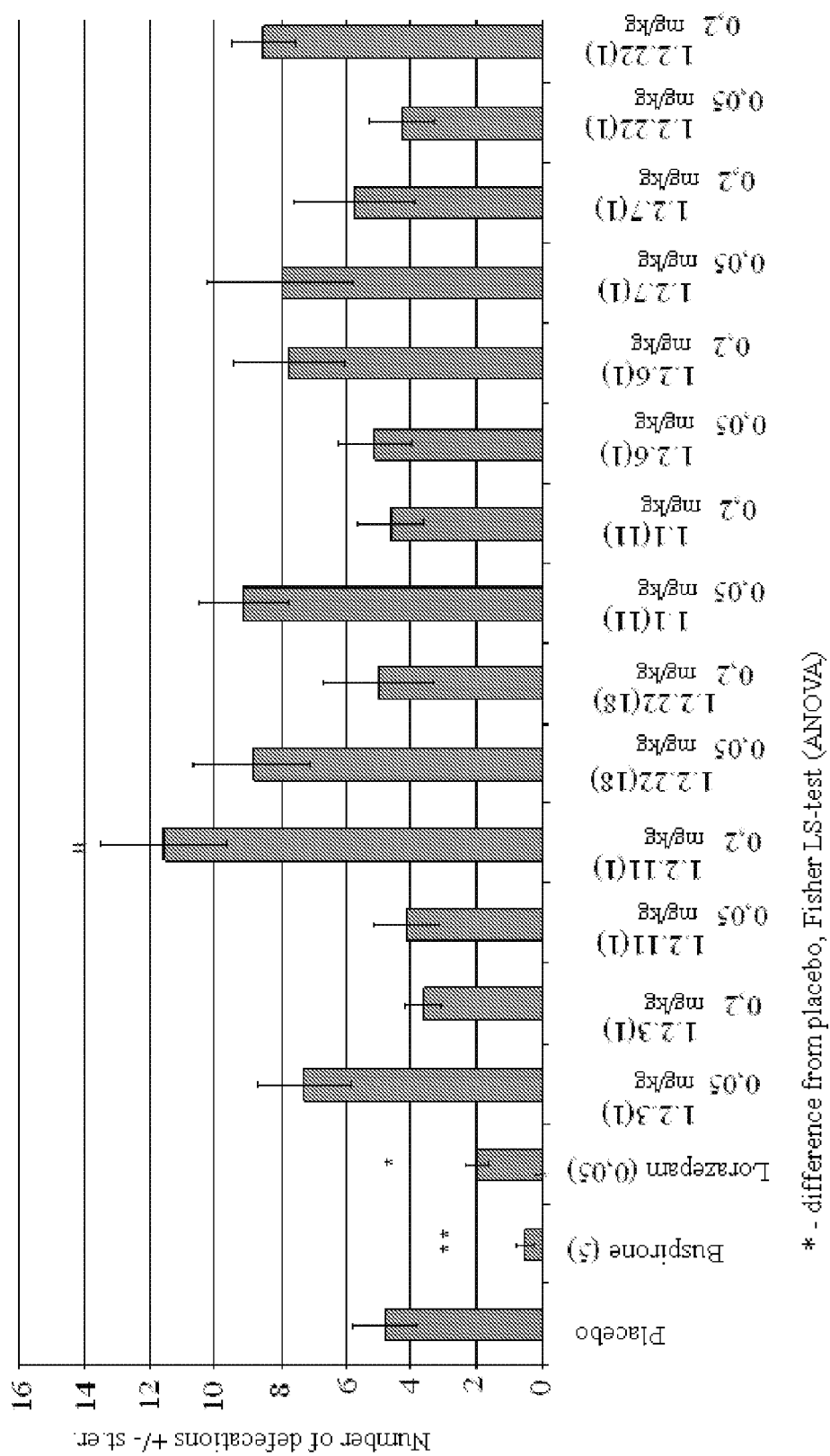

FIG. 16 The defecation number in plus-maze test (average value±standard error). Doses of compounds 1.1(11), 1.2.3(1), 1.2.6(1), 1.2.7(1), 1.2.11(1), 1.2.22(1), 1.2.22(18) (mg/kg) are given in brackets. The difference from the group of animals received placebo: *—p<0.05; —p<0.01; *—p<0.001.

Figure 17:
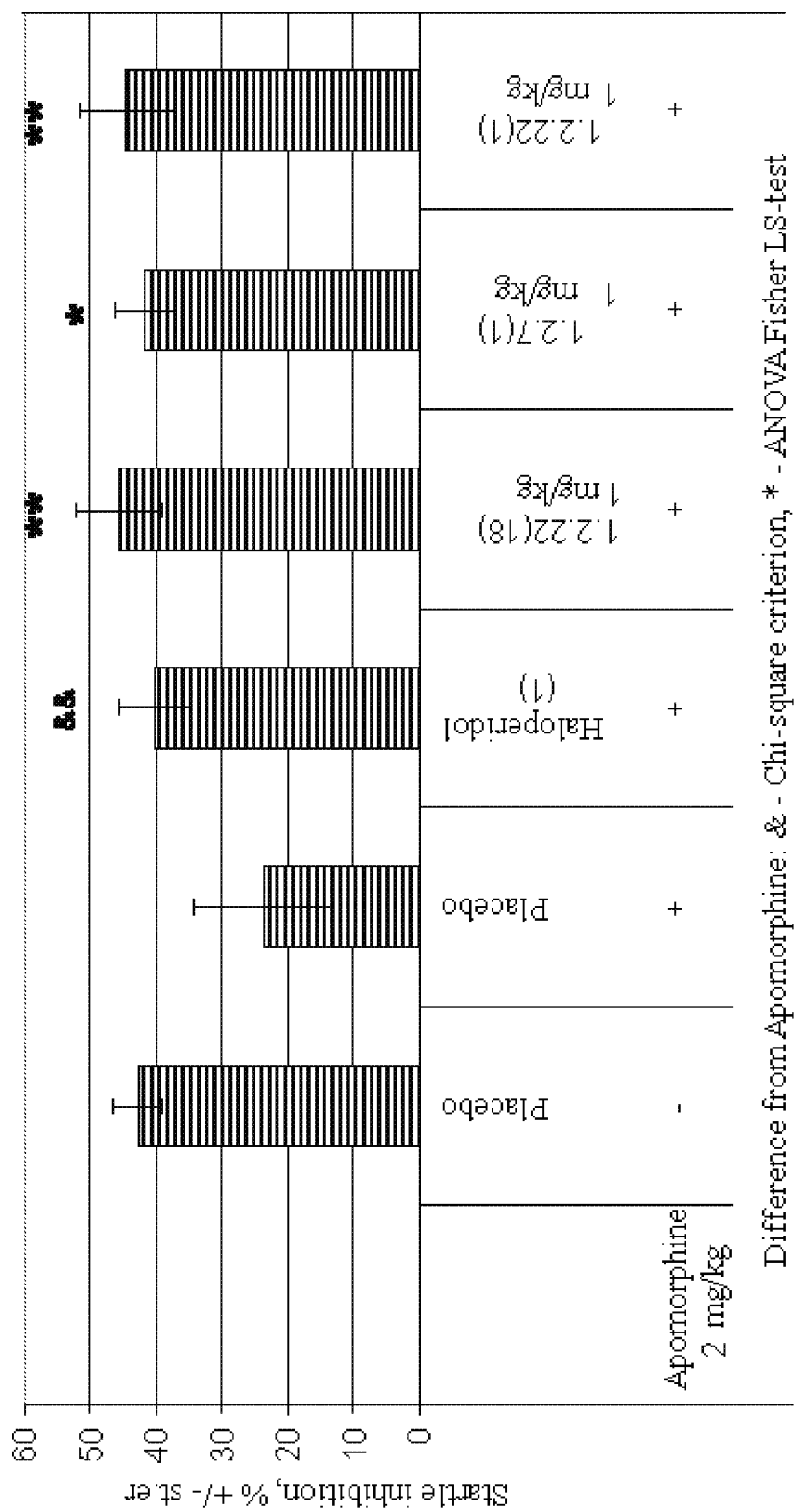

FIG. 17 Test results of prepulse inhibition of the startle response in mice.

Figure 18:
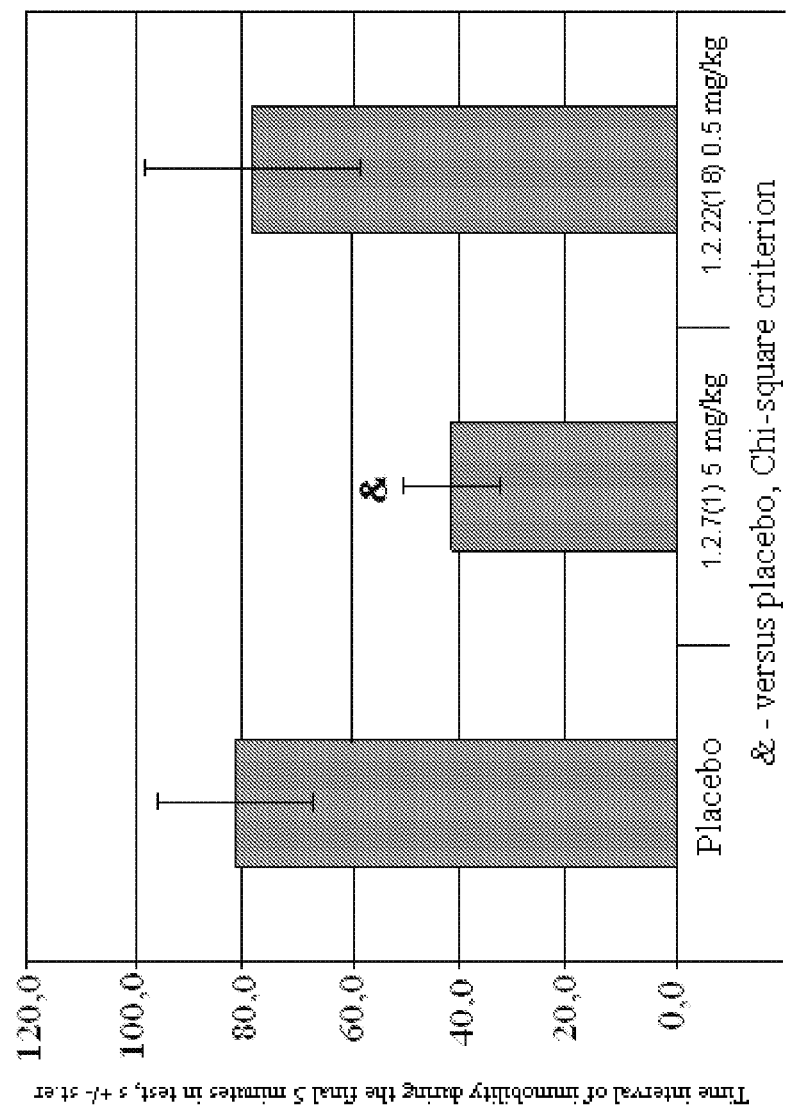

FIG. 18 Time interval of immobility during the final 5 minutes in Porsolt's test.

Figure 19:
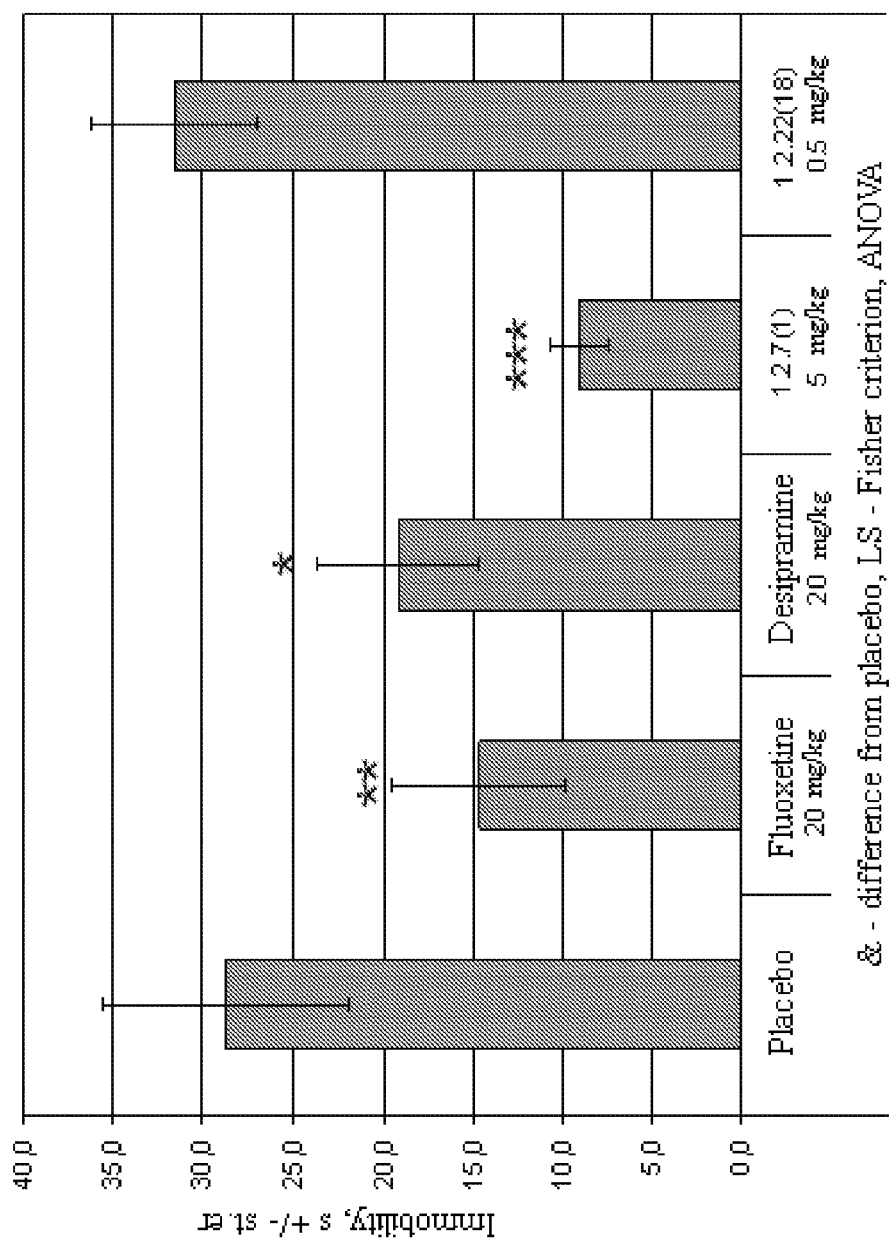

FIG. 19 Results for compounds 1.2.7(1) and 1.2.22(18) in tail suspension test.

Below the invention is described by means of specific examples, which illustrate but not limit the scope of the invention.

EXAMPLE 1

General method for the preparation of substituted 3-arylsulfonyl-pyrazolo[1,5-a]pyrimidines of the general formula 1 (X=S, NH). A mixture of aminopyrazole 2 (0.005 mol), the corresponding dicarbonyl compound or its derivative (0.0055 mol) of the general formula 3 and 5 ml of AcOH or another suitable solvent was stirred for 4-12 hours. The precipitated solid was filtered off, washed with methanol and water. If it was necessary, the product was recrystallized from the proper solvent or subjected to chromatographic purification or separation.

Table 2 shows some examples of novel 2-alkylsulfanyl-3-arylsulfonyl-pyrazolo[1,5-a]pyrimidines of the general formulas 1(X=S), 1.1, 1.1.1, 1.1.2, 1.1.3, 1.1.4, 1.1.5, 1.1.9, 1.1.10, 1.1.11, 1.1.12, 1.1.13, 1.1.17, 1.1.18, 1.1.19 and salts thereof, as well as LCMS and NMR data. Table 3 represents some examples of novel 2-alkylamino-3-arylsulfonyl-pyrazolo[1,5-a]pyrimidines of the general formulas 1(X=NH), 1.2, 1.2.1, 1.2.2, 1.2.3, 1.2.4, 1.2.5, 1.2.8, 1.2.9, 1.2.13, 1.2.14, 1.2.15, 1.2.19, 1.2.20, 1.2.21 and salts thereof, as well as their LCMS and NMR data.

EXAMPLE 2

General method for the preparation of substituted 2-alkylsulfinyl-3-arylsulfonyl-pyrazolo[1,5-a]pyrimidines of the general formula 1(X=SO). Hydrogen peroxide (88 mkl, 1 mmol, 35%) was added to a solution of 2-alkylsulfanyl-3-arylsulfonyl-pyrazolo[1,5-a]pyrimidine (μmol) of the general formula 1(X=S) in AcOH (10 ml) and the resultant mixture was stirred at 80° C. for 7 h. The mixture was evaporated in vacuo, the product was purified by column chromatography on silica gel (eluent chloroform/ethyl acetate=5:1). Yield was 75%-87%.

Table 2 represents some examples of novel 2-alkylsulfinyl-3-arylsulfonyl-pyrazolo[1,5-a]pyrimidines of the general formula 1(X=SO) and their LCMS and NMR data.

EXAMPLE 3

General method for the preparation of substituted 3-arylsulfonyl-7-(omega-hydroxyalkyl)-pyrazolo[1,5-a]pyrimidines of the general formulas 1.1.6, 1.2.6 and substituted 3-arylsulfonyl-5-(omega-hydroxyalkyl)-pyrazolo[1,5-a]pyrimidines of the general formulas 1.1.7, 1.2.7. A solution of 7-alkyloxyalkyl-3-arylsulfonyl-pyrazolo[1,5-a]pyrimidines (0.36 mmol) of the general formulas 1.1.4, 1.1.5, 1.2.4, 1.2.5 in distilled dichloromethane (10 ml) was added dropwise to solution of BBr$_3$ (0.1 ml, 0.27 mg, 3.0 equivalent) in distilled dichloromethane (10 ml) at rt. The reaction mixture was kept at 20° C. for 12 h, then, at vigorous stirring water (20 ml) was added and stirring was prolonged for 30 minutes. The organic layer was separated, water layer was extracted with ether two times. The organic phases were combined, evaporated in vacuo, the residue was subjected to chromatography. Compounds of the general formulas 1.1.6, 1.2.6, 1.1.7, 1.2.7 were prepared, some of them are represented in Tables 2 and 3.

EXAMPLE 4

General method for the preparation of substituted 3-arylsulfonyl-7-alkoxy-pyrazolo[1,5-a]pyrimidines of the general formulas 1.1.8, 1.2.10. 3-Arylsulfonyl-7-chloro-pyrazolo[1,5-a]pyrimidine of the general formula 4 was added to a solution of sodium ethoxide (2.5 mmol) in suitable solvent (25 ml, alcohol, DMF and others). The reaction mixture was kept in microwave reactor for 2 hours at 75° C., cooled, the precipitated solid was filtered off, washed with methanol, dissolved in dichloromethane, passed through thin layer of silica gel and evaporated to dryness. If it was necessary, the obtained products 1.1.8, 1.2.10 were recrystallized from the proper solvent.

Tables 2 and 3 show some examples of novel substituted 3-arylsulfonyl-7-alkoxy-pyrazolo[1,5-a]pyrimidines of the general formulas 1.1.8, 1.2.10 and their LCMS and NMR data.

EXAMPLE 5

General method for the preparation of 3-arylsulfonyl-pyrazolo[1,5-a]pyrimidine-carboxylic acids of the general formulas 1.1.14, 1.1.15, 1.1.16, 1.2.16, 1.2.17 and 1.2.18. Solution of 85% KOH (4.0 mmol, 263 mg) in water (20 ml) was added to a solution of the ester (2.0 mmol) of the general formulas 1.1.11, 1.1.12, 1.1.13, 1.2.13, 1.2.14 or 1.2.15 in ethanol (50 ml), and the resultant mixture was stirred at 20° C. for 6-18 h. (LCMS control). The solvent was evaporated in vacuo, the residue was diluted with water to volume of 200 ml. The resultant solution was acidified with HCl to pH 4-5. The precipitated white solid was filtered off, washed with water and dried in the opened air. Tables 2 and 3 shows some examples of novel 3-arylsulfonyl-pyrazolo[1,5-a]pyrimidine-carboxylic acids of the general formulas 1.1.14, 1.1.15, 1.1.16, 1.2.16, 1.2.17 and 1.2.18 and their LCMS and NMR data.

EXAMPLE 6

General method for the preparation of amides of 3-arylsulfonyl-pyrazolo[1,5-a]pyrimidine-carboxylic acids of the general formulas 1.1.17, 1.1.18, 1.1.19, 1.2.19, 1.2.20 and 1.2.21. Carbonyldiimidazole (0.992 mmol, 259 mg) was added to the solution of the acid (0.902 mmol) of the general formulas 1.1.14, 1.1.15, 1.1.16, 1.2.16, 1.2.17 or 1.2.18 in DMF (5 ml). The reaction mixture was stirred at 75° C. for 1 h, then amine (0.992 mmol) of the general formula 5 was added and the resultant mixture was kept at 75° C. by night. (LCMS control). After the reaction was completed, the reaction mixture was poured into 5% Na$_2$CO$_3$ water solution. The product was extracted with dichloromethane, extract was dried over Na$_2$SO$_4$ and evaporated in vacuo. The obtained amides of the general formulas 1.1.17, 1.1.18, 1.1.19, 1.2.19, 1.2.20 and 1.2.21 were used for preparation of salts without further purification. Tables 2 and 3 show some examples of novel amides of 3-arylsulfonyl-pyrazolo[1,5-a]pyrimidine carboxylic acids of the general formulas 1.1.17, 1.1.18, 1.1.19, 1.2.19, 1.2.20 and 1.2.21 and their LCMS and NMR data.

EXAMPLE 7

General method for the preparation of 3-arylsulfonyl-pyrazolo[1,5-a]pyrimidines of the general formulas 1.1.20, 1.1.21, 1.1.22, 1.2.22, 1.2.23 and 1.2.24 ($R^{10}$=$R^{11}$=H).

A. A solution of triethylamine (139 mcl, 101 mg, 1.18 mmol) in acetone (1 ml) and a solution of ethoxycarbonyl chloride (109 mcl, 123 mg, 1.29 mmol) in acetone (1 ml) were added dropwise one after another to a solution of the corresponding acid (1.0 mmol) of the general formulas 1.1.14, 1.1.15, 1.1.16, 1.2.16, 1.2.17 or 1.2.18 in acetone (10 ml). The resultant mixture was stirred at 0° C. for 30 min., then water (0.35 ml) solution of sodium azide (109 mg, 1.53 mmol) was added dropwise and stirring at 0° C. was continued for additional hour. The obtained reaction mixture was poured into ice water (30 ml). The product was extracted with dichloromethane cooled previously to 0° C., the solvent was evaporated in vacuo to volume of 2-3 ml at room temperature. The prepared solution of the general formulas 7.1, 7.2, 7.3 was diluted with dioxane to volume of 5 ml. This solution was added dropwise to boiling dioxane (20 ml) and the resultant mixture was boiled for 1 hour. The prepared solution of isocyanate of the general formula 8.1, 8.2, 8.3 was cooled to 70° C., 20% water HCl solution (5 ml) was added, stirring at 80° C. was continued for 3 hours till isocyanate hydrolysis was completed (LCMS control). After cooling of the reaction mixture amines of the general formulas 1.1.20, 1.1.21, 1.1.22, 1.2.22, 1.2.23 or 1.2.24 were separated as hydrochlorides.

B. Carbonyl compound (3 mmol) of the general formula 9 and sodium triacetoxyborohydride (2.5 mmol) were added to the solution of the corresponding amine (1 mmol) of the general formulas 1.1.20, 1.2.22, 1.1.21, 1.2.23, 1.1.22, 1.2.24, where $R^{10}$=$R^{11}$=H in dichloroethane (10 ml). The mixture was stirred for 3 h at 20° C. (LCMS control). To complete the reaction additional amount of carbonyl compound (3 mmol) of the general formula 9 and sodium triacetoxyborohydride (2.5 mmol) were added and stirring was continued for 12 h. The reaction mixture was diluted with water and extracted with dichloromethane, organic extract was washed with 10% K$_2$CO$_3$ solution, dried over Na$_2$SO$_4$ and evaporated. Compounds of the general formulas 1.1.20, 1.1.21, 1.1.22, 1.2.22, 1.2.23 and 1.2.24, 1.1.14, 1.1.15, 1.1.16, 1.2.16, 1.2.17 or 1.2.18 where $R^{10}$=H, $R^{11}$=CH$_2$NR$^{12}$R$^{13}$ were separated by means of column chromatography on silica gel (eluent hexane:ethyl acetate: triethylamine=30:10:1). Hydrochlorides were prepared by the addition of excessive amount of HCl solution in dioxane to acetone solution of the compound, if it was necessary, the hydrochloride was precipitated by addition of ether.

Tables 2 and 3 represent some examples of novel 3-arylsulfonyl-pyrazolo[1,5-a]pyrimidine-alkylamines of the general formulas 1.1.20, 1.1.21, 1.1.22, 1.2.22, 1.2.23, 1.2.24 1.1.14, 1.1.15, 1.1.16, 1.2.16, 1.2.17 and 1.2.18, their salts and LCMS and NMR date.

EXAMPLE 8

General method for the preparation of 6-amino-3-arylsulfonyl-pyrazolo[1,5-a]pyrimidines of the general formulas 1.1.20 and 1.2.22 where n=0, $R^{10}$=$R^{11}$=H.

A. A solution of 6-aryldiazenyl-3-arylsulfonyl-pyrazolo[1,5-a]pyrimidine (0.63 mmol) of the general formula 1 where $R^2$=Ar—N=N— in MeOH (9 ml) and benzene (3 ml) was hydrogenated over 10% Pd/C (30 mg) at 1 atm for 12 h. The product was separated by HPLC method. 6-Amino-3-arylsulfonyl-pyrazolo[1,5-a]pyrimidines of the general formulas 1.1.20 and 1.2.22 where n=0; $R^{10}$=$R^{11}$=H were prepared.

B. A solution of KOH (135 g, 2.41 mol) in water (350 ml) was added to a suspension of N-(3-arylsulfonyl)-(pyrazolo[1,5-a]pyrimidin-6-yl)-acetamide (0.268 mol) of the general formula 1, where $R^2$=Ac-NH— in methanol (11). The reaction mixture was stirred under reflux for 72 hours. After the reaction was completed (LCMS control), the obtained bulky mass was thoroughly comminuted with the help of rotary dispergator or ultrasound, after that the precipitate was filtered off, washed with water and dried in vacuo. 6-Amino-3-arylsulfonyl-pyrazolo[1,5-a]pyrimidines of the general formulas 1.1.20 and 1.2.22 where n=0, $R^{10}$=$R^{11}$=H were prepared.

C. 3M $H_2SO_4$ (0.275 ml) and alkylaldehyde (2.1 mmol) were added to a suspension of 2-methylsulfanyl-3-arylsulfonyl-pyrazolo[1,5-c]pyrimidine-6-amine (0.236 mmol) of the general formula 1.1.20 where n=0; $R^{10}$=$R^{11}$=H in dioxane (3.5 ml). To the resultant solution at stirring in small portions $NaBH_4$ (92 mg, 2.42 mmol) was added for 2 h. The reaction mixture was poured into 10% $K_2CO_3$ solution (100 ml), extracted with dichloromethane, dried over $Na_2SO_4$ and evaporated on rotary evaporator. Purification was carried out by means of flash chromatography. 2-Methylsulfanyl-3-arylsulfonyl-pyrazolo[1,5-c]pyrimidine-6-dialkylamines of the general formula 1.1.20 where n=0, $R^{10}$=$R^{11}$=$C_1$-$C_3$alkyl were prepared.

D. 3M $H_2SO_4$ (450 ml) was added to a suspension of $N^2$,5,7-trimethyl-3-arylsulfonyl-pyrazolo[1,5-c]pyrimidine-2,6-diamine (0.227 mol) of the general formula 1.2.22 where n=0, $R^{10}$=$R^{11}$=H in ethanol (3750 ml). The suspension was heated to 90° C. and then cooled to 20° C. An aldehyde (2.5 mol) was added to the prepared mixture. In 30 min at vigorous stirring $NaBH_4$ (56 g, 1.47 mol) was added in small portions at such a speed that the temperature of the reaction mixture does not exceed 25° C. (if it was necessary, external cooling was used). When the reaction was completed (LCMS control) the precipitate was filtered off and washed thoroughly with water. 2-(Methylamino)-3-arylsulfonyl-pyrazolo[1,5-c]pyrimidine-6-dialkylamines of the general formula 1.2.22 where n=0; $R^{10}$=$R^{11}$=$C_1$-$C_3$alkyl were prepared.

Tables 2 and 3 represent some examples of 6-amino-3-arylsulfonyl-pyrazolo[1,5-a]pyrimidines of the general formulas 1.1.20 and 1.2.22 where n=0 and their LCMS and NMR date.

TABLE 2

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---|---|---|---|
| 1(1) | | 349.43 | 350 | $^1$H NMR (DMSO-$D_6$, 400 MHz) δ 8.22 (m, 2H), 7.58 (m, 1H), 7.51 (m, 2H), 6.88 (s, 1H), 3.24 (s, 3H), 2.83 (s, 3H), 2.71 (s, 3H). |
| 1(2) | | 383.88 | 384 | |
| 1(3) | | 383.88 | 384 | $^1$H NMR (CDCl$_3$, 400 MHz) δ 8.20 (m, 2H), 7.9 (t, J = 7.4 Hz, 1H), 7.52 (t, J = 7.4 Hz, 2H), 3.25 (s, 3H), 2.99 (s, 3H), 2.82 (s, 3H). |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1(4) | | 367.88 | 368 | $^1$H NMR (CDCl$_3$, 400 MHz) δ 8.20 (m, 2H), 7.46-7.55 (m, 3H), 2.85 (s, 3H), 2.75 (s, 3H), 2.62 (s, 3H). |
| 1.1(5) | | 412.33 | 413 | $^1$H NMR (CDCl$_3$, 400 MHz) δ 8.20 (d, J = 7.2 Hz, 2H), 7.54 (t, J = 7.2 Hz, 1H), 7.48 (t, J = 7.2 Hz, 2H), 2.90 (s, 3H), 2.80 (s, 3H), 2.62 (s, 3H). |
| 1.1(6) | | 425.53 | 426 | $^1$H NMR (DMSO-D$_6$, 400 MHz) δ 8.63 (d, J = 2.4 Hz, 1H), 8.45 (d, J = 4.8 Hz, 1H), 8.05 (m, 2H), 7.76 (dd, J$_1$ 2.4 Hz, J$_2$ = 4.8 Hz, 1H), 7.56-7.67 (m, 4H), 2.60 (s, 3H), 2.54 (s, 3H), 2.40 (s, 3H). |
| 1.1(7) | | 462.98 | 427 | $^1$H NMR (DMSO-D$_6$, 400 MHz) δ 8.63 (d, J = 2.4 Hz, 1H), 8.45 (d, J = 4.8 Hz, 1H), 8.05 (m, 2H), 7.76 (dd, J$_1$ = 8.8 Hz, J$_2$ = 2.4 Hz, 1H), 7.56-7.67 (m, 4H), 2.60 (s, 3H), 2.54 (s, 3H), 2.40 (s, 3H). |
| 1.1(8) | | 459.55 | 460 | NMR-$^1$H (CDCl$_3$): 9.02 (s, 1H); 8.93 (d, J = 8.4 Hz, 1H); 8.85-8.88 (m, 1H); 8.72-8.78 (m, 2H); 8.27-8.30 (m, 2H); 7.90-7.98 (m, 2H); 7.43-7.55 (m, 5H); 2.67 (s, 3H). |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1(9) •$C_2H_2O_4$ | | 549.59 | 460 | |
| 1.1(12) | | 437.55 | 438 | $^1$H NMR (CDCl$_3$, 400 MHz) δ 8.26 (m, 2H), 7.91 (m, 2H), 7.48-7.59 (m, 6H), 2.97 (s, 3H), 2.87 (s, 3H), 2.67 (s, 3H). |
| 1.1.1(1) | | 305.38 | 306 | $^1$H NMR(DMSO-D$_6$, 400 MHz) δ 8.70 (dd, J$_1$ = 1.6 Hz, J$_2$ = 4.4 Hz, 1H), 8.59 (dd, J$_1$ = 1.6 Hz, J$_2$ = 6.8 Hz, 1H), 8.20 (m, 2H), 7.49-7.55 (m, 3H), 6.97 (dd, J$_1$ = 4.4 Hz, J$_2$ = 6.8 Hz, 1H), 2.62 (s, 3H). |
| 1.1.1(2) | | 323.37 | 324 | |
| 1.1.1(3) | | 339.82 | 340 | $^1$H NMR (CDCl$_3$, 400 MHz) δ 8.73 (dd, J$_1$ = 4.0 Hz, J$_2$ = 1.2 Hz, 1H), 8.62 (dd, J$_1$ = 6.8 Hz, J$_2$ = 1.2 Hz, 1H), 8.19 (s, 1H), 8.09 (d, J = 7.6 Hz, 1H), 7.51 (d, J = 8.0 Hz, 1H), 7.43 (t, J = 8.0 Hz, 1H), 7.01 (dd, J$_1$ = 6.8 Hz, J$_2$ = 4.4 Hz, 1H), 2.63 (s, 3H). |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---|---|---|---|
| 1.1.1(4) | | 357.81 | 358 | $^1$H NMR (CDCl$_3$, 400 MHz) δ 8.73 (m, 1H), 8.63 (d, J = 7.2 Hz, 1H), 8.29 (dd, J = 6.8 Hz, J$_2$ = 2.0 Hz, 1H), 8.11 (ddd, J$_1$ = 6.8 Hz, J$_2$ = 4.4 Hz, J$_3$ = 2.0 Hz, 1H), 7.25 (t, J = 8.8 Hz, 1H), 7.02 (dd, J$_1$ = 6.0 Hz, J$_2$ = 4.4 Hz, 1H), 2.63 (s, 3H). |
| 1.1.1(5) | | 333.43 | 334 | |
| 1.1.1(6) | | 319.41 | 320 | |
| 1.1.1(7) | | 323.37 | 324 | $^1$H NMR (CDCl$_3$, 400 MHz) δ 8.71 (dd, J$_1$ = 4.4 Hz, J$_2$ = 2.0 Hz, 1H), 8.61 (dd, J$_1$ = 6.8 Hz, J$_2$ = 2.0 Hz, 1H), 8.22 (m, 2H), 7.16 (m, 2H), 7.00 (dd, J$_1$ = 6.8 HZ, J$_2$ = 4.4 Hz, 1H), 2.63 (s, 3H) |
| 1.1.2(1) | | 319.41 | 320 | $^1$H NMR (CDCl$_3$, 400 MHz) δ 8.41 (d, J = 6.8 Hz, 1H), 8.20-8.23 (m, 2H), 7.54 (m, 1H), 7.48 (m, 2H), 6.80 (d, J = 6.8 Hz, 1H), 2.69 (s, 3H), 2.59 (s, 3H). |
| 1.1.2(2) | | 337.40 | 338 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---|---|---|---|
| 1.1.2(3) | | 337.40 | 338 | |
| 1.1.2(4) | | 353.85 | 354 | |
| 1.1.2(5) | | 371.84 | 372 | $^1$H NMR (CDCl$_3$, 400 MHz) δ 8.44 (d, J = 7.2 Hz, 1H), 8.35 (dd, J$_1$ = 6.8 Hz, J$_2$ = 2.0 Hz, 1H), 8.11 (ddd, J$_1$ = 6.4 Hz, J$_2$ = 4.0 Hz, J$_3$ = 2.0 Hz, 1H), 7.24 (t, J = 8.8 Hz, 1H), 6.85 (d, J = 7.2 Hz, 1H), 2.71 (s, 3H), 2.61 (s, 3H). |
| 1.1.2(6) | | 347.46 | 348 | |
| 1.1.3(1) | | 319.41 | 320 | (CDCl$_3$, 400 MHz) δ 8.41 (d, J = 7.2 Hz, 1H), 8.20-8.23 (m, 2H), 7.54 (m, 1H), 7.49 (m, 2H), 6.80 (d, J = 7.2 Hz, 1H), 2.69 (s, 3H), 2.59 (s, 3H). |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---|---|---|---|
| 1.1.3(2) | 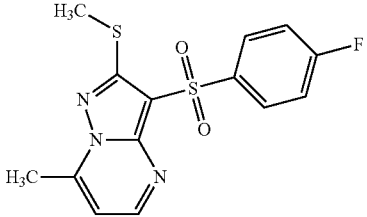 [SMILES: CSc1nn2c(C)ccnc2c1S(=O)(=O)c1ccc(F)cc1] | 337.40 | 338 | |
| 1.1.3(3) | 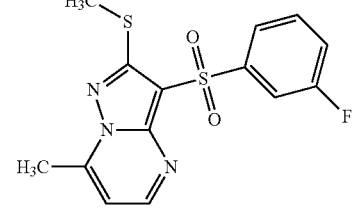 | 337.40 | 338 | |
| 1.1.3(4) | 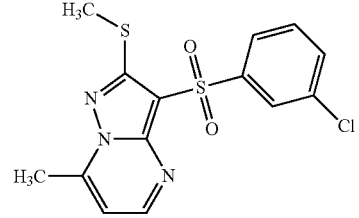 [SMILES: CSc1nn2c(C)ccnc2c1S(=O)(=O)c1cccc(Cl)c1] | 353.85 | 354 | |
| 1.1.3(5) | 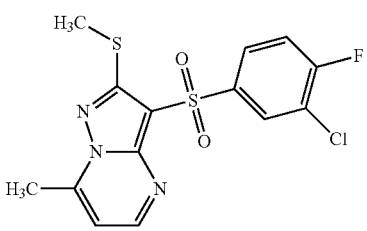 [SMILES: CSc1nn2c(C)ccnc2c1S(=O)(=O)c1ccc(F)c(Cl)c1] | 371.84 | 372 | ¹H NMR (CDCl₃, 400 MHz) δ 8.60 (d, J = 4.4 Hz, 1H), 8.28 (dd, J₁ = 6.4 Hz, J₂ = 2.0 Hz, 1H), 8.11 (ddd, J₁ = 6.4 Hz, J₂ = 4.4 Hz, J₃ = 2.0 Hz, 1H), 7.23 (t J = 8.8 Hz, 1H), 6.85 (d, J = 4.4 Hz, 1H), 2.79 (s, 3H), 2.66 (s, 3H). |
| 1.1.4(1) | 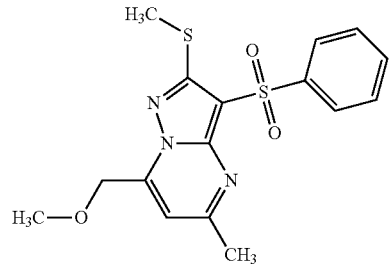 [SMILES: COCc1cc(C)nc2c(S(=O)(=O)c3ccccc3)c(SC)nn12] | 363.46 | 364 | 1H NMR (CDCl₃, 400 MHz) δ 8.22 (m, 2H), 7.45-7.55 (m, 3H), 6.96 (s, 1H), 4.85 (s, 2H), 3.59 (s, 3H), 2.70 (s, 3H), 2.59 (s, 3H). ¹³C NMR (CDCl₃, 75.5 MHz) δ 162.89, 156.15, 147.27, 145.14, 142.98, 132.30, 128.30, 126.45, 106.39, 105.81, 66.88, 59.35, 25.08, 12.88. |
| 1.1.4(2) | 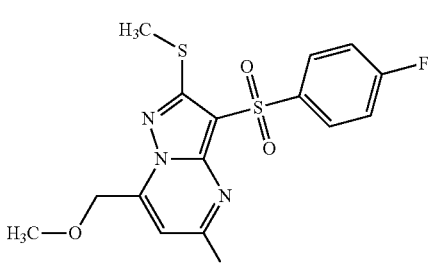 | 381.45 | 382 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.4(3) | | 381.45 | 382 | |
| 1.1.4(4) | | 397.91 | 398 | |
| 1.1.4(5) | | 415.90 | 416 | |
| 1.1.5(1) | | 363.46 | 364 | $^1$H NMR (CDCl$_3$, 400 MHz) δ 8.20 (d, J = 7.2 Hz, 2H), 7.45-7.55 (m, 3H), 7.05 (s, 1H), 4.66 (s, 2H), 3.52 (s, 3H), 2.75 (s, 3H), 2.63 (s, 3H). $^{13}$C NMR (CDCl$_3$, 75.5 MHz) δ 162.37, 156.32, 147.11, 146.25, 142.99, 132.27, 128.29, 126.51, 106.43, 106.15, 74.42, 58.70, 16.74, 12.87. |
| 1.1.5(2) | | 381.45 | 382 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.5(3) | | 381.45 | 382 | |
| 1.1.5(4) | | 397.91 | 398 | |
| 1.1.5(5) | | 415.90 | 416 | |
| 1.1.6(1) | | 349.43 | 350 | $^1$H NMR (DMSO-D$_6$, 400 MHz) δ 8.02 (m, 2H), 7.56-7.65 (m, 3H), 7.18 (s, 1H), 5.98 (t, J = 5.6 Hz, 1H), 4.90 (d, J = 5.6 Hz, 2H), 2.64 (s, 3H), 2.55 (s, 3H). |
| 1.1.6(2) | | 367.42 | 368 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.6(3) | | 367.42 | 368 | |
| 1.1.6(4) | | 383.88 | 384 | |
| 1.1.6(5) | | 401.87 | 402 | |
| 1.1.7(1) | | 349.43 | 350 | 1H NMR (CDCl$_3$, 400 MHz) δ 8.16 (m, 2H), 7.46-7.56 (m, 3H), 6.81 (s, 1H), 4.83 (d, J = 4.8 Hz, 2H), 3.73 (t, J = 4.8 Hz, 1H), 2.73 (s, 3H), 2.64 (s, 3H). |
| 1.1.7(2) | | 367.42 | 368 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---|---|---|---|
| 1.1.7(3) | 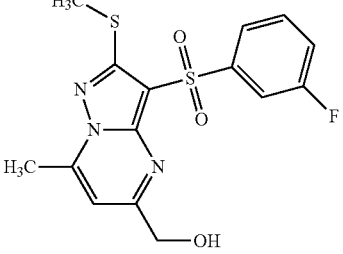 | 367.42 | 368 | |
| 1.1.7(4) | 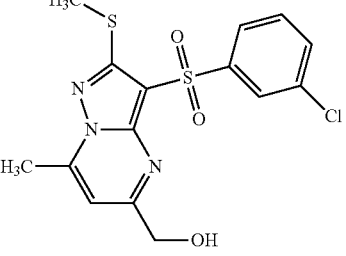 | 383.88 | 384 | |
| 1.1.7(5) | 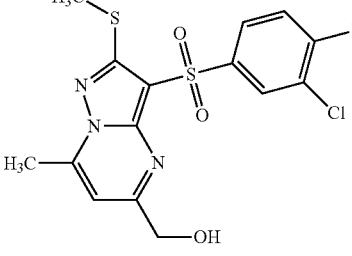 | 401.87 | 402 | |
| 1.1.8(1) | 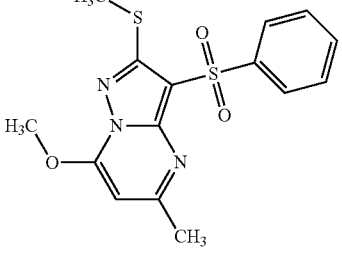 | 349.43 | 350 | |
| 1.1.8(2) | 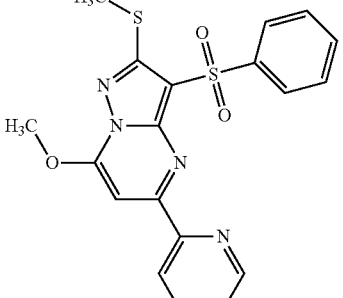 | 412.49 | 413 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---------|-------------|-------------------|-----|
| 1.1.8(3) | 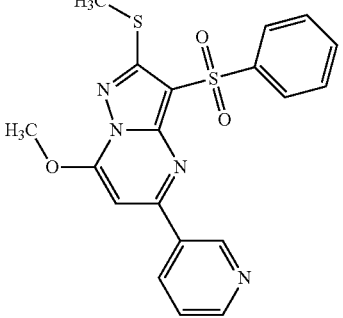 | 412.49 | 413 | |
| 1.1.8(3) •HCl | 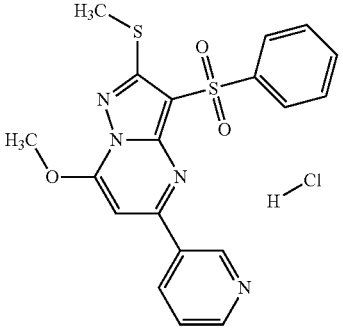 [SMILES: COc1cc(-c2cccnc2)nc2c(S(=O)(=O)c3ccccc3)c(SC)nn12 ; Cl] | 448.89 | 413 | |
| 1.1.8(3) •CH₃SO₃H | 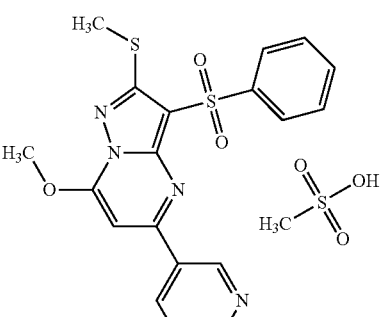 | 508.60 | 413 | |
| 1.1.8(4) | 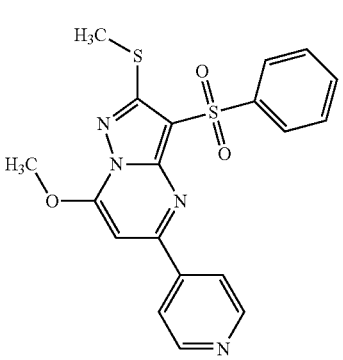 | 412.49 | 413 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.8(5) | | 367.42 | 368 | |
| 1.1.9(1) | | 382.47 | 383 | |
| 1.1.9(2) | | 382.47 | 383 | |
| 1.1.9(3) | | 382.47 | 383 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---|---|---|---|
| 1.1.9(4) | | 400.46 | 401 | |
| 1.1.9(5) | | 416.91 | 417 | |
| 1.1.9(6) | | 396.49 | 397 | |
| 1.1.9(7) | | 396.49 | 397 | NMR-$^1$H (CDCl$_3$): 9.30 (d, J = 2.0 Hz, 1H); 8.76 (d, J = 5.0 Hz, J = 1.5 Hz, 1H); 8.53-8.57 (m, 1H); 8.22-8.26 (m, 2H); 7.46-7.54 (m, 4H); 7.05 (s, 1H); 2.82 (s, 3H); 2.66 (s, 3H). |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.9(8) | | 396.49 | 397 | |
| 1.1.9(9) | | 414.48 | 415 | |
| 1.1.9(10) | | 430.94 | 431 | |
| 1.1.10(1) | | 382.47 | 383 | |
| 1.1.10(2) | | 418.93 | 383 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---|---|---|---|
| 1.1.10(3) | 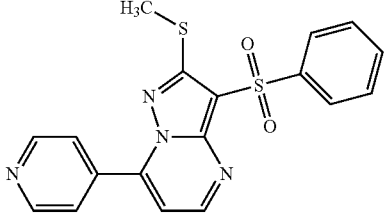 [SMILES: CSc1nn2c(-c3ccncc3)ccnc2c1S(=O)(=O)c1ccccc1] | 382.47 | 383 | |
| 1.1.10(4) | 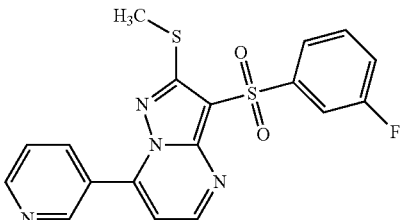 | 400.46 | 401 | |
| 1.1.10(5) | 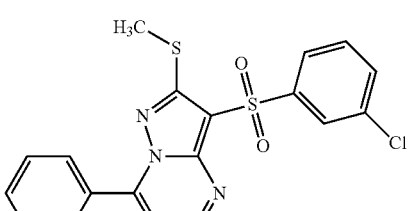 | 416.91 | 417 | |
| 1.1.10(6) | 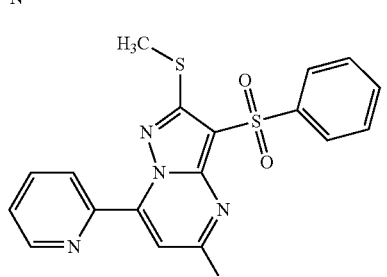 | 396.49 | 397 | 1H NMR (CDCl$_3$, 400 MHz) δ 9.17 (d, 1H), 8.81 (d, 1H), 8.37 (d, 1H), 8.25 (d, 2H), 7.53 (t, 4H), 6.94 (s, 1H), 2.77 (s, 3H), 2.55 (s, 3H). $^{13}$C NMR (CDCl$_3$, 75.48 MHz) δ 162.82, 156.50, 151.69, 149.41, 148.22, 142.82, 142.50, 136.46, 132.44, 128.36, 126.64, 125.85, 122.81, 109.18, 106.44, 24.97, 12.96. |
| 1.1.10(6) •HCl | 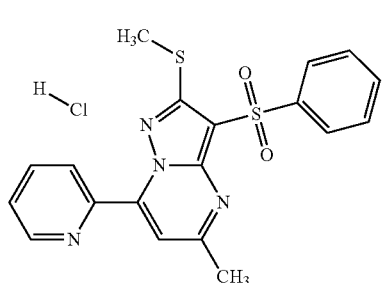 | 396.49 | 397 | NMR-$^1$H (DMSO-D$_6$): 9.26 (d, J = 1.5 Hz, 1H); 8.82 (dd, J = 5.4 Hz, J = 1.5 Hz, 1H); 8.61-8.65 (m, 1H); 8.04-8.08 (m, 2H); 7.72-7.77 (m, 1H); 7.58-7.68 (m, 3H); 7.55 (s, 1H); 2.68 (s, 3H); 2.50 (s, 3H). |
| 1.1.10(7) | 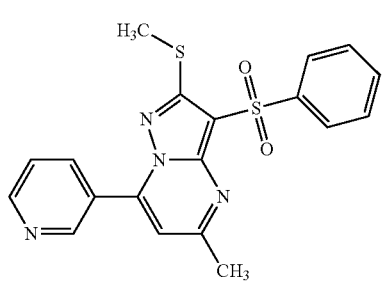 [SMILES: CSc1nn2c(-c3ccccn3)cc(C)nc2c1S(=O)(=O)c1ccccc1] | 432.95 | 397 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.10(8) | | 396.49 | 397 | ¹H NMR (CDCl₃, 400 MHz) δ 9.17 (d, 1H), 8.81 (d, 1H), 8.37 (d, 1H), 8.25 (d, 2H), 7.53 (t, 4H), 6.94 (s, 1H), 2.77 (s, 3H), 2.55 (s, 3H). ¹³C NMR (CDCl₃, 75.48 MHz) δ 162.82, 156.50, 151.69, 149.41, 148.22, 142.82, 142.50, 136.46, 132.44, 128.36, 126.64, 125.85, 122.81, 109.18, 106.44, 24.97, 12.96. |
| 1.1.10(9) | | 414.48 | 415 | |
| 1.1.10(10) | | 430.94 | 431 | |
| 1.1.11(1) | | 406.51 | 407 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.11(2) | | 447.58 | 448 | |
| 1.1.11(3) | | 433.55 | 434 | |
| 1.1.11(4) | | 461.61 | 462 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.11(5) | | 433.55 | 434 | |
| 1.1.12(1) | | 374.44 | 375 | $^1$H NMR (CDCl$_3$, 400 MHz) δ 8.29 (m, 2H), 7.47-7.57 (m, 4H), 4.07 (s, 3H), 2.82 (d, J = 0.4 Hz, 3H), 2.66 (s, 3H). |
| 1.1.13(1) | | 374.44 | 375 | $^1$H NMR (CDCl$_3$, 400 MHz) δ 8.01 (m, 2H), 7.57-7.67 (m, 4H), 3.97 (s, 3H), 2.66 (s, 3H), 2.56 (s, 3H). |
| 1.1.14(1) | | 378.45 | 379 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---|---|---|---|
| 1.1.16(1) | | 333.35 | 334 | |
| 1.1.17(1) •HCl | | 526.12 | 490 | |
| 1.1.17(2) •HCl | | 524.11 | 488 | |
| 1.1.18(1) •HCl | | 484.04 | 448 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---------|-------------|-------------------|-----|
| 1.1.19(1) •HCl | | 484.04 | 448 | |
| 1.1.20(1) | | 348.45 | 349 | |
| 1.1.20(2) •HCl | | 398.94 | 363 | ¹H NMR (DMSO-D₆, 400 MHz) δ 8.15 (s, 3H), 8.02 (m, 2H), 7.60 (m, 3H), 4.23 (s, 2H), 2.82 (s, 3H), 2.72 (s, 3H), 2.60 (s, 3H). |
| 1.1.20(2) •CH₃SO₃H | | 458.59 | 363 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---------|-------------|-------------------|-----|
| 1.1.20(3) •HCl | 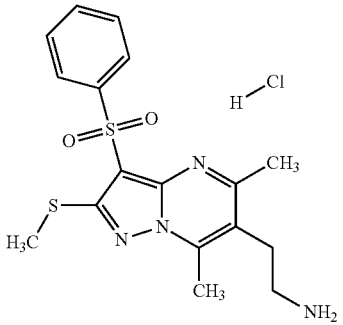 [SMILES: CSc1nn2c(C)c(CCN)c(C)nc2c1S(=O)(=O)c1ccccc1 ; Cl] | 412.96 | 377 | |
| 1.1.20(4) •HCl | 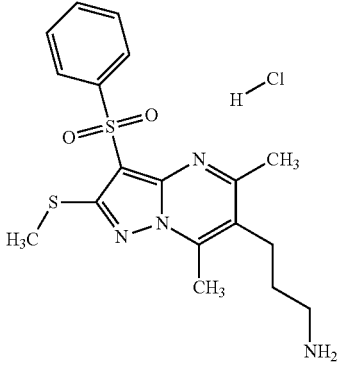 [SMILES: CSc1nn2c(C)c(CCCN)c(C)nc2c1S(=O)(=O)c1ccccc1 ; Cl] | 426.99 | 391 | |
| 1.1.20(5) •HCl | 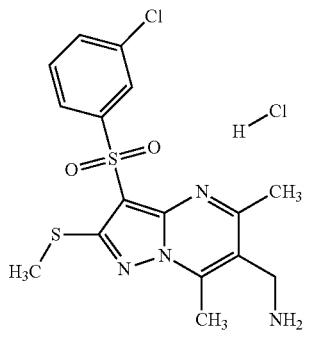 [SMILES: CSc1nn2c(C)c(CN)c(C)nc2c1S(=O)(=O)c1cccc(Cl)c1 ; Cl] | 433.38 | 397 | |
| 1.1.20(6) •HCl | 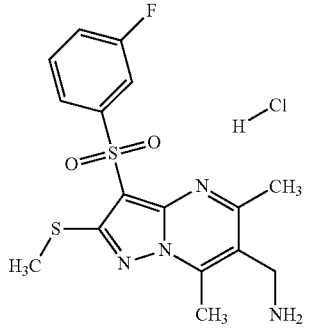 [SMILES: CSc1nn2c(C)c(CN)c(C)nc2c1S(=O)(=O)c1cccc(F)c1 ; Cl] | 416.93 | 381 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---------|-------------|-------------------|-----|
| 1.1.20(7) •HCl | 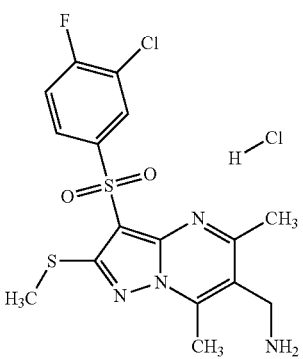 [SMILES: CSc1nn2c(C)c(CN)c(C)nc2c1S(=O)(=O)c1ccc(F)c(Cl)c1 ; Cl] | 451.37 | 415 | |
| 1.1.20(8) •HCl | 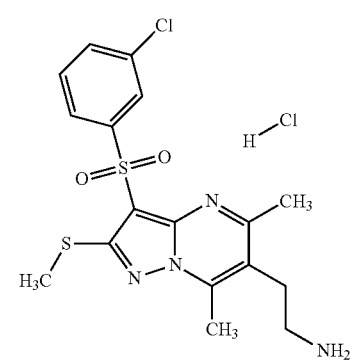 | 447.41 | 411 | |
| 1.1.20(9) •HCl | 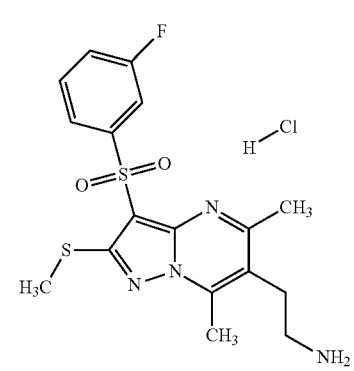 [SMILES: CSc1nn2c(C)c(CCN)c(C)nc2c1S(=O)(=O)c1cccc(Cl)c1 ; Cl] | 430.95 | 395 | |
| 1.1.20(10) •HCl | 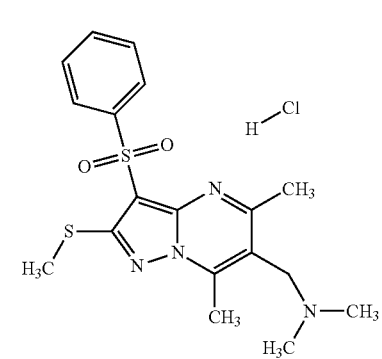 | 426.99 | 391 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---|---|---|---|
| 1.1.20(11) •HCl | 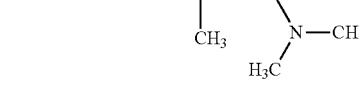 | 461.43 | 425 | |
| 1.1.20(12) •HCl | 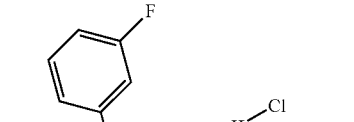 | 444.98 | 409 | |
| 1.1.20(13) •HCl | 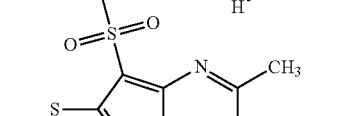 | 479.43 | 443 | |
| 1.1.20(14) •HCl | 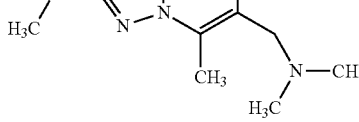 | 441.02 | 405 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---------|-------------|-------------------|-----|
| 1.1.20(15) •HCl | 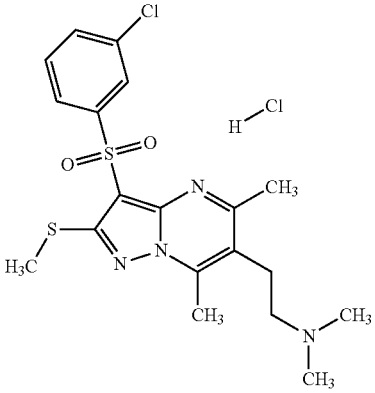 | 475.46 | 440 | |
| 1.1.20(16) •HCl | 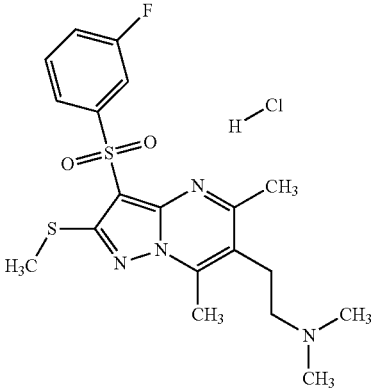 | 459.01 | 423 | |
| 1.1.20(17) •HCl | 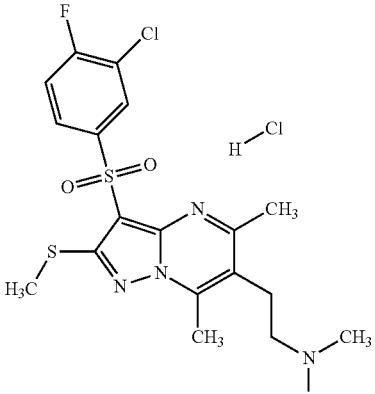 | 493.45 | 457 | |

TABLE 2-continued

Substituted 2-alkylsulfanyl-3-arylsulfonyl-pyrazolo[1,5-a]pyrimidines of the general formulas 1, 1.1.

| № | Formula | Mol. weight | LCMS, m/z (M + 1) | NMR |
|---|---|---|---|---|
| 1.1.20(18) •HCl | | 441.02 | 405 | |
| 1.1.20(19) | | 376.50 | 377 | 1H NMR (DMSO-D₆, 400 MHz) δ 8.01 (m, 2H), 7.55-7.64 (m, 3H), 2.77 (s, 6H), 2.66 (s, 3H), 2.57 (s, 6H) |
| 1.1.21(1) •HCl | | 394.91 | 349 | |
| 1.1.21(2) •HCl | | 398.94 | 363 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---|---|---|---|
| 1.1.21(3) •HCl | 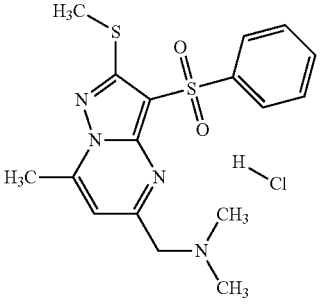 | 412.96 | 377 | |
| 1.1.21(4) | 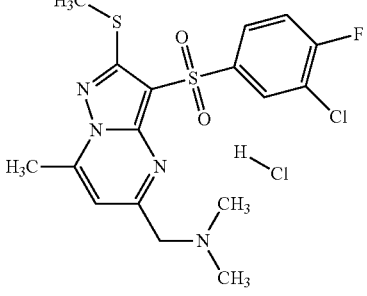 | 465.40 | 429 | |
| 1.1.21(5) •HCl | 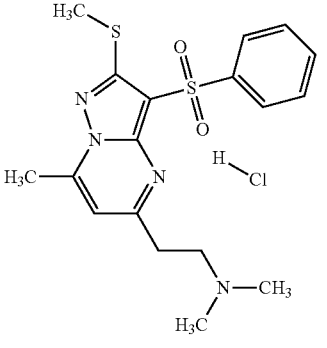 | 426.99 | 391 | |
| 1.1.22(1) •HCl | 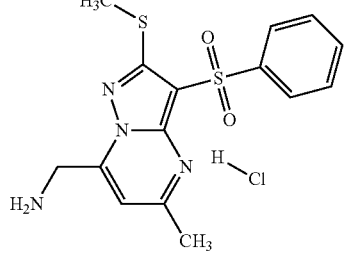 | 394.91 | 349 | |
| 1.1.22(2) •HCl | 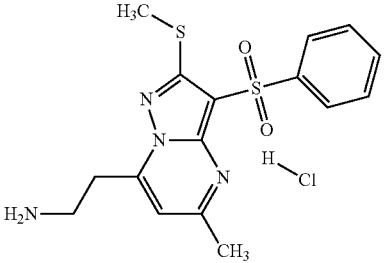 | 398.94 | 363 | |

TABLE 2-continued
Substituted 2-alkylsulfanyl-3-arylsulfonyl-pyrazolo[1,5-a]pyrimidines of the general formulas 1, 1.1.
| № | Formula | Mol. weight | LCMS, m/z (M + 1) | NMR |
|---|---------|-------------|-------------------|-----|
| 1.1.22(3) •HCl | 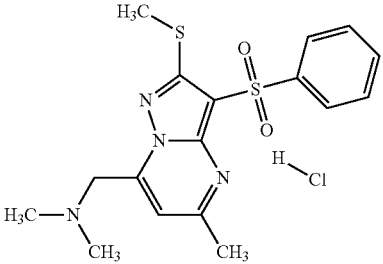 | 412.96 | 377 | |
| 1.1.22(4) •HCl | 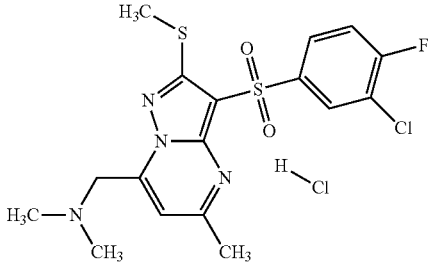 | 465.40 | 429 | |
| 1.1.22(5) •HCl | 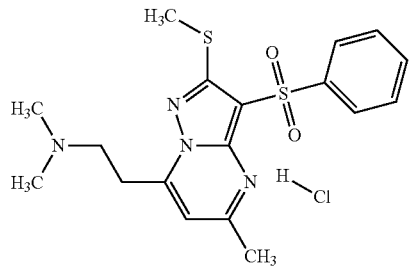 | 426.99 | 391 | |
TABLE 3
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2(1) | 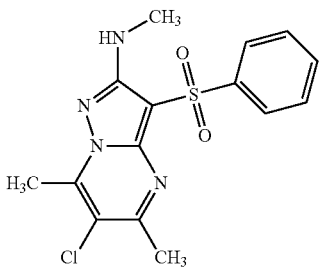 [SMILES: CNc1nn2c(C)c(Cl)c(C)nc2c1S(=O)(=O)c1ccccc1] | 350.83 | 351 | $^1$H NMR (CDCl$_3$, 400 MHz) δ 8.14 (m, 2H), 7.45-7.55 (m, 3H), 6.05 (q, J = 5.2 Hz, 1H), 3.05 (d, J = 5.2 Hz, 3H), 2.77 (s, 3H), 2.67 (s, 3H). |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2(3) •HCl | 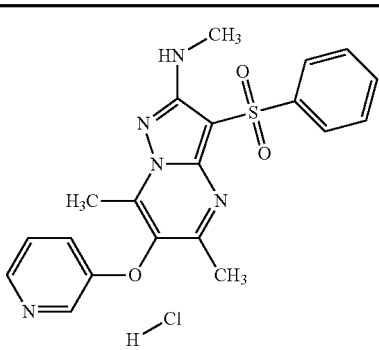 | 445.93 | 410 | |
| 1.2(4) | 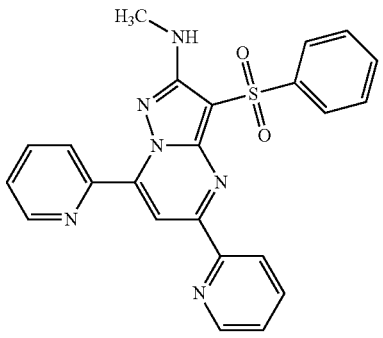 [SMILES: CNc1nn2c(-c3ccccn3)cc(-c3ccccn3)nc2c1S(=O)(=O)c1ccccc1] | 442.50 | 443 | NMR-$^1$H (CDCl$_3$): 9.01 (d, J = 8.4 Hz, 1H); 8.88 (s, 1H); 8.83-8.86 (m, 1H); 8.72-8.75 (m, 1H); 8.65 (d, J = 7.9 Hz, 1H); 8.22-8.26 (m, 2H); 7.89-7.94 (m, 2H); 7.44-7.53 (m, 4H); 7.38-7.43 (m, 1H); 6.19 (br. q, J = 5.0 Hz, 1H); 3.12 (d, J = 5.0 Hz, 3H). |
| 1.2(5) •C$_2$H$_4$O$_2$ | 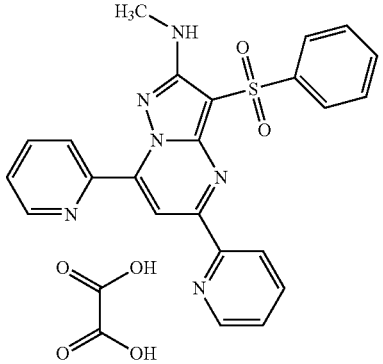 | 532.54 | 443 | |
| 1.2(6) | 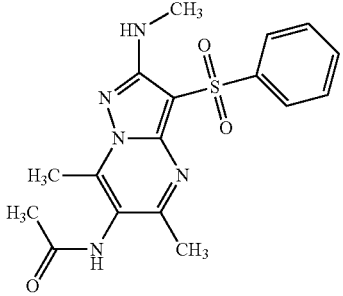 [SMILES: CNc1nn2c(C)c(NC(C)=O)c(C)nc2c1S(=O)(=O)c1ccccc1] | 373.44 | 374 | $^1$H NMR (DMSO-D$_6$, 400 MHz) δ 9.66 (s, 1H), 8.02 (m, 2H), 7.56 (m, 3H), 6.39 (q, 1H, J = 4.8), 2.92 (d, 3H, J = 4.8), 2.45 (s, 3H), 2.39 (s, 3H), 2.08 (s, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.1(1) | 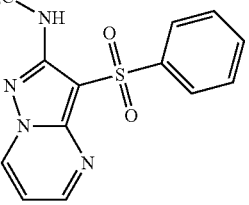 | 288.33 | 289 | $^1$H NMR (DMSO-D$_6$, 400 MHz) δ 8.96 (dd, J$_1$ = 0.8 Hz, J$_2$ = 6.8 Hz, 1H), 8.55 (dd, J$_1$ = 1.2 Hz, J$_2$ = 4.4 Hz, 1H), 8.02 (m, 2H), 7.54-7.64 (m, 3H), 7.07 (dd, J$_1$ = 4.4 Hz, J$_2$ = 6.8 Hz, 1H), 6.47(q, J = 4.0, Hz, 1H), 2.91 (d, J = 4.8 Hz, 3H). |
| 1.2.1(2) | 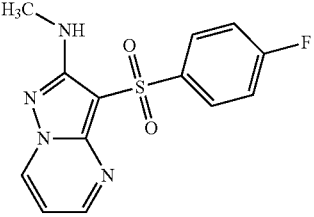 [SMILES: CNc1nn2cccnc2c1S(=O)(=O)c1ccc(F)cc1] | 306.32 | 307 | $^1$H NMR (CDCl$_3$, 400 MHz) δ 8.50 (dd, J$_1$ = 4.4 Hz, J$_2$ = 1.6 Hz, 1H), 8.45 (dd, J$_1$ = 6.8 Hz, J$_2$ = 1.6 Hz, 1H), 8.14-8.18 (m, 2H), 7.13-7.18 (m, 2H), 6.85 (dd J$_1$ = 6.8 Hz, J$_2$ = 4.4 Hz, 1H), 6.08 (q, J = 4.8 Hz, 1H), 3.06 (d, J = 4.8 Hz, 3H) |
| 1.2.1(3) | 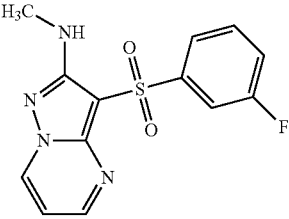 [SMILES: CNc1nn2cccnc2c1S(=O)(=O)c1cccc(F)c1] | 306.32 | 307 | |
| 1.2.1(4) | 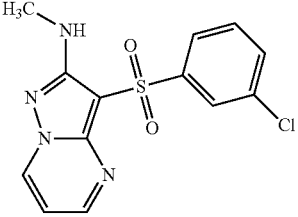 [SMILES: CNc1nn2cccnc2c1S(=O)(=O)c1cccc(Cl)c1] | 322.78 | 323 | $^1$H NMR (CDCl$_3$, 400 MHz) δ 8.53 (dd, J$_1$ = 1.6 Hz, J$_2$ = 4.4 Hz, 1H), 8.46 (dd, J$_1$ = 1.6 Hz, J$_2$ = 6.4 Hz, 1H), 8.13 (s, 1H), 8.04 (d, J = 7.6 Hz, 1H), 7.50 (d, J = 8.0 Hz, 1H), 7.43 (t, J = 8.0 Hz, 1H), 6.87 (dd, J$_1$ = 4.4 Hz, J$_2$ = 6.4 Hz, 1H), 6.07 (q, J = 5.2 Hz, 1H), 3.06 (d, J = 5.2 Hz, 3H) |
| 1.2.1(5) | 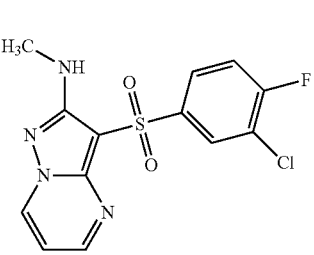 | 340.77 | 341 | |
| 1.2.1(6) | 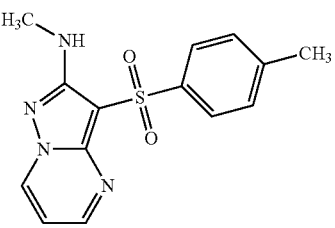 [SMILES: CNc1nn2cccnc2c1S(=O)(=O)c1ccc(C)cc1] | 302.36 | 303 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.1(7) | | 302.36 | 303 | |
| 1.2.2(1) | | 302.36 | 303 | ¹H NMR (CDCl₃, 400 MHz) δ 8.26 (d, J = 7.2 Hz, 1H), 8.16-8.18 (m, 2H), 7.46-7.56 (m, 3H), 6.67 (d, J = 6.8 Hz, 1H), 6.06 (q, J = 4.4 Hz, 1H), 3.03 (d, J = 5.2 Hz, 3H), 2.61 (s, 3H). |
| 1.2.2(2) | | 320.35 | 321 | |
| 1.2.2(3) | | 320.35 | 321 | |
| 1.2.2(4) | | 336.80 | 337 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.2(5) | | 354.79 | 355 | |
| 1.2.3(1) | | 302.36 | 303 | $^1$H NMR (CDCl$_3$, 400 MHz) δ 8.38 (d, J = 4.4 Hz, 1H), 8.13-8.15 (m, 2H), 7.45-7.54 (m, 3H), 6.69 (d, J = 4.4 Hz, 1H), 6.08 (q, J = 3.6 Hz, 1H), 3.08 (d, J = 5.2 Hz, 3H), 2.67 (s, 3H). |
| 1.2.3(2) | | 320.35 | 321 | |
| 1.2.3(3) | | 320.35 | 321 | |
| 1.2.3(4) | | 336.80 | 337 | |
| 1.2.3(5) | | 354.79 | 355 | |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2.4(1) | 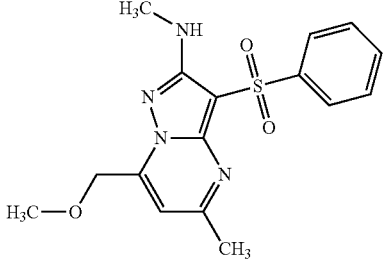 | 346.41 | 347 | ¹H NMR (CDCl₃, 400 MHz) δ 8.17 (d, 2H), 7.50 (tt, 3H), 6.84 (s, 1H), 6.05 (d, 1H), 4.77 (s, 2H), 3.57 (s, 3H), 3.03 (d, 3H), 2.62 (s, 3H). ¹³C NMR (CDCl₃, 75.48 MHz) δ 161.41, 158.09, 147.29, 144.78, 143.55, 132.01, 128.26, 126.04, 105.17, 90.58, 67.16, 59.25, 28.68, 24.78. |
| 1.2.4(2) | 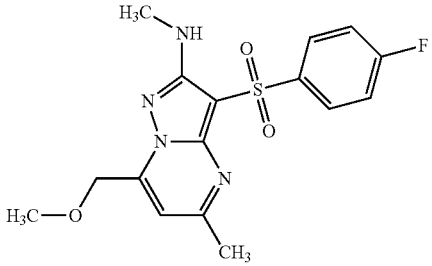 [SMILES: CNc1nn2c(COC)cc(C)nc2c1S(=O)(=O)c1ccc(F)cc1] | 364.40 | 365 | |
| 1.2.4(3) | 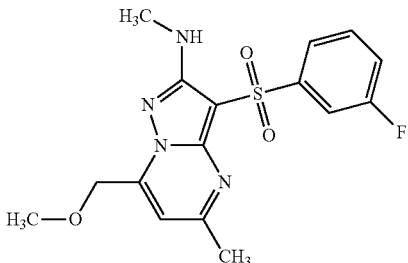 | 364.40 | 365 | |
| 1.2.4(4) | 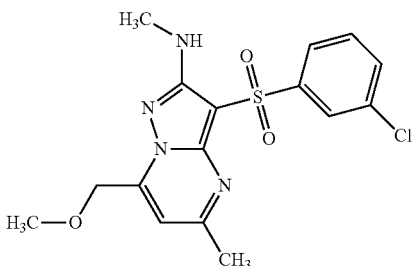 | 380.86 | 381 | |
| 1.2.4(5) | 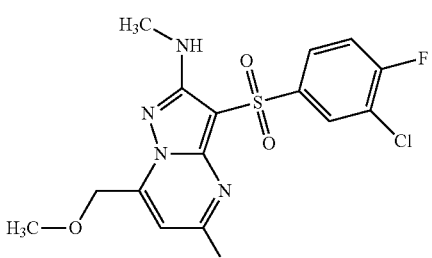 | 398.85 | 399 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.5(1) | | 346.41 | 347 | $^1$H MNR (CDCl$_3$, 400 MHz) δ 8.14 (m, 2H), 7.44-7.54 (m, 3H), 6.90 (s, 1H), 6.06 (q, J = 5.2 Hz, 1H), 4.59 (s, 2H), 3.49 (s, 3H), 3.07 (d, J = 5.2 Hz, 3H), 2.66 (s, 3H). $^{13}$C NMR (CDCl$_3$, 75.5 MHz) δ 160.74, 158.05, 147.13, 145.86, 143.49, 132.03, 128.25, 126.01, 105.66, 90.74, 74.40, 58.61, 28.66, 16.94. |
| 1.2.5(2) | | 364.40 | 365 | |
| 1.2.5(3) | | 364.40 | 365 | |
| 1.2.5(4) | | 380.86 | 381 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.5(5) | | 398.85 | 399 | |
| 1.2.6(1) | | 332.38 | 333 | $^1$H NMR (CDCl$_3$, 400 MHz) δ 8.16 (d, 2H), 7.50 (tt, 3H), 6.68 (s, 1H), 6.11 (d, 1H), 4.89 (d, 2H), 3.91 (t, 1H), 3.03 (d, 3H), 2.59 (s, 3H). |
| 1.2.6(2) | | 350.37 | 351 | |
| 1.2.6(3) | | 350.37 | 351 | |
| 1.2.6(4) | | 366.83 | 367 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.6(5) | | 384.82 | 385 | |
| 1.2.7(1) | | 332.38 | 333 | $^1$H NMR (CDCl$_3$, 400 MHz) δ 8.11 (d, 2H), 7.51 (tt, 3H), 6.64 (s, 1H), 6.05 (d, 1H), 4.74 (s, 2H), 3.08 (d, 3H), 2.66 (s, 3H). |
| 1.2.7(2) | | 350.37 | 351 | |
| 1.2.7(3) | | 350.37 | 351 | |
| 1.2.7(4) | | 366.83 | 367 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.7(5) | | 384.82 | 385 | |
| 1.2.8(1) | | 365.42 | 366 | |
| 1.2.8(2) | | 365.42 | 366 | |
| 1.2.8(3) | | 365.42 | 366 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.8(4) | | 383.41 | 384 | |
| 1.2.8(5) | | 399.86 | 400 | |
| 1.2.8(6) | | 379.44 | 380 | NMR-$^1$H (CDCl$_3$): 9.25 (s, 1H); 8.72 (d, J = 5.0 Hz, 1H); 8.45-8.48 (m, 1H); 8.18-8.21 (m, 2H); 7.44-7.55 (m, 4H); 7.13 (s, 1H); 6.15 (br. q, J = 5.0 Hz, 1H); 3.08 (d, J = 5.0 Hz, 3H); 2.73 (s, 3H). |
| 1.2.8(7) | | 379.44 | 380 | NMR-$^1$H (CDCl3): 9.25 (s, 1H); 8.72 (d, J = 5.0 Hz, 1H); 8.45-8.48 (m, 1H); 8.18-8.21 (m, 2H); 7.44-7.55 (m, 4H); 7.13 (s, 1H); 6.15 (br. q, J = 5.0 Hz, 1H); 3.08 (d, J = 5.0 Hz, 3H); 2.73 (s, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.8(8) | | 379.44 | 380 | |
| 1.2.8(9) | | 397.43 | 398 | |
| 1.2.8(10) | | 413.89 | 414 | |
| 1.2.9(1) | | 365.42 | 366 | |
| 1.2.9(2) | | 365.42 | 366 | NMR-$^1$H (CDCl3): 9.20 (d, J = 2.0 Hz, 1H); 8.77 (dd, J = 5.0 Hz, J = 1.5 Hz, 1H); 8.54 (d, J = 4.4 Hz, 1H); 8.42-8.46 (m, 1H); 8.13-8.17 (m, 2H); 7.46-7.66 (m, 4H); 6.94 (d, J = 4.4 Hz, 1H); 6.11 (br. q, J = 5.4 Hz, 1H); 3.00 (d, J = 5.4 Hz, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.9(2) •HCl | | 401.88 | 366 | NMR-¹H (DMSO-D₆): 9.32 (d, J = 2.0 Hz, 1H); 8.84 (dd, J = 5.0 Hz, J = 1.5 Hz, 1H); 8.67-8.71 (m, 1H); 8.65 (d, J = 4.4 Hz, 1H); 8.04-8.08 (m, 2H); 7.76-7.81 (m, 1H); 7.57-7.66 (m, 3H); 7.42 (d, J = 4.4 Hz, 1H); 6.58 (br. s, 1H); 2.88 (s, 3H). |
| 1.2.9(3) | | 365.42 | 366 | |
| 1.2.9(3) •HCl | | 365.42 | 366 | |
| 1.2.9(4) | | 383.41 | 384 | |
| 1.2.9(5) | | 399.86 | 400 | |
| 1.2.9(6) | | 379.44 | 380 | NMR-¹H (CDCl3): 9.15 (d, J = 2.0 Hz, 1H); 8.76 (dd, J = 4.9 Hz, J = 1.5 Hz, 1H); 8.38-8.42 (m, 1H); 8.16-8.20 (m, 2H); 7.43-7.56 (m, 4H); 6.79 (s, 1H); 6.05 (br. q, J = 5.0 Hz, 1H); 2.97 (d, J = 5.0 Hz, 3H); 2.65 (s, 3H). |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2.9(6) •HCl | 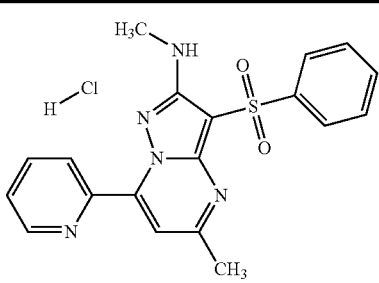 | 415.90 | 380 | NMR-¹H (DMSO-D₆): 9.27 (d, J = 1.5 Hz, 1H); 8.81 (dd, J = 5.0 Hz, J = 1.5 Hz, 1H); 8.61-8.65 (m, 1H); 8.05-8.08 (m, 2H); 7.72-7.77 (m, 1H); 7.56-7.65 (m, 3H); 7.35 (s, 1H); 6.45 (br. s, 1H); 2.86 (s, 3H); 2.59 (s, 3H). |
| 1.2.9(7) | 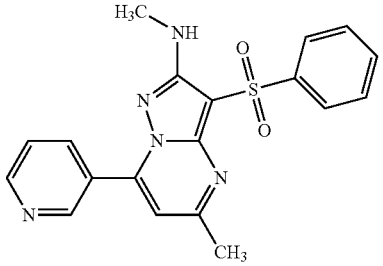 [SMILES: CNc1nn2c(-c3cccnc3)cc(C)nc2c1S(=O)(=O)c1ccccc1] | 379.44 | 380 | NMR-¹H (CDCl3): 9.15 (d, J = 2.0 Hz, 1H); 8.76 (dd, J = 4.9 Hz, J = 1.5 Hz, 1H); 8.38-8.42 (m, 1H); 8.16-8.20 (m, 2H); 7.43-7.56 (m, 4H); 6.79 (s, 1H); 6.05 (br. q, J = 5.0 Hz, 1H); 2.97 (d, J = 5.0 Hz, 3H); 2.65 (s, 3H). |
| 1.2.9(7) •HCl | 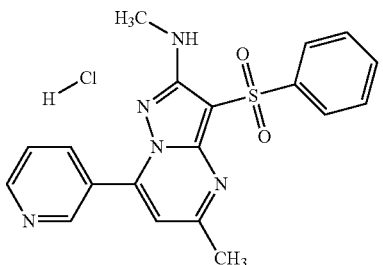 | 415.90 | 380 | NMR-¹H (DMSO-D₆): 9.27 (d, J = 1.5 Hz, 1H); 8.81 (dd, J = 5.0 Hz, J = 1.5 Hz, 1H); 8.61-8.65 (m, 1H); 8.05-8.08 (m, 2H); 7.72-7.77 (m, 1H); 7.56-7.65 (m, 3H); 7.35 (s, 1H); 6.45 (br. s, 1H); 2.86 (s, 3H); 2.59 (s, 3H). |
| 1.2.9(8) | 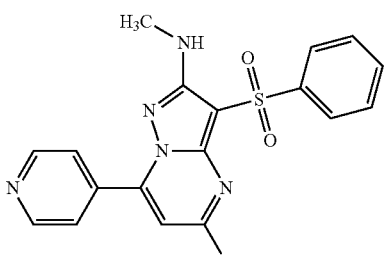 | 379.44 | 380 | |
| 1.2.9(9) | 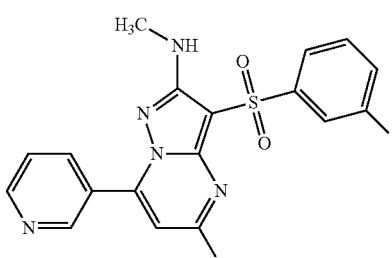 | 397.43 | 398 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.9(10) | | 413.89 | 414 | |
| 1.2.10(1) | | 332.38 | 333 | |
| 1.2.10(2) | | 395.44 | 396 | |
| 1.2.10(3) | | 395.44 | 396 | (DMSO-D$_6$, 400 MHz) δ 9.42 (s, 1H), 8.75 (d, J = 4.0 Hz, 1H), 8.59 (d, J = 8.0 Hz, 1H), 8.09 (d, J = 6.4 Hz, 2H), 7.56-7.66 (m, 4H), 7.36 (s, 1H), 6.42 (q, J = 4.4 Hz, 1H), 4.26 (s, 3H), 2.92 (d, J = 4.4 Hz, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.10(4) | | 395.44 | 396 | |
| 1.2.10(5) | | 350.37 | 351 | |
| 1.2.11(1) | | 317.37 | 318 | |
| 1.2.11(2) | | 351.82 | 352 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.11(3) | | 437.57 | 438 | |
| 1.2.11(4) | | 379.44 | 380 | |
| 1.2.11(5) | | 413.89 | 414 | |
| 1.2.11(6) | | 369.40 | 370 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.11(7) | | 403.85 | 404 | |
| 1.2.11(8) | | 432.51 | 433 | |
| 1.2.11(9) | | 466.95 | 467 | |
| 1.2.11(10) | | 450.50 | 451 | |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2.12(1) | 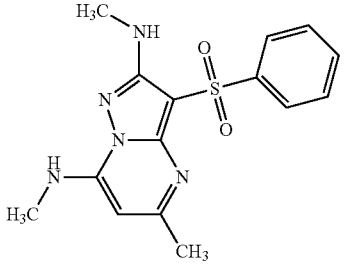 [SMILES: CNc1nn2c(NC)cc(C)nc2c1S(=O)(=O)c1ccccc1] | 331.40 | 332 | |
| 1.2.12(2) | 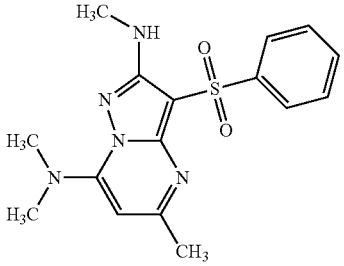 [SMILES: CNc1nn2c(N(C)C)cc(C)nc2c1S(=O)(=O)c1ccccc1] | 345.43 | 346 | |
| 1.2.12(3) | 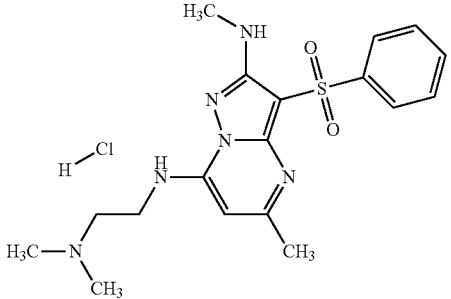 | 424.95 | 389 | NMR-¹H (DMSO-D₆): 10.07 (br. s, 1H); 8.02 (d, J = 8.0 Hz, 2H); 7.52-7.62 (m, 3H); 6.95 (s, 1H); 6.72 (br. t, J = 5.7 Hz, 1H); 3.69-3.76 (m, 2H); 3.29-3.35 (m, 2H); 2.80 (s, 6H); 2.54 (s, 3H); 2.47 (s, 3H). |
| 1.2.12(4) | 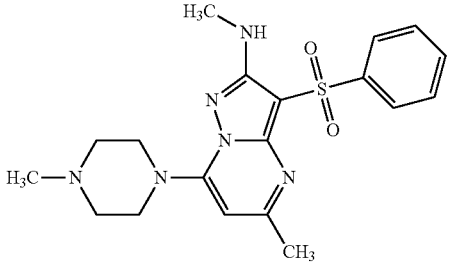 [SMILES: CNc1nn2c(N3CCN(C)CC3)cc(C)nc2c1S(=O)(=O)c1ccccc1] | 400.51 | 401 | NMR-¹H (DMSO-D₆): 11.24 (br. s, 1H); 7.99 (d, J = 8.0 Hz, 2H); 7.50-7.60 (m, 3H); 6.54 (s, 1H); 6.24 (very br. s, 1H); 4.50-4.60 (m, 4H); 3.40-3.50 (m, 4H); 2.87 (s, 3H); 2.75 (d, J = 4.3 Hz, 3H); 2.41 (s, 3H). |
| 1.2.12(4) •HCl | 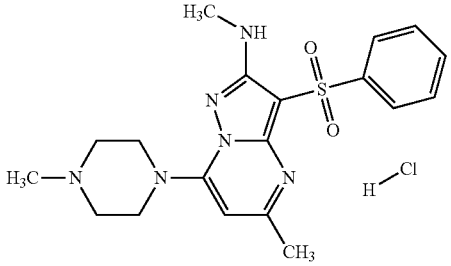 [SMILES: CNc1nn2c(N3CCN(C)CC3)cc(C)nc2c1S(=O)(=O)c1ccccc1 ; Cl] | 436.97 | 401 | NMR-¹H (DMSO-D₆): 11.24 (br. s, 1H); 7.99 (d, J = 8.0 Hz, 2H); 7.50-7.60 (m, 3H); 6.54 (s, 1H); 6.24 (very br. s, 1H); 4.50-4.60 (m, 4H); 3.40-3.50 (m, 4H); 2.87 (s, 3H); 2.75 (d, J = 4.3 Hz, 3H); 2.41 (s, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.12(4) •CH₃SO₃H | | 496.62 | 401 | |
| 1.2.12(5) | | 387.46 | 388 | |
| 1.2.12(6) | | 464.59 | 465 | |
| 1.2.12(7) | | 440.53 | 441 | |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---|---|---|---|
| 1.2.12(8) | 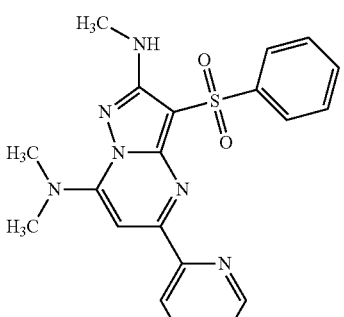 | 408.49 | 409 | |
| 1.2.12(9) | 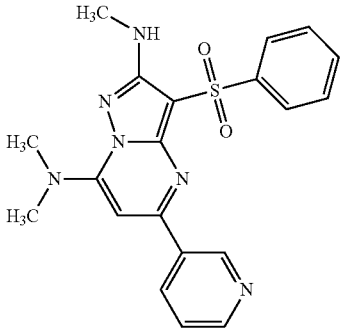 [SMILES: CNc1nn2c(N(C)C)cc(-c3cccnc3)nc2c1S(=O)(=O)c1ccccc1] | 408.49 | 409 | |
| 1.2.12(10) | 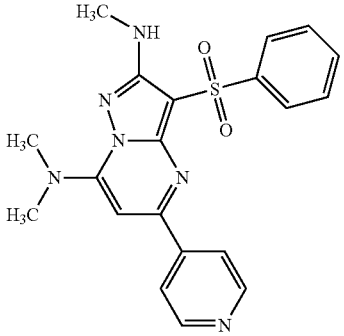 [SMILES: CNc1nn2c(N(C)C)cc(-c3ccncc3)nc2c1S(=O)(=O)c1ccccc1] | 408.49 | 409 | |
| 1.2.12(11) | 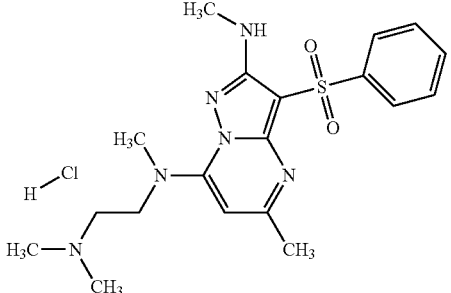 | 438.98 | 403 | NMR-$^1$H (DMSO-D$_6$): 10.46 (br. s, 1H); 8.01 (d, J = 8.0 Hz, 2H); 7.52-7.62 (m, 3H); 7.04 (s, 1H); 3.73 (t, J = 6.6 Hz, 2H); 3.36 (t, J = 6.6 Hz, 2H); 3.03 (s, 3H); 2.78 (s, 6H); 2.58 (s, 3H); 2. 48 (s, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.12(12) | | 438.98 | 403 | NMR-¹H (DMSO-D₆): 10.30 (br. s, 1H); 8.01 (d, J = 8.0 Hz, 2H); 7.52-7.62 (m, 3H); 6.92 (s, 1H); 6.52 (br. t, J = 6.1 Hz, 1H); 3.38-3.44 (m, 2H); 3.02-3.08 (m, 2H); 2.72 (s, 6H); 2.52 (s, 3H); 2.46 (s, 3H); 1.92-2.06 (m, 2H). |
| 1.2.13(1) | | 402.48 | 403 | ¹H NMR (DMSO-D₆, 400 MHz) δ 8.03 (m, 2H), 7.53-7.62 (m, 3H), 6.36 (q, J = 4.8 Hz, 1H), 4.09 (q, J = 7.2 Hz, 2H), 3.82 (s, 2H), 2.92 (d, J = 4.8 Hz, 3H), 2.60 (s, 3H), 2.49 (s, 3H), 1.18 (t, J = 7.2 Hz, 3H). |
| 1.2.13(2) | | 430.53 | 431 | |
| 1.2.13(3) | | 430.53 | 431 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.13(4) | | 444.56 | 445 | |
| 1.2.13(5) | | 420.47 | 421 | |
| 1.2.13(6) | | 436.92 | 437 | |
| 1.2.13(7) | | 416.50 | 417 | $^1$H NMR (CDCl$_3$, 400 MHz) 8.16 (m, 2H), 7.44-7.52 (m, 3H), 5.99 (q, J = 4.8 Hz, 1H), 4.15 (q, J = 7.2 Hz, 2H), 3.04 (d, J = 4.8 Hz, 3H), 2.98 (m, 2H), 2.67 (s, 3H), 2.61 (s, 3H), 2.46 (m, 2H), 1.25 (t, J = 7.2 Hz, 3H). |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---|---|---|---|
| 1.2.14(1) | 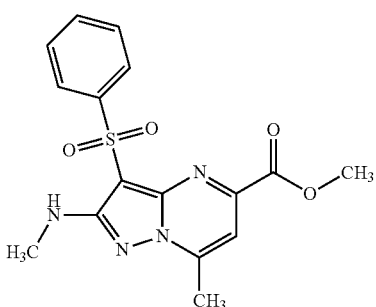 | 360.39 | 361 | |
| 1.2.15(1) | 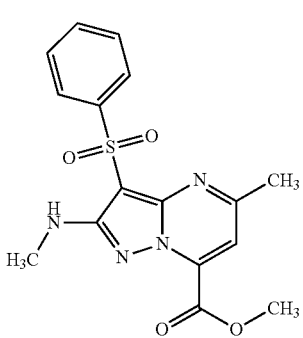 | 360.39 | 361 | |
| 1.2.16(1) | 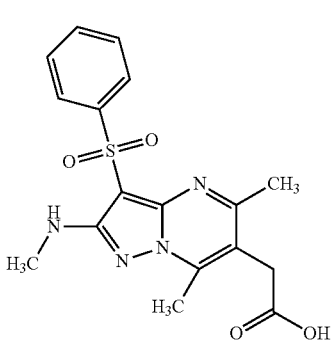 [SMILES: CNc1nn2c(C)c(CC(=O)O)c(C)nc2c1S(=O)(=O)c1ccccc1] | 374.42 | 375 | |
| 1.2.16(2) | 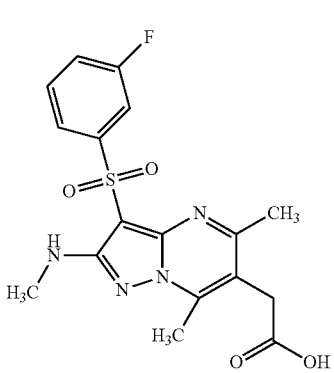 [SMILES: CNc1nn2c(C)c(CC(=O)O)c(C)nc2c1S(=O)(=O)c1cccc(F)c1] | 392.41 | 393 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.16(3) | | 408.87 | 409 | |
| 1.2.16(4) | | 388.45 | 389 | $^1$H NMR (CDCl$_3$, 400 MHz) 8.16 (d, J = 6.8 Hz, 2H), 7.45-7.53 (m, 3H), 6.01 (br, 1H), 3.05 (s, 3H), 3.01 (t, J = 7.8 Hz, 2H), 2.68 (s, 3H), 2.62 (s, 3H), 2.54 (t, J = 7.8 Hz, 2H). |
| 1.2.17(1) | | 346.37 | 347 | |
| 1.2.18(1) | | 346.37 | 347 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.19(1) •CH₃CO₂H | 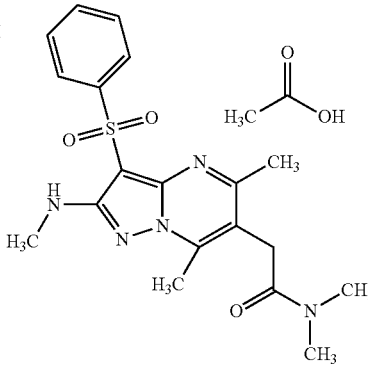 | 461.54 | 402 | ¹H NMR (400 MHz, CDCl₃): 8.128 (d, 2H, J = 7.6 Hz); 7.422-7.513 (m, 3H); 5.964 (q, 1H, J = 4 Hz); 3.638 (s, 2H); 3.211 (s, 3H); 3.041 (d, 3H, J = 4 Hz), 2.554 (s, 3H), 2.471 (s, 3H), 2.065 (s, 3H). |
| 1.2.19(2) •HCl | 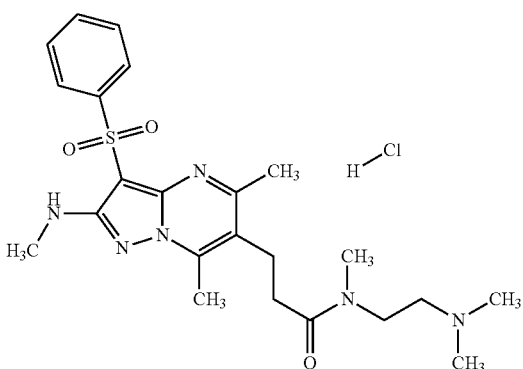 | 509.07 | 473 | ¹H NMR (DMSO-D₆, 400 MHz) δ 10.26 (br. 1H), 8.02 (m, 2H), 7.53-7.61 (m, 3H), 6.30 (q, J = 4.8 Hz, 1H), 3.65 (t, J = 6.2 Hz, 2H), 3.20 (t, J = 6.2 Hz, 2H), 2.93 (s, 3H), 2.91 (d, J = 4.8 Hz, 3H), 2.84 (t, J = 7.6 Hz, 2H), 2.77 (s, 6H), 2.63 (s, 3H), 2.56 (s, 3H), 2.54 (t, J = 7.6 Hz, 2H). |
| 1.2.19(3) •HCl | 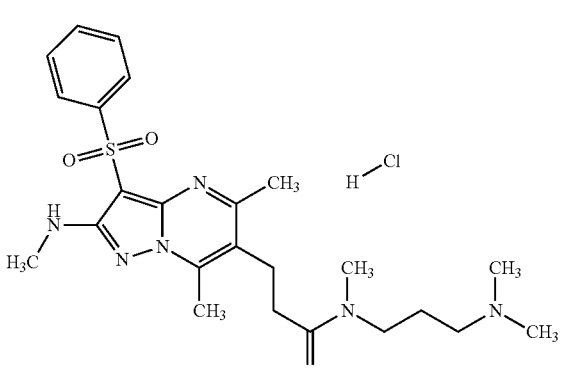 | 523.10 | 487 | ¹H NMR (DMSO-D₆, 400 MHz) δ 10.19, 10.54 (2br, 1H), 8.01 (m, 2H), 7.53-7.61 (m, 3H), 6.31 (br, 1H), 3.44 (m, 2H), 2.96 (br, 2H), 2.92 (s, 6H), 2.85 (br, 2H), 2.72 (s, 3H), 2.69 (s, 3H), 2.62 (s, 3H), 2.56 (s, 3H), 1.86 (m, 2H). |
| 1.2.19(4) •HCl | 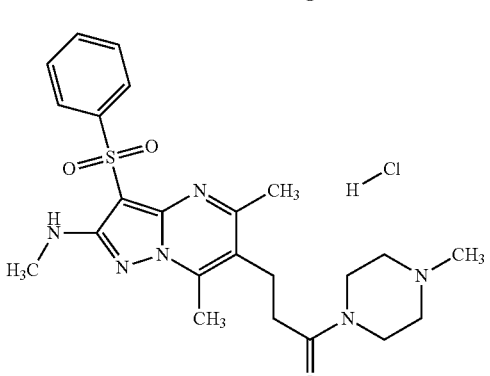 | 507.06 | 471 | ¹H NMR (DMSO-D₆, 400 MHz) δ 11.13 (br, 1H), 8.01 (d, J = 6.8 Hz, 2H), 7.53-7.61 (m, 3H), 6.31 (q, J = 4.8 Hz, 1H), 4.39 (br, 1H), 3.94 (br, 1H), 3.29 (br, 2H), 3.05 (br, 2H), 2.91 (d, J = 4.8 Hz, 3H), 2.85 (t, J = 8.0 Hz, 2H), 2.71 (s, 3H), 2.62 (s, 3H), 2.58 (t, J = 8.0 Hz, 2H), 2.56 (s, 3H). |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---|---|---|---|
| 1.2.20(1) •HCl | 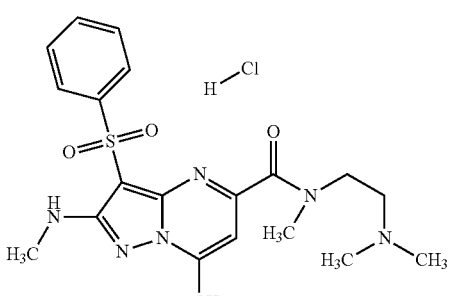 | 466.99 | 431 | |
| 1.2.21(1) •HCl | 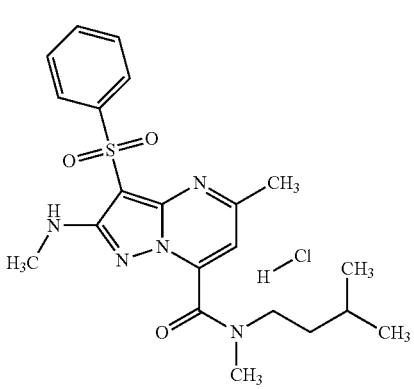 | 466.99 | 431 | |
| 1.2.22(1) •HCl | 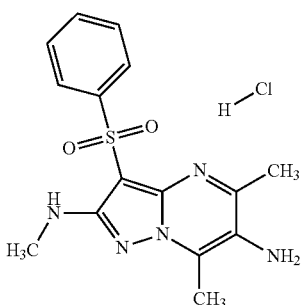 | 367.86 | 332 | $^1$H NMR (DMSO-D$_6$, 400 MHz) δ 7.98 (d, J = 8.4 Hz, 2H), 7.51-7.59 (m, 3H), 4.59 (br), 2.89 (s, 3H), 2.55 (s, 3H), 2.47 (s, 3H). |
| 1.2.22(1) •CH$_3$SO$_3$H | 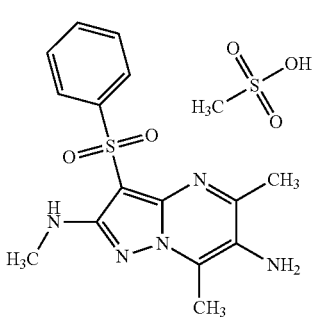 | 427.51 | 332 | $^1$H NMR (DMSO-D$_6$, 400 MHz) δ 7.98 (d, J = 7.2 Hz, 2H), 7.54 (m, 3H), 6.52 (br, 4H), 2.89 (s, 3H), 2.54 (s, 3H), 2.46 (s, 3H), 2.41 (s, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.22(2) •HCl | | 381.89 | 346 | $^1$H NMR (DMSO-D$_6$, 400 MHz) δ 8.36 (br, 3H), 8.03 (m, 2H), 7.54-7.63 (m, 3H), 6.43 (q, J = 4.8 Hz, 1H), 2.93 (d, J = 4.8 Hz, 3H), 2.74 (s, 3H), 2.66 (s, 3H). |
| 1.2.22(2) •CH$_3$SO$_3$H | | 441.54 | 346 | |
| 1.2.22(3) •HCl | | 395.91 | 360 | $^1$H NMR (DMSO-D$_6$, 400 MHz) δ 8.17 (br, 3H), 8.01 (d, J = 7.6 Hz, 2H), 7.53-7.61 (m, 3H), 2.98 (m, 2H), 2.92 (s, 3H), 2.89 (br, 2H), 2.64 (s, 3H), 2.56 (s, 3H). |
| 1.2.22(4) •HCl | | 409.94 | 374 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.22(5) •HCl | | 416.33 | 380 | ¹H NMR (DMSO, 400 MHz) δ 8.34 (br, 3H), 8.10 (t, J = 1.6 Hz, 1H), 7.97 (ddd, $J_1$ = 7.6 Hz, $J_2$ = 1.6 Hz, $J_3$ = 1.2 Hz, 1H), 7.69 (ddd, $J_1$ = 8.0 Hz, $J_2$ = 2.0 Hz, $J_3$ = 1.2 Hz, 1H), 7.61 (t, J = 8.0 Hz, 1H), 6.48 (q, J = 4.8 Hz, 1H), 4.14 (s, 2H), 2.92 (d, J = 4.8 Hz, 3H), 2.75 (s, 3H), 2.67 (s, 3H). |
| 1.2.22(5) •CH₃SO₃H | | 475.98 | 380 | |
| 1.2.22(6) •HCl | | 399.88 | 364 | |
| 1.2.22(7) •HCl | | 434.32 | 398 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.22(8) •HCl | | 430.36 | 394 | |
| 1.2.22(9) •HCl | | 413.90 | 378 | |
| 1.2.22(10) •HCl | | 409.94 | 374 | $^1$H NMR (DMSO-D$_6$, 400 MHz) δ 10.10 (br, 1H), 8.04 (m, 2H), 7.54-7.63 (m, 3H), 6.47 (q, J = 4.4 Hz, 1H), 2.93 (d, J = 4.4 Hz, 3H), 2.80 (s, 6H), 2.76 (s, 3H), 2.72 (s, 3H). |
| 1.2.22(10) •CH$_3$SO$_3$H | | 469.59 | 374 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.22(11) •HCl | | 444.39 | 408 | ¹H NMR (DMSO, 400 MHz) δ 10.1 (br, 3H), 8.10 (t, J = 2.0 Hz, 1H), 7.99 (dt, J₁ = 7.6 Hz, J₂ = 1.6 Hz, 1H), 7.70 (ddd, J₁ = 8.0 Hz, J₂ = 2.0 Hz, J₃ = 0.8 Hz, 1H), 7.61(t, J = 7.6 Hz, 1H), 6.50 (q, J = 4.8 Hz, 1H), 4.47 (d, J = 5.6 Hz, 2H), 2.93 (d, J = 4.8 Hz, 3H), 2.82 (s, 3H), 2.81 (s, 3H), 2.77 (s, 3H), 2.73 (s, 3H). |
| 1.2.22(12) •HCl | | 427.93 | 392 | |
| 1.2.22(13) •HCl | | 462.38 | 426 | |
| 1.2.22(14) •HCl | | 423.97 | 388 | ¹H NMR (DMSO-D₆, 400 MHz) δ 10.78 (br, 1H), 8.02 (d, J = 13.2 Hz, 2H), 7.53-7.62 (m, 3H), 6.34 (q, J = 4.8 Hz, 1H), 3.09 (br, 4H), 2.92 (d, J = 4.8 Hz, 3H), 2.82 (s, 6H), 2.67 (s, 3H), 2.60 (s, 3H). |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---|---|---|---|
| 1.2.22(15) •HCl | 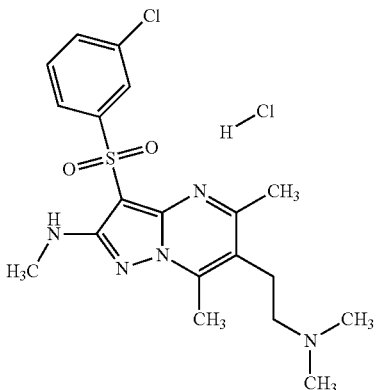 | 458.41 | 422 | |
| 1.2.22(16) •HCl | 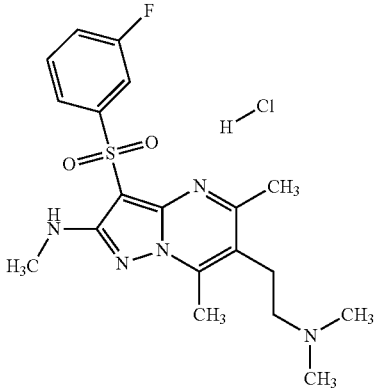 | 441.96 | 406 | |
| 1.2.22(17) •HCl | 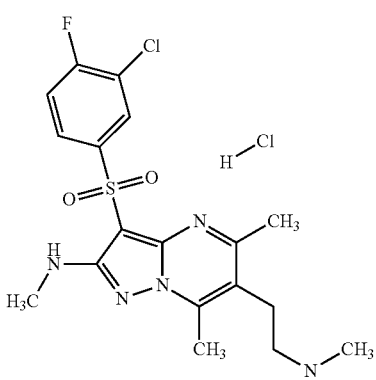 | 476.40 | 440 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.22(18) •HCl | | 423.97 | 388 | |
| 1.2.22(19) •HCl | | 464.03 | 428 | |
| 1.2.22(20) •HCl | | 515.51 | 443 | |
| 1.2.22(21) •HCl | | 506.46 | 471 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.22(22) •HCl | | 423.97 | 388 | |
| 1.2.22(23) | | 373.44 | 374 | $^1$H NMR (DMSO-D$_6$, 400 MHz) δ 9.66 (s, 1H), 8.02 (d, J = 6.8 Hz, 2H), 7.56 (m, 3H), 6.39 (q, J = 4.8 Hz, 1H), 2.92 (d, J = 4.8 Hz, 3H), 2.45 (s, 3H), 2.39 (s, 3H), 2.08 (s, 3H). |
| 1.2.22(24) | | 359.45 | 360 | |
| 1.2.22(24) •HCl | | 395.91 | 360 | $^1$H NMR (DMSO-D$_6$, 400 MHz) δ 8.02 (m, 2H), 7.53-7.61 (m, 3H), 6.29 (br, 1H), 2.91 (s, 3H), 2.74 (s, 6H), 2.57 (s, 3H), 2.49 (s, 3H). |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.22(24) •CH$_3$SO$_3$H | | 455.56 | 360 | |
| 1.2.23(1) •HCl | | 367.86 | 332 | $^1$H NMR (DMSO-D$_6$, 400 MHz) δ 8.50 (br, 3H), 8.14 (m, 2H), 7.53-7.64 (m, 3H), 7.12 (s, 1H), 6.50 (q, J = 4.4 Hz, 1H), 4.24 (br, 2H), 2.93 (d, J = 4.4 Hz, 3H), 2.62 (s, 3H). |
| 1.2.23(2) •HCl | | 385.85 | 350 | |
| 1.2.23(3) •HCl | | 381.89 | 346 | |
| 1.2.23(4) •HCl | | 395.91 | 360 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.23(5) •HCl | (structure) | 402.30 | 366 | |
| 1.2.23(6) •HCl | (structure) | 385.85 | 350 | |
| 1.2.23(7) •HCl | (structure) | 420.29 | 384 | |
| 1.2.23(8) •HCl | (structure) | 416.33 | 380 | |
| 1.2.23(9) •HCl | (structure) | 399.88 | 364 | |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2.23(10) •HCl | 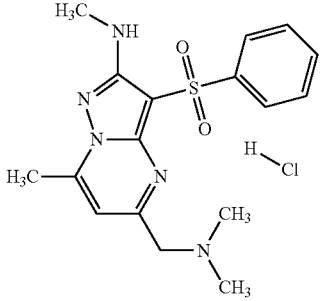 | 395.91 | 360 | |
| 1.2.23(11) •HCl | 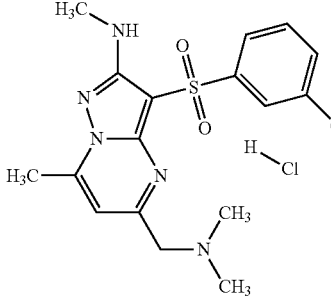 | 430.36 | 394 | |
| 1.2.23(12) •HCl | 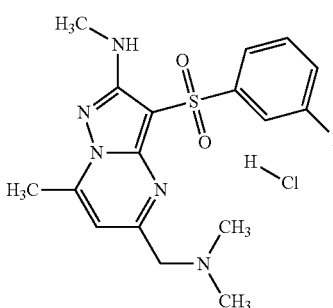 | 413.90 | 378 | |
| 1.2.23(13) •HCl | 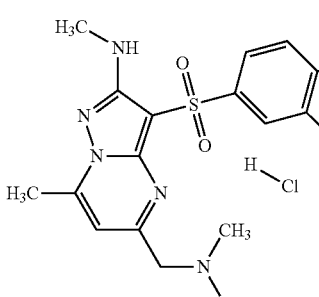 | 448.35 | 412 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---------|-------------|-------------------|-----|
| 1.2.23(14) •HCl | | 409.94 | 374 | |
| 1.2.23(15) •HCl | | 444.39 | 408 | |
| 1.2.23(16) •HCl | | 427.93 | 392 | |
| 1.2.23(17) •HCl | | 462.38 | 426 | |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---|---|---|---|
| 1.2.24(1) •HCl | 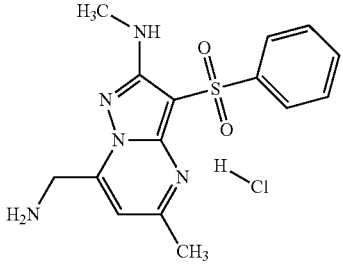 | 367.86 | 332 | ¹H NMR (DMSO-D₆, 400 MHz) δ 8.76 (br, 3H), 8.03 (m, 2H), 7.59 (m, 3H), 7.15 (s, 1H), 6.51 2.95 (d, J = 2.8 Hz, 3H), 2.56 (s, 3H). |
| 1.2.24(2) •HCl | 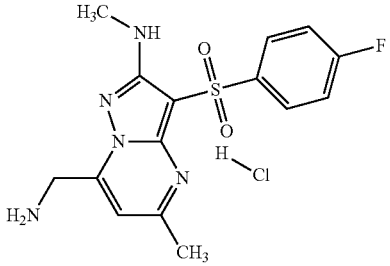 | 385.85 | 350 | |
| 1.2.24(3) •HCl | 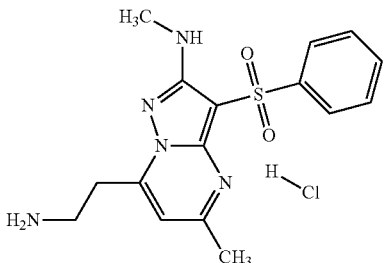 | 381.89 | 346 | ¹H NMR (DMSO-D₆, 400 MHz) δ 8.09 (br, 3H), 8.03 (m, 2H), 7.54-7.63 (m, 3H), 6.96 (s, 1H), 6.41 (q, J = 3.6 Hz, 1H), 3.29 (br, 4H), 2.92 (d, J = 3.6 Hz, 3H), 2.51 (s, 3H). |
| 1.2.24(4) •HCl | 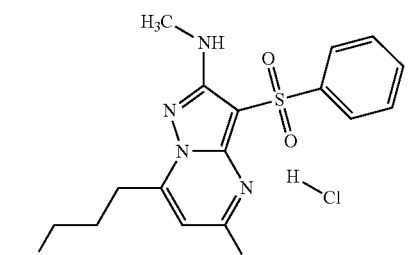 | 395.91 | 360 | |
| 1.2.24(5) •HCl | 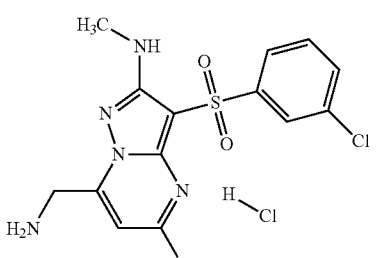 | 402.30 | 366 | |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2.24(6) •HCl | 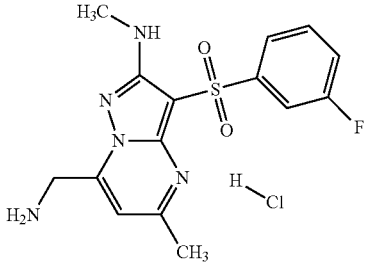 | 385.85 | 350 | |
| 1.2.24(7) •HCl | 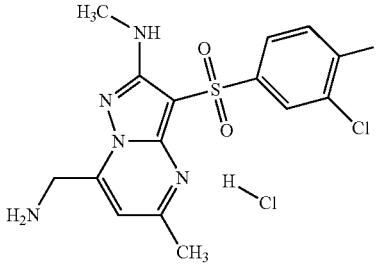 | 420.29 | 384 | |
| 1.2.24(8) •HCl | 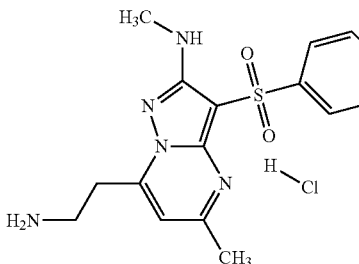 | 416.33 | 380 | |
| 1.2.24(9) •HCl | 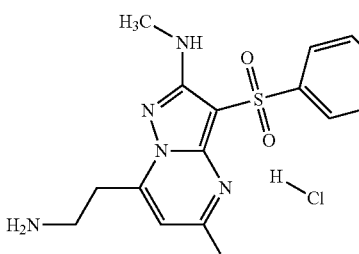 | 399.88 | 364 | |
| 1.2.24(10) •HCl | 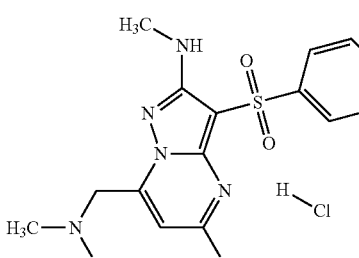 | 395.91 | 360 | $^1$H NMR (DMSO-D$_6$, 400 MHz) δ 10.94 (br, 1H), 8.04 (m, 2H), 7.55-7.64 (m, 3H), 7.37 (s, 1H), 6.51 (br, 1H), 4.69 (s, 2H), 2.95 (br, 3H), 2.86 (s, 6H), 2.56 (s, 3H). |

TABLE 3-continued
Substituted 2-alkylamino-3-arylsulfonyl-pyrazolo[1,5-a]pyrimidines of the general formula 1.2.
| № | Formula | Mol. weight | LCMS, m/z (M + 1) | NMR |
|---|---------|-------------|-------------------|-----|
| 1.2.24(11) •HCl | 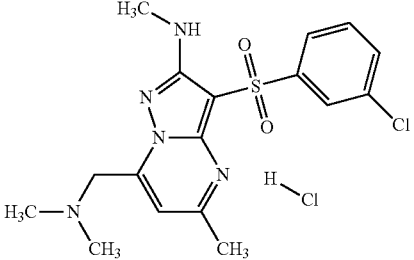 | 430.36 | 394 | |
| 1.2.24(12) •HCl | 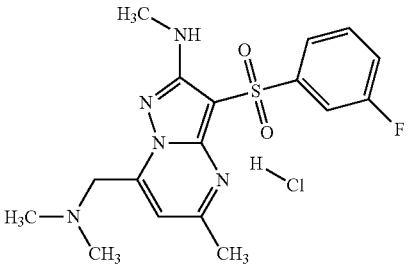 | 413.90 | 378 | $^1$H NMR (DMSO-D$_6$, 400 MHz) δ 10.22 (br, 1H), 7.87 (t, J = 7.6 Hz, 1H), 7.64 (td, J$_1$ = 8.0 Hz, J$_2$ = 5.6 Hz, 1H), 7.49 (td, J$_1$ = 8.4 Hz, J$_2$ = 2.0 Hz, 1H), 6.48 (q, J = 4.0 Hz, 1H), 4.47 (d, J = 5.6 Hz, 2H), 2.93 (d, J = 4.0 Hz, 3H), 2.81 (d, J = 2.8 Hz, 6H), 2.77 (s, 3H), 2.73 (s, 3H). |
| 1.2.24(13) •HCl | 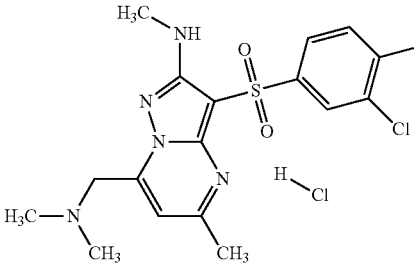 | 448.35 | 412 | |
| 1.2.24(14) •HCl | 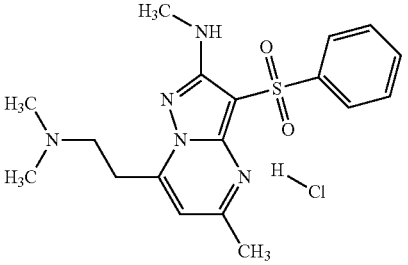 | 409.94 | 374 | $^1$H NMR (DMSO-D$_6$, 400 MHz) δ 10.40 (br, 1H), 8.03 (m, 2H), 7.54-7.63 (m, 3H), 7.01 (s, 1H), 6.44 (q, J = 4.8 Hz, 1H), 3.49 (t, J = 7.0 Hz, 2H), 3.41 (t, J = 7.0 Hz, 2H), 2.93 (d, J = 4.8 Hz, 3H), 2.81 (s, 6H), 2.51 (s, 3H). |
| 1.2.24(15) •HCl | 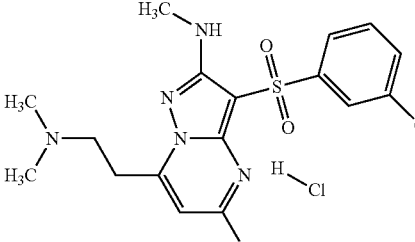 | 444.39 | 408 | |

TABLE 3-continued

Substituted 2-alkylamino-3-arylsulfonyl-pyrazolo[1,5-a]pyrimidines of the general formula 1.2.

| № | Formula | Mol. weight | LCMS, m/z (M + 1) | NMR |
|---|---|---|---|---|
| 1.2.24(16) •HCl | 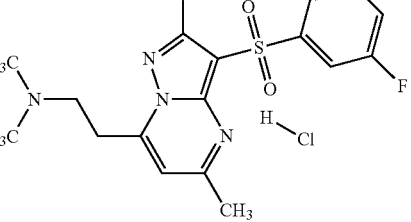 | 427.93 | 392 | |
| 1.2.24(17) •HCl | 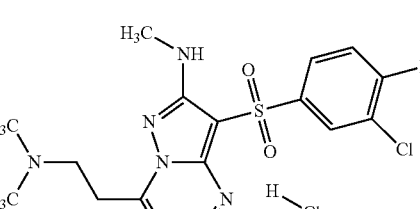 | 462.38 | 426 | |
| 1.2.22(18) | 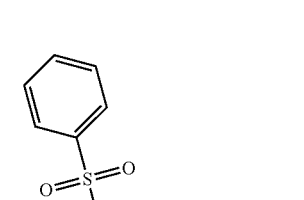 | 359.45 | 360 | $^1$H NMR (DMSO-D$_6$, 400 MHz) δ 8.01 (m, 2H), 7.56 (m, 3H), 5.43 (br. m, 1H), 2.90 (s, 3H), 2.73 (s, 6H), 2.56 (s, 3H), 2.48 (s, 3H). |

EXAMPLE 9

Determination of antagonistic activity of compounds of the general formula 1 towards 5-HT$_6$ receptors. Compounds of the general formula 1 were tested for their ability to prevent 5-HT$_6$ receptors activation by serotonin. HEK 293 cells (cells of human embryo's kidney) with artificially expressed 5-HT$_6$ receptor, activation of which by serotonin leads to increasing the concentration of intracellular cAMP, were used. The level of intracellular cAMP was determined using reagent kit LANCE cAMP (PerkinElmer) according to the method described by the manufacturer of the kit [http://las.perkinelmer.com/content/Manuals/MAN_LANCEcAMP384KitUser.pdf]. Effectiveness of the compounds was estimated by their ability to reduce the level of intracellular cAMP induced by serotonin. Table 4 presents IC$_{50}$ values for the compounds of general formula 1 in the setting of functional assay for serotonin 5-HT$_6$ receptor inhibition. The data given testify their moderate or high antagonistic activity.

TABLE 4

IC$_{50}$ Values for antagonists of the general formula 1 in the setting of functional assay for serotonin 5-HT$_6$ receptor inhibition.

| No | IC$_{50}$, nM |
|---|---|
| 1.1(4) | 300 |
| 1.1(5) | 8,400 |
| 1.1(6) | >10,000 |
| 1.1(7) | 514 |
| 1.1(10) | 4,500 |
| 1.1(11) | 30.0 |
| 1.1.1(1) | 5,200 |
| 1.1.1(3) | 473 |
| 1.1.1(4) | 912 |
| 1.1.1(6) | 2,200 |
| 1.1.1(7) | 1,870 |
| 1.1.2(1) | 450 |
| 1.1.2(2) | 996 |
| 1.1.2(5) | 187 |
| 1.1.3(1) | 1,110 |
| 1.1.3(5) | 156 |

TABLE 4-continued

IC$_{50}$ Values for antagonists of the general formula 1 in the setting of functional assay for serotonin 5-HT$_6$ receptor inhibition.

| No | IC$_{50}$, nM |
|---|---|
| 1.1.5(1) | 414 |
| 1.1.6(1) | 73 |
| 1.1.7(1) | 177 |
| 1.1.8(2) | 30,100 |
| 1.1.8(3) | <10 |
| 1.2(1) | 52 |
| 1.2(4) | 723 |
| 1.2.1(1) | 76 |
| 1.2.1(2) | 45 |
| 1.2.1(4) | 24 |
| 1.2.2(1) | 16 |
| 1.2.3(1) | 3.0 |
| 1.2.4(1) | 101 |
| 1.2.5(1) | 4.0 |
| 1.2.6(1) | 4.0 |
| 1.2.7(1) | 19 |
| 1.2.8(8) | 4.0 |
| 1.2.9(2) | 1,037 |
| 1.2.9(7) | 341 |
| 1.2.10(3) | 12.0 |
| 1.2.11(1) | 12.0 |
| 1.2.12(1) | 9.0 |
| 1.2.12(2) | 12.0 |
| 1.2.12(3) | 1,549 |
| 1.2.12(4).HCl | 173 |
| 1.1.12(5) | 197 |
| 1.2.12(9) | 13.0 |
| 1.2.12(11) | 172 |
| 1.2.12(12) | 1,858 |
| 1.2.19(2).HCl | 1,683 |
| 1.2.19(3).HCl | 2,277 |
| 1.2.19(4).HCl | 6,059 |
| 1.2.22(1).HCl | 11.33 |
| 1.2.22(2).HCl | 9.0 |
| 1.2.22(3).HCl | 45.0 |
| 1.2.22(4).HCl | 78.0 |
| 1.2.22(5).HCl | 10.0 |
| 1.2.22(6).HCl | 25.19 |
| 1.2.22(10).HCl | 26.0 |
| 1.2.22(11).HCl | 22.0 |
| 1.2.22(14).HCl | 56.4 |
| 1.2.22(24).HCl | 6.0 |
| 1.2.23(2).HCl | 37.0 |
| 1.2.23(10).HCl | 60.0 |
| 1.2.23(11).HCl | 67.0 |
| 1.2.23(12).HCl | 70.0 |
| 1.2.24(1).HCl | 15.0 |
| 1.2.24(2).HCl | 22.0 |
| 1.2.24(3).HCl | 30.0 |
| 1.2.24(10).HCl | 21.0 |
| 1.2.24(11).HCl | 33.0 |
| 1.2.24(12).HCl | 35.0 |
| 1.2.24(14).HCl | 899 |

EXAMPLE 10

Determination of activity of the compounds of the general formula 1 in the setting of competitive binding to serotonin 5-HT$_6$ receptors.

Screening of the disclosed compounds for their potential ability to interact with serotonin 5-HT$_6$ receptors was carried out by method of radioligand binding. For this purpose membrane species were prepared from expressing recombinant human 5-HT$_6$ receptors HeLa cells by means of their homogenization in glass homogenizer with subsequent separation of plasmatic membranes from cell nucli, mitochondria's and cell wreckages by differential centrifugation. Determination of tested compounds binding to 5-HT$_6$ receptors was carried out according to the method described in [Monsma F J Jr, Shen Y, Ward R P, Hamblin M W and Sibley D R, Cloning and expression of a novel serotonin receptor with high affinity for tricyclic psychotropic drugs. Mol. Pharmacol. 43:320-327, 1993]. In the preferred embodiment membrane preparations were incubated with radioligand (1.5 nM [$^3$H] Lysergic acid diethylamide) without and in the presence of investigated compounds for 120 min at 37° C. in the medium consisting of mM Tris-HCl, pH 7.4, 150 mM NaCl, 2 mM Ascorbic Acid, 0.001% BSA. After incubation the samples were filtered in vacuo on glass-microfiber filters G/F (Millipor, USA), filters were washed three times with cold solution of the medium and radioactivity was measured by scintillation counter MicroBeta 340 (PerkinElmer, USA). Nonspecific binding which made up 30% of overall binding was determined by incubation of membrane preparations with radioligand in the presence of 5 µM Serotonin (5-HT). Methiothepin was used as positive control. Binding of the tested compounds to the receptor was determined by their ability to displace the radioligand and expressed in percent of displacement. The percent of displacement was calculated according to the following equation:

$$\% I = \frac{TA - CA}{TA - NA} * 100,$$

wherein: TA—was overall radioactivity in the presence of radioligand only, CA—was radioactivity in the presence of radioligand and tested compound and NA—was radioactivity in the presence of radioligand and Serotonin (5 µM).

Table 5 presents the test results for the compounds of the general formula 1 in the setting of competitive binding to serotonin 5-HT$_6$ receptors, testifying their high activity towards serotonin 5-HT$_6$ receptors.

TABLE 5

IC$_{50}$ Values for antagonists of the general formula 1 in the setting of competitive assay of serotonin 5-HT$_6$ receptor inhibition.

| No | IC$_{50}$, nM |
|---|---|
| 1.1(4) | <10 |
| 1.1(5) | 50 |
| 1.1(6) | 50 |
| 1.1(2) | 1,300. |
| 1.1.2(2) | 50 |
| 1.1.3(1) | 40 |
| 1.1.8(3) | <10 |
| 1.2.1(2) | 18.0 |
| 1.2.1(4) | 5.01 |
| 1.2.3(1) | 0.74 |
| 1.2.4(1) | 0.34 |
| 1.2.7(1) | 0.88 |
| 1.2.10(3) | <10 |
| 1.2.11(1) | 0.293 |
| 1.2.12(3) | 69.9 |
| 1.2.12(4).HCl | 4.19 |
| 1.2.12(5) | 31.04 |
| 1.2.13(3) | 1.28 |
| 1.2.19(1).CH$_3$CO$_2$H | 15.3 |
| 1.2.19(2).HCl | 174 |
| 1.2.19(3).HCl | 291 |
| 1.2.19(4).HCl | 306 |
| 1.2.22(1).HCl | 0.67 |
| 1.2.22(2).HCl | 0.56 |
| 1.2.22(3).HCl | 0.645 |
| 1.2.22(5).HCl | 0.227 |
| 1.10(6).HCl | 0.551 |
| 1.10(10).HCl | 1.23 |
| 1.10(11).HCl | 0.29 |

TABLE 5-continued

IC$_{50}$ Values for antagonists of the general formula 1 in the setting of competitive assay of serotonin 5-HT$_6$ receptor inhibition.

| No | IC$_{50}$, nM |
|---|---|
| 1.10(14).HCl | 1.48 |
| 1.10(24).HCl | 0.217 |
| 1.12(1).HCl | 1.17 |
| 1.12(10).HCl | 1.67 |

The data presented in Tables 4 and 5 give evidence that the compounds of the general formula 1 could be used as "molecular tools" for investigation of peculiarities of physiologically active compounds possessing property to inhibit serotonin 5-HT$_6$ receptors and as an active ingredient for pharmaceutical compositions and medicaments.

EXAMPLE 11

Preparation of pharmaceutical composition in the form of tablets. Starch (1600 mg), ground lactose (1600 mg), talk (400 mg) and compound 1.2.22(1) (1000 mg) were mixed together and pressed into bar. The resultant bar was comminuted into granules and sifted through sieve to collect granules of 14-16 mesh. The granules thus obtained were shaped into tablets of suitable form weighing 560 mg each.

EXAMPLE 12

Preparation of pharmaceutical composition in the form of capsules. The compound 1.2.22(1) and lactose powder were carefully mixed in ratio 2:1. The resultant powdery mixture was packed into gelatin capsules of suitable size by 300 mg to capsule.

EXAMPLE 13

Preparation of pharmaceutical composition in the form of injectable compositions for intramuscular, intraperitoneal or hypodermic injections. Compound 1.2.22(1) (500 mg), chlorobutanol (300 mg), propylene glycol (2 ml), and injectable water (100 ml) were mixed together. The resultant solution was filtered and placed into 1 ml ampoules, which were sealed and sterilized in autoclave.

EXAMPLE 14

Anti-Amnestic activity (nootropic action) of compounds 1(1), 1.1.7(1), 1.2.7(1), 1.2.22(1) and 1.2.22(18).
14.1. Amnesia scopalamine model.
14.1.1. Passive Avoidance of mice in the Shuttle Chamber. The experiments were carried out in aged male mice of BALB/c line weighing 20-24 g or male rats weighing 200-250 g.

A shuttle chamber (Ugo Basile, Italy) that consisted of two sections was used. One section was white and lightened, the other one was dark. The sections were connected through a hole which could be overlapped by automatic vertical door. The floor of the dark section was made of transverse metal bars on which DC current impulses could be fed.

On the first day of testing 30 minutes before training the animals were injected intraperitoneally with Scopolamine which causes disturbance of training (memory loss). The animals of the trial group were additionally administered with one of the tested compounds. The animals of the control group were injected with physiological solution. Each group consisted of 8 animals. The animals were placed in the light section, and latent period of the first entry into the dark chamber was registered. Then vertical door was closed and the animal was punished by 0.6 mA DC current for 3 seconds. After that the animal was taken back to its home cage. In 22-24 hours the same animal was placed again in the light section of the shuttle chamber and latent period of its first entry into the dark section, the total time of its stay in the light section and the number of entries into the dark section were registered. Each monitoring lasted for 5 minutes.

The animals of the control group, having been punished in the dark section, showed successful learning ability, which was expressed in prolongation of latent period of its entry into the dark section, duration of its stay in the light section and decreasing the number of entries into the dark section in comparison with the group of animals which had not been punished. Scopolamine causes so-called anterograde amnesia, which is characterized by disfunction of new events fixation in long-term memory. It was expressed in the form of statistically significant prolongation of latent period of entry into the dark section, decreasing the total time of stay in the light section and increasing the number of entries into the dark section.

The test results are shown in FIG. 1, 2, 3, 4, 5, 6, from which it becomes apparent that the compounds 1(1), 1.2.7(1) and 1.2.22(18) have the property to decrease amnesia (to enhance memory), caused by Scopolamine.

14.1.2. Novel object recognition test. The test was carried out in aged male mice of SHK line. A plexiglass plus maze, consisted of 4 dead-end chambers (numbered 1, 2, 3, 4), joined together through the fifth central chamber, was used in the experiments. A mouse was placed into the central chamber and allowed to explore the maze. The floor was cleaned after each animal. The sequence of chamber entries and duration of visits were registered by the observer. The test was ended after 13 entries into the dead-end chambers. Criterion for entry was a location of all animal's paws inside the chamber at the same time.

During the training the animal was placed in the maze with one equiform bowl in each side chamber. In the course of testing (one hour after training) two opposite standing bowls were replaced by identical flasks, and the animal was allowed to explore the maze. The time spent by the animal in each side chamber was registered during the periods of training and testing. Index of novel object recognition was calculated as the ratio of time spent by the animal in the side chambers with novel objects to the total time spent by it in all side chambers. In comparison with the training phase the appearance of novel object extends the time spent by the animal in the chamber with novel object (so-called effect of novel object recognition). The recognition of novel objects was disturbed under the action of Scopolamine administered in 1 mg/kg dose intraperitoneally 30 minutes before training, and recognition index was decreased. However, this influence of Scopolamine could be prevented by intraperitoneal administration of Dimebon (0.1 mg/kg) 5 minutes before training, Tacrine (10 mg/kg) 30 minutes before training and compounds 1.2.7(1), 1.2.22(1) and 1.2.22(18) 60 minutes before training. The data presented in FIG. 7 testify that compounds 1.2.7(1), 1.2.22(1) and 1.2.22(18) prevent memory impairment caused by Scopolamine.

14.2. Model of amnesia caused by MK-801.
14.2.1. Passive Avoidance of mice in the Shuttle Chamber. The test was carried out as in example 14.1.1. On the first day of the test 30 minutes before training the mice were injected intraperitoneally with physiological solution of MK-801 (0.1 mg/kg), causing amnesia. Preliminary introduction of MK-801 reduces considerably the training effect, in other words it caused anterograde amnesia. In parallel, physiological solution of MK-801 in combination with active ingredients 1(1), 1.1.7(1), 1.2.22(18), 1.2.7(1) and 1.2.22(1) was injected intraperitoneally to independent groups of mice before training.

The results shown in FIGS. 8, 9, 10, 11, 12 and 13 testify that compounds 1(1), 1.1.7(1), 1.2.22(18), 1.2.7(1) and 1.2.22(1) exhibit the property to decrease amnesia caused by MK-801.

EXAMPLE 15

Anxiolytic activity of compounds 1.1(11), 1.2.7(1), 1.2.6(1), 1.2.3(1), 1.2.11(1), 1.2.22(1), 1.2.22(18) in test "Mice Behavior in the Elevated Plus Maze". The experiments were carried out in aged male mice of BALB/c line weighing about 25 g. The animals were housed 5-7 per cage with water and food available. None of the animals was acquainted with the experimental set-up before. Each experimental group included 8 animals.

The procedure used was described earlier by Lister (Lister R. G. The use of a plus-maze to measure anxiety in the mouse. Psychopharmacology, 1987; 92:180-185). Plexiglass set-up consisted of two opened arms of 30×5 cm size and two closed arms of 30×5×15 cm size. Side arms were closed with transparent plexiglass and were connected with the central zone via a platform of 5×5 cm size. The opened arms, central platform and floor were made of black plexiglass. The set-up was mounted on a metallic base which was placed 38.5 cm above the floor level.

The animals were injected intraperitoneally with placebo, Buspirone (5 mg/kg, 30 minutes before training), Lorazepam (0.05 mg/kg, 60 minutes before training) or with one of the tested compounds 1.1(11), 1.2.7(1), 1.2.6(1), 1.2.3(1), 1.2.11(1), 1.2.22(1), 1.2.22(18). Buspirone and Lorazepam were introduced in a maximal effective dose, at which side sedative effect and general decrease of exploratory activity (the number of arm entries during the test) were not observed yet.

Each mouse was placed in the maze center with its head towards the opened arm. Over a period of 5 minutes the sequence and duration of arm entries were registered by means of a computer program. Criterion for entry is a location of all animal's paws inside the arm at the same time. The index of preference was calculated as a ratio of the time spent by the animal in the opened arms as well as the number of entries into the opened arms to the total time spent by it in the opened and closed arms or, respectively, to the whole number of entries to the arms of both types. The number of defecations left by a mouse was regarded as an additional parameter characterizing the anxiety state. Being in normal state the animals usually avoid open arms (the preference index is between 0.2 and 0.3).

Test results are shown in FIGS. 14, 15 and 16, which testify that the control compounds (Buspirone and Lorazepam) produce well-marked anxiolytic effect in the test "Mice Behavior in the Elevated Plus Maze", compounds 1.2.11(1) and 1.2.22(18) exhibit anxiolytic activity analogous to the activity of control compounds.

EXAMPLE 16

Antipsychotic activity of compounds 1.2.22(1), 1.2.22(18), 1.2.7(1) in test "Prepulse inhibition of the startle response in mice". Mice of SHK line weighing about 24-30 g were used in the test. The experiments were carried out during the light period of animal's diurnal. Apomorphine hydrochloride and Haloperidol were received from Sigma Chemicals Company, (USA). Apomorphine hydrochloride was dissolved in 0.1% solution of ascorbic acid prepared with sterilized water; it was introduced subcutaneously 15 minutes before the test. Haloperidol was dissolved in sterilized water using emulsifier Twin 80, it was introduced intraperitoneally 60 minutes before the test. Compounds 1.2.22(1), 1.2.22(18), 1.2.7(1) were dissolved in sterilized water and introduced intraperitoneally 60 minutes before the test. The injection volume was 10 ml/kg. 0.1%. Solution of ascorbic acid, prepared with sterilized water and Twin 80, was injected to control group of animals.

The test instrument consisted of a chamber made of transparent plexiglass (manufacturer—Columbia Instruments Company, USA) and placed on the platform; the latter was lodged inside the sound insulating chamber. A high frequency sound column transmitting acoustic stimuluses was located 2 cm away from the platform. Startle of the animal resulted in vibrations of the platform, which were detected by analog converter and registered by computer. The level of background noise made up 65 dB. Each animal received 4 stimuli of single testing (pulse) stimulus of 50 ms duration and 105 dB or prepulsory stimulus (pre-pulse) of 20 ms duration and 85 dB, after which in 30 ms pulse stimulus of 50 ms duration and 105 dB followed. Time interval between repeated pulse or prepulse in combination with pulse stimuli made up 10 s. Inhibition of the startle in reply to prepulse-plus-pulse stimulus was calculated in percentage towards amplitude of startle in response to isolated pulse stimulus. Test results are shown in FIG. 17. The data obtained show that in mice in normal state prepulse inhibition of startle is amounted to 53%. Administration of Apomorphine, which is used in experiments on animals for modelling of psychoto-like conditions, caused reduction of prepulse inhibition of startle, which reflected the lowering of CNS ability to filter sensory stimulus. Haloperidol (1 mg/kg) and all tested compounds 1.2.22(1), 1.2.22(18), 1.2.7(1) (1 mg/kg) prevented disturbance of prepulse inhibition of startle caused by Apomorphine.

EXAMPLE 17

Antidepressant activity of compounds 1.2.7(1) and 1.2.22(18).

17.1. Mice Behavior in Porsolt's Forced Swim Test. Expression of behavioral despair was offered to use as a model for investigation of antidepressant activity in Porsolt's test (1977, 1978). That is, the behavior of a mouse or rat in a closed basin, from which the animal can not get out, characterizes the level of its despair which could be reduced by means of antidepressant intake.

Male mice of BALB/c line weighing about 20-30 g were used in the test. The animals were placed for 15 minutes in the basin (of 300 mm height, 480 mm diameter) filled with water to 70% of its volume at 25° C. In 3-5 minutes swimming activity began to decrease and change by phases of movement and immobility. The animal was considered to be motionless if it did not move during 1.5 seconds. Data for the last 5 minutes of the test were taken for the analysis. Automated computerized detection of motion with videosystem and Any-maze program were used in the test. The tested compounds 1.2.7(1) and 1.2.22(18) were injected intraperitonelly for 4 days subchronically. Test results shown in FIG. 18 testify that in this test compound 1.2.7(1) exhibits antidepressant activity.

17.2. Mice behavior in tail suspension test. Tail suspension test was described by Steri et al. (1985) as a convenient method for investigation of potential antidepressants. It is supposed that forced immobility in rodents could be used as a model for investigation of depressive disorders at humans. Clinically effective antidepressants lower mice immobility which follows negative attempts to become free when their tails are fixed.

Male mice of BALB/c line weighing about 20-30 g were used in the test. The animals were suspended by tail with a sticky tape on the holder over a horizontal surface at a height of about 40 cm, and the total duration of complete immobility episodes was registered in the course of 3 minutes. The animal was considered to be immobile if it did not make any movements during 1.5 seconds. Automated computerized detection of motion with videosystem and Any-maze program were used in the test. The tested compounds 1.2.7(1) and 1.2.22(18) were administered intraperitoneally during 4 days. Reference substances (Fluoxetine, Desipramine) were injected intraperitoneally 15 minutes before the beginning of the test.

Test results represented in FIG. 19, testify that under the conditions of the experiment compound 1.2.7(1) exhibits antidepressant activity comparable with the activity of Fluoxetine and Desipramine.

Industrial Applicability

The invention could be use in medicine, veterinary, biochemistry.

The invention claimed is:

1. A compound of the general formula 1, or a pharmaceutically acceptable salt thereof,

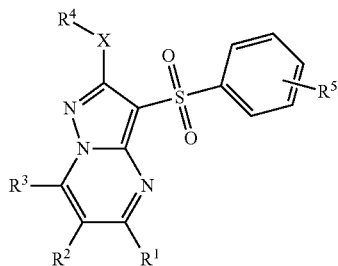

1 wherein: X=S, SO, NH;
$R^1$ is hydrogen, —$CH_3$, —$CH_2OH$, an optionally substituted $C_2$-$C_3$alkyl, cycloalkyl, adamantyl, optionally substituted aryl or 5-6 membered optionally annelated heterocyclyl, in which a heteroatom is selected from nitrogen or oxygen, alkoxycarbonyl, carboxyl, amide group;
$R^2$ is hydrogen, halogen, optionally substituted $C_1$-$C_3$alkyl, substituted hydroxyl, substituted amino group or —$(CH_2)_n Z$ group;
$R^3$, wherein X=NH, is hydrogen, optionally substituted $C_1$-$C_3$alkyl, substituted hydroxyl, optionally mono- or disubstituted amino group or saturated 6-membered azaheterocyclyl containing an additional heteroatom selected from nitrogen or oxygen; pyridyl, alkoxycarbonyl, carboxyl or amide group; or
$R^3$, wherein X=S, SO, is hydrogen, optionally substituted $C_1$-$C_3$alkyl, substituted hydroxyl, pyridyl, alkoxycarbonyl, carboxyl or amide group; or
$R^1$ and $R^3$ independently are different substituents selected from $C_1$-$C_3$alkyl, or —$(CH_2)_n Z$ group, and $R^2$ is hydrogen, halogen, optionally substituted $C_1$-$C_3$alkyl, substituted hydroxyl;

$R^4$ is $C_1$-$C_3$alkyl;
$R^5$ is hydrogen, one or two halogens, $C_1$-$C_3$alkyl or optionally substituted hydroxyl; n is 0, 1, 2 or 3;
Z, wherein X=NH, is carboxyl COOH, $C_1$-$C_3$alkyloxycarbonyl substituted amide group $CONR^{10}R^{11}$ or amino group $NR^{10}R^{11}$; $R_{10}$ and $R_{11}$ are optionally identical hydrogen, optionally substituted $C_1$-$C_3$alkyl, $C_3$-$C_7$cycloalkyl or optionally substituted 5-7-membered azaheterocyclyl containing 1-2 nitrogen atoms in the cycle, wherein the substituents are selected from $C_1$-$C_3$alkyl; or $R_{10}$ and $R_{11}$ together with the nitrogen atom to which they are attached form an optionally substituted 5-6-membered azaheterocyclyl containing 1-2 nitrogen atoms in the cycle, wherein the substituent is selected from $C_1$-$C_3$alkyl; or
Z, wherein X=S, SO, is carboxyl COOH, $C_1$-$C_3$alkyloxycarbonyl substituted amide group $CONR^{10}R^{11}$ or amino group $NR^{10}R^{11}$; $R_{10}$ and $R_{11}$ are optionally identical hydrogen, optionally substituted $C_1$-$C_5$alkyl; or $R_{10}$ and $R_{11}$ together with the nitrogen atom to which they are attached form an optionally substituted 6-membered azaheterocyclyl containing 1-2 nitrogen atoms in the cycle, wherein the substituent is selected $C_1$-$C_3$alkyl;
with the exception of the compounds wherein X=S, $R^3$ is —$(CH_2)_n Z$ group, wherein Z is amino group $NR^{10}R^{11}$ and n=0.

2. The compound of claim 1 of the general formulas 1.1, 1.2, or a pharmaceutically acceptable salt thereof,

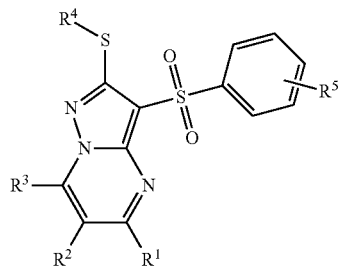

1.1

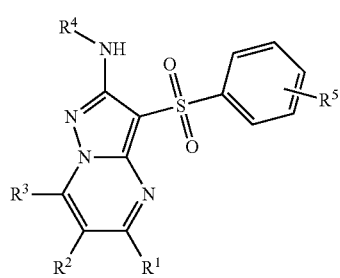

1.2 wherein: $R^1$, $R^2$, $R^3$, $R^4$ and $R^5$ have the above meanings.

3. The compound of claim 2, selected from substituted 3-arylsulfonyl-pyrazolo[1,5-a]pyrimidine s of the general formulas 1.1.1, 1.1.2, 1.1.3, 1.1.4, 1.1.5, 1.1.6, 1.1.7, 1.1.8, 1.1.9, 1.1.10, 1.2.1, 1.2.2, 1.2.3, 1.2.4, 1.2.5, 1.2.6, 1.2.7, 1.2.8, 1.2.9, 1.2.10, or a pharmaceutically acceptable salt thereof,

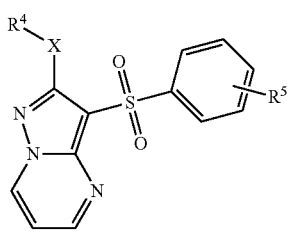
1.1.1, 1.2.1
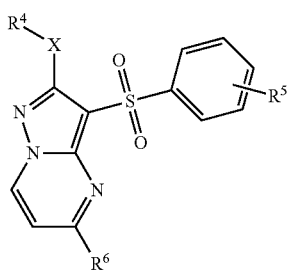
1.1.2, 1.2.2
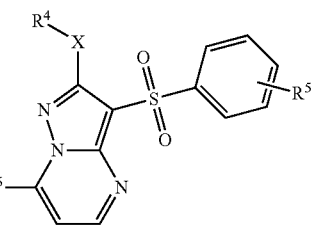
1.1.3, 1.2.3
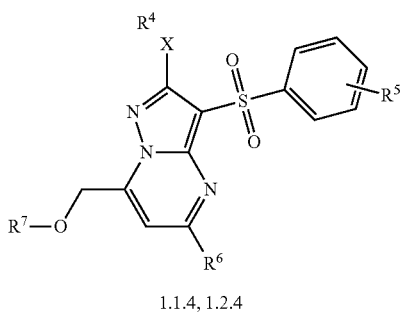
1.1.4, 1.2.4
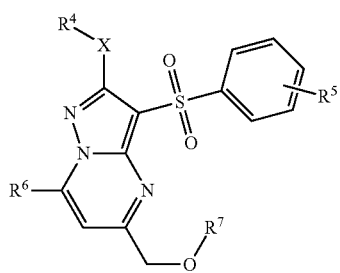
1.1.5, 1.2.5
-continued
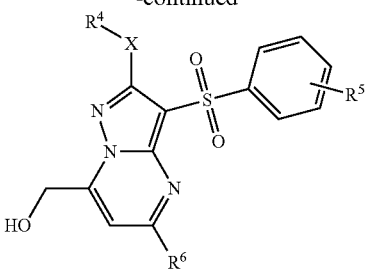
1.1.6, 1.2.6
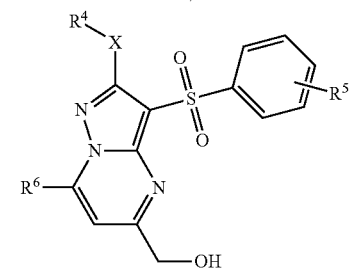
1.1.7, 1.2.7
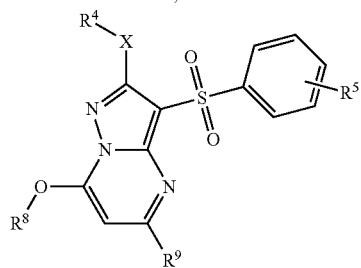
1.1.8, 1.2.8
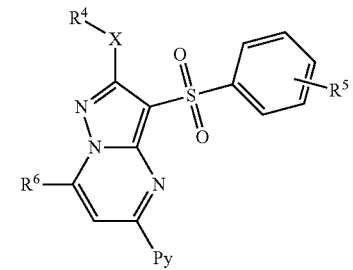
1.1.9, 1.2.9
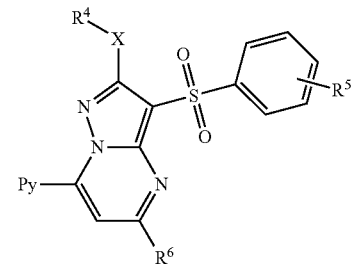
1.1.10, 1.2.10
wherein: $R^4$ and $R^5$ have the above meanings;
$R^6$ is hydrogen or $C_1$-$C_3$alkyl;
$R^7$ is hydrogen;
$R^8$ is a substituent of hydroxyl group;
$R^9$ is $C_1$-$C_3$alkyl or pyridyl;
Py is pyridyl;

X=S for the compounds of the general formulas 1.1.1, 1.1.2, 1.1.3, 1.1.4, 1.1.5, 1.1.6, 1.1.7, 1.1.8, 1.1.9, 1.1.10;

X=NH for the compounds of the general formulas 1.2.1, 1.2.2, 1.2.3, 1.2.4, 1.2.5, 1.2.6, 1.2.7, 1.2.8, 1.2.9, 1.2.10.

4. The compound of claim 3, selected from the group, consisting of 7-(hydroxymethyl)-5-methyl-2-methylsulfanyl-3-phenylsulfonyl-pyrazolo[1,5-a]pyrimidine 1.1.6(1), 7-(hydroxymethyl)-5-methyl-2-methylsulfanyl-3-(4-fluorophenylsulfonyl)-pyrazolo[1,5-a]pyrimidine 1.1.6(2), 7-(hydroxymethyl)-5-methyl-2-methylsulfanyl-3-(3-fluorophenylsulfonyl)-pyrazolo[1,5-a]pyrimidine 1.1.6(3), 7-(hydroxymethyl)-5-methyl-2-methylsulfanyl-3-(3-chlorophenylsulfonyl)-pyrazolo[1,5-a]pyrimidine 1.1.6(4), 7-(hydroxymethyl)-5-methyl-2-methylsulfanyl-3-(4-fluoro-3-chlorophenylsulfonyl)-pyrazolo[1,5-a]pyrimidine 1.1.6(5), 5-(hydroxymethyl)-7-methyl-2-methylsulfanyl-3-phenylsulfonyl-pyrazolo[1,5-a]pyrimidine 1.1.7(1), 5-(hydroxymethyl)-7-methyl-2-methylsulfanyl-3-(4-fluorophenylsulfonyl)-pyrazolo[1,5-a]pyrimidine 1.1.7(2), 5-(hydroxymethyl)-7-methyl-2-methylsulfanyl-3-(3-fluorophenylsulfonyl)-pyrazolo[1,5-a]pyrimidine 1.1.7(3), 5-(hydroxymethyl)-7-methyl-2-methylsulfanyl-3-(3-chlorophenylsulfonyl)-pyrazolo[1,5-a]pyrimidine 1.1.7(4), 5-(hydroxymethyl)-7-methyl-2-methylsulfanyl-3-(4-fluoro-3-chlorophenylsulfonyl)-pyrazolo[1,5-a]pyrimidine 1.1.7(5), 7-(hydroxymethyl)-5-methyl-2-methylamino-3-phenylsulfonyl-pyrazolo[1,5-a]pyrimidine 1.2.6(1), 7-(hydroxymethyl)-5-methyl-2-methylamino-3-(4-fluorophenylsulfonyl)-pyrazolo[1,5-a]pyrimidine 1.2.6(2), 7-(hydroxymethyl)-5-methyl-2-methylamino-3-(3-fluorophenylsulfonyl)-pyrazolo[1,5-a]pyrimidine 1.2.6(3), 7-(hydroxymethyl)-5-methyl-2-methylamino-3-(3-chlorophenylsulfonyl)-pyrazolo[1,5-a]pyrimidine 1.2.6(4), 7-(hydroxymethyl)-5-methyl-2-methylamino-3-(4-fluoro-3-chlorophenylsulfonyl)-pyrazolo[1,5-a]pyrimidine 1.2.6(5), 5-(hydroxymethyl)-7-methyl-2-methylamino-3-phenylsulfonyl-pyrazolo[1,5-a]pyrimidine 1.2.7(1), 5-(hydroxymethyl)-7-methyl-2-methylamino-3-(4-fluorophenylsulfonyl)-pyrazolo[1,5-a]pyrimidine 1.2.7(2), 5-(hydroxymethyl)-7-methyl-2-methylamino-3-(3-fluorophenylsulfonyl)-pyrazolo[1,5-a]pyrimidine 1.2.7(3), 5-(hydroxymethyl)-7-methyl-2-methylamino-3-(3-chlorophenylsulfonyl)-pyrazolo[1,5-a]pyrimidine 1.2.7(4) and 5-(hydroxymethyl)-7-methyl-2-methylamino-3-(4-fluoro-3-chlorophenylsulfonyl)-pyrazolo[1,5-a]pyrimidine 1.2.7(5), or a pharmaceutically acceptable salt thereof.

5. The compound of claim 2 selected from substituted 3-arylsulfonyl-pyrazolo[1,5-a]pyrimidines of the general formulas 1.1.11, 1.1.12, 1.1.13, 1.1.14, 1.1.15, 1.1.16, 1.1.17, 1.1.18, 1.1.19, 1.2.13, 1.2.14, 1.2.15, 1.2.16, 1.2.17, 1.2.18, 1.2.19, 1.2.20, and 1.2.21, or a pharmaceutically acceptable salt thereof,

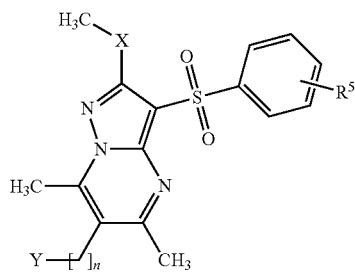

1.1.11, 1.1.14, 1.1.17, 1.2.13, 1.2.16, 1.2.19

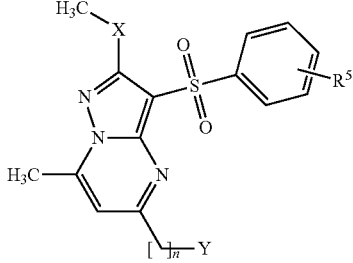

1.1.12, 1.1.15, 1.1.18, 1.2.14, 1.2.17, 1.2.20

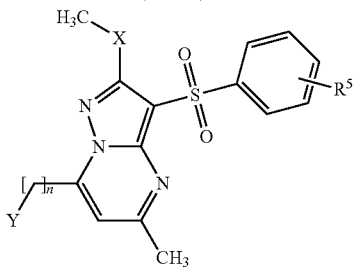

1.1.13, 1.3.16, 1.1.19, 1.2.15, 1.2.18, 1.2.21 wherein: n=0, 1, 2;

$R^5$ have the above meanings;

X=S for the compounds of the general formulas 1.1.11, 1.1.12, 1.1.13, 1.1.14, 1.1.15, 1.1.16, 1.1.17, 1.1.18, 1.1.19;

X=NH for the compounds of the general formulas 1.2.13, 1.2.14, 1.2.15, 1.2.16, 1.2.17, 1.2.18, 1.2.19, 1.2.20, 1.2.21;

Y=$C_1$-$C_3$alkyloxycarbonyl for the compounds of the general formulas 1.1.11, 1.1.12, 1.1.13, 1.2.13, 1.2.14, 1.2.15;

Y=carboxyl for the compounds of the general formulas 1.1.14, 1.1.15, 1.1.16, 1.2.16, 1.2.17, 1.2.18;

Y=substituted amide group $CONR^{10}R^{11}$, wherein $R^{10}$ and $R^{11}$ represent hydrogen, optionally substituted $C_1$-$C_3$alkyl, or $R^{10}$ and $R^{11}$ together with the nitrogen atom they are attached to form optionally substituted azaheterocyclyl for the compounds of the general formulas 1.1.17, 1.1.18, 1.1.19, 1.2.19, 1.2.20, 1.2.21.

6. The compound of claim 2, selected from substituted 3-arylsulfonyl-pyrazolo[1,5-a]pyrimidines of the general formulas 1.1.20, 1.1.21, 1.1.22, 1.2.22, 1.2.23, and 1.2.24, or a pharmaceutically acceptable salt thereof,

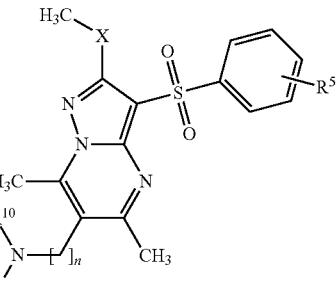

1.1.20, 1.2.22

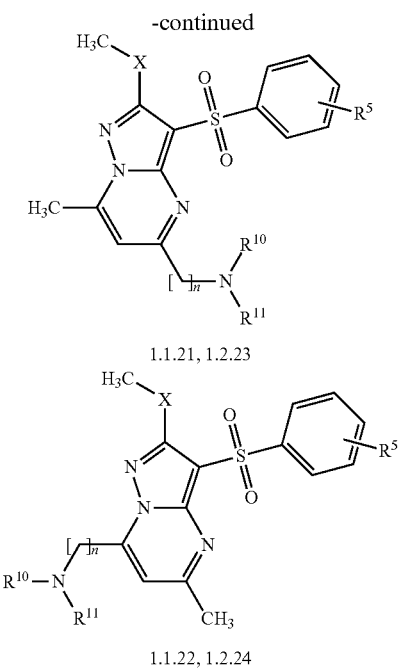

1.1.21, 1.2.23

1.1.22, 1.2.24 wherein: n is 0, 1, 2, 3, $R^5$, $R^{10}$, $R^{11}$, and also $R^{10}$ and $R^{11}$ together with the nitrogen atom they are attached to have the above meanings;

X=S for the compounds of the general formulas 1.1.20, 1.1.21, 1.1.22;

X=NH for the compounds of the general formulas 1.2.22, 1.2.23, 1.2.24.

7. The compound of claim 6 selected from the group, consisting of 6-amino-5,7-dimethyl-2-methylsulfanyl-3-phenylsulfonyl-pyrazolo[1,5-a]pyrimidine 1.1.20(1), 6-(aminomethyl)-5,7-dimethyl-2-methylsulfanyl-3-phenylsulfonyl-pyrazolo[1,5-a]pyrimidine 1.1.20(2), 6-(2-aminoethyl)-5,7-dimethyl-2-methylsulfanyl-3-phenylsulfonyl-pyrazolo[1,5-a]pyrimidine 1.1.20(3), 6-(3-aminopropyl)-5,7-dimethyl-2-methylsulfanyl-3-phenylsulfonyl-pyrazolo[1,5-a]pyrimidine 1.1.20(4), 6-(aminomethyl)-5,7-dimethyl-2-methylsulfanyl-3-(3-chlorophenylsulfonyl)-pyrazolo[1,5-a]pyrimidine 1.1.20(5), 6-(aminomethyl)-5,7-dimethyl-2-methylsulfanyl-3-(3-fluorophenylsulfonyl)-pyrazolo[1,5-a]pyrimidine 1.1.20(6), 6-(aminomethyl)-5,7-dimethyl-2-methylsulfanyl-3-(4-fluoro-3-chlorophenylsulfonyl)-pyrazolo[1,5-a]pyrimidine 1.1.20(7), 6-(2-aminoethyl)-5,7-dimethyl-2-methylsulfanyl-3-(3-chlorophenylsulfonyl)-pyrazolo[1,5-a]pyrimidine 1.1.20(8), 6-(2-aminoethyl)-5,7-dimethyl-2-methylsulfanyl-3-(3-fluorophenylsulfonyl)-pyrazolo[1,5-a]pyrimidine 1.1.20(9), 5,7-dimethyl-6-(dimethylaminomethyl)-2-methylsulfanyl-3-phenylsulfonyl-pyrazolo[1,5-a]pyrimidine 1.1.20(10), 5,7-dimethyl-6-(dimethylaminomethyl)-2-methylsulfanyl-3-(3-chlorophenylsulfonyl)-pyrazolo[1,5-a]pyrimidine 1.1.20(11), 5,7-dimethyl-6-(dimethylaminomethyl)-2-methylsulfanyl-3-(3-fluorophenylsulfonyl)-pyrazolo[1,5-a]pyrimidine 1.1.20(12), 5,7-dimethyl-6-(dimethylaminomethyl)-2-methylsulfanyl-3-(4-fluoro-3-chlorophenylsulfonyl)-pyrazolo[1,5-a]pyrimidine 1.1.20(13), 5,7-dimethyl-6-(2-dimethylamino)ethyl-2-methylsulfanyl-3-phenylsulfonyl-pyrazolo[1,5-a]pyrimidine 1.1.20(14), 5,7-dimethyl-6-(2-dimethylamino)ethyl-2-methylsulfanyl-3-(3-chlorophenylsulfonyl)-pyrazolo[1,5-a]pyrimidine 1.1.20(15), 5,7-dimethyl-6-(2-dimethylamino)ethyl-2-methylsulfanyl-3-(3-fluorophenylsulfonyl)-pyrazolo[1,5-a]pyrimidine 1.1.20(16), 5,7-dimethyl-6-(2-dimethylamino)ethyl-2-methylsulfanyl-3-(4-fluoro-3-chlorophenylsulfonyl)-pyrazolo[1,5-a]pyrimidine 1.1.20(17), 5-(aminomethyl)-7-methyl-2-methylsulfanyl-3-phenylsulfonyl-pyrazolo[1,5-a]pyrimidine 1.1.21(1), 5-(2-aminoethyl)-7-methyl-2-methylsulfanyl-3-phenylsulfonyl-pyrazolo[1,5-a]pyrimidine 1.1.21(2), 5-(dimethylaminomethyl)-7-methyl-2-methylsulfanyl-3-phenylsulfonyl-pyrazolo[1,5-a]pyrimidine 1.1.21(3), 5-(dimethylaminomethyl)-7-methyl-2-methylsulfanyl-3-(4-fluoro-3-chlorophenylsulfonyl)-pyrazolo[1,5-a]pyrimidine 1.1.21(4), 5-(2-dimethylaminoethyl)-7-methyl-2-methylsulfanyl-3-phenylsulfonyl-pyrazolo[1,5-a]pyrimidine 1.1.21(5), 7-(aminomethyl)-5-methyl-2-methylsulfanyl-3-phenylsulfonyl-pyrazolo[1,5-a]pyrimidine 1.1.22(1), 7-(2-aminoethyl)-5-methyl-2-methylsulfanyl-3-phenylsulfonyl-pyrazolo[1,5-a]pyrimidine 1.1.22(2), 7-(dimethylaminomethyl)-5-methyl-2-methylsulfanyl-3-phenylsulfonyl-pyrazolo[1,5-a]pyrimidine 1.1.22(3), 7-(dimethylaminomethyl)-5-methyl-2-methylsulfanyl-3-(4-fluoro-3-chlorophenylsulfonyl)-pyrazolo[1,5-a]pyrimidine 1.1.22(4), 7-(2-dimethylaminoethyl)-5-methyl-2-methylsulfanyl-3-phenylsulfonyl-pyrazolo[1,5-a]pyrimidine 1.1.22(5), 6-amino-5,7-dimethyl-2-methylamino-3-phenylsulfonyl-pyrazolo[1,5-a]pyrimidine 1.2.22(1), 6-(aminomethyl)-5,7-dimethyl-2-methylamino-3-phenylsulfonyl-pyrazolo[1,5-a]pyrimidine 1.2.22(2), 6-(2-aminoethyl)-5,7-dimethyl-2-methylamino-3-phenylsulfonyl-pyrazolo[1,5-a]pyrimidine 1.2.22(3), 6-(3-aminopropyl)-5,7-dimethyl-2-methylamino-3-phenylsulfonyl-pyrazolo[1,5-a]pyrimidine 1.2.22(4), 6-(aminomethyl)-5,7-dimethyl-2-methylamino-3-(3-chlorophenylsulfonyl)-pyrazolo[1,5-a]pyrimidine 1.2.22(5), 6-(aminomethyl)-5,7-dimethyl-2-methylamino-3-(3-fluorophenylsulfonyl)-pyrazolo[1,5-a]pyrimidine 1.2.22(6), 6-(aminomethyl)-5,7-dimethyl-2-methylamino-3-(4-fluoro-3-chlorophenylsulfonyl)-pyrazolo[1,5-a]pyrimidine 1.2.22(7), 6-(2-aminoethyl)-5,7-dimethyl-2-methylamino-3-(3-chlorophenylsulfonyl)-pyrazolo[1,5-a]pyrimidine 1.2.22(8), 6-(2-aminoethyl)-5,7-dimethyl-2-methylamino-3-(3-fluorophenylsulfonyl)-pyrazolo[1,5-a]pyrimidine 1.2.22(9), 5,7-dimethyl-6-(dimethylaminomethyl)-2-methylamino-3-phenylsulfonyl-pyrazolo[1,5-a]pyrimidine 1.2.22(10), 5,7-dimethyl-6-(dimethylaminomethyl)-2-methylamino-3-(3-chlorophenylsulfonyl)-pyrazolo[1,5-a]pyrimidine 1.2.22(11), 5,7-dimethyl-6-(dimethylaminomethyl)-2-methylamino-3-(3-fluorophenylsulfonyl)-pyrazolo[1,5-a]pyrimidine 1.2.22(12), 5,7-dimethyl-6-(dimethylaminomethyl)-2-methylamino-3-(4-fluoro-3-chlorophenylsulfonyl)-pyrazolo[1,5-a]pyrimidine 1.2.22(13), 5,7-dimethyl-6-(2-dimethylamino)ethyl-2-methylamino-3-phenylsulfonyl-pyrazolo[1,5-a]pyrimidine 1.2.22(14), 5,7-dimethyl-6-(2-dimethylamino)ethyl-2-methylamino-(3-chlorophenylsulfonyl)-pyrazolo[1,5-a]pyrimidine 1.2.22(15), 5,7-dimethyl-6-(2-dimethylamino)ethyl-2-methylamino-3-(3-fluorophenylsulfonyl)-pyrazolo[1,5-a]pyrimidine 1.2.22(16), and 5,7-dimethyl-6- (2-dimethylamino)ethyl-2-methylamino-3-(4-fluoro-3-chlorophenylsulfonyl)-pyrazolo[1,5-a]pyrimidine 1.2.22(17), or a pharmaceutically acceptable salt thereof.

8. A pharmaceutical composition for treating a disease of central nervous system in human or warm blooded animal, pathogenesis of which is associated with 5-$HT_6$ receptors, comprising a pharmaceutically effective amount of a compound of the general formula 1, or a pharmaceutically acceptable salt thereof according to claim 1 and pharmaceutically acceptable carriers, inert excipients or solvents.

9. The pharmaceutical composition according to claim 8 in the form of tablets, capsules, or injections placed in pharmaceutically acceptable packing.

10. A method for the preparation of a compound of the general formula 1, or a pharmaceutically acceptable salt thereof by mixing a compound of formula 2 with a compound of formula 3 and subsequently isolating the reaction products,

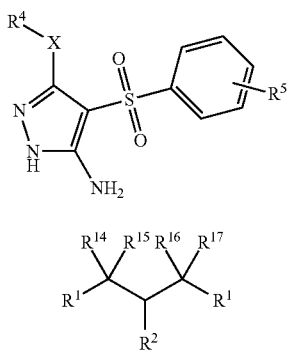

wherein: $R^1$, $R^2$, $R^3$, $R^4$ and $R^5$ have the above meanings;
X=S or NH;
$R^{14}$ and $R^{15}$, $R^{16}$ and $R^{17}$ independently of each other together with the carbon atoms they are attached to form carbonyl group, or $R^1$, $R^{14}$ and $R^{15}$, and $R^3$, $R^{16}$ and $R^{17}$ together with the carbon atoms they are attached to independently of each other form acetal group.

11. A method for the preparation of a compound of the general formula 1.1 wherein X=SO, by oxidizing a compound of the general formula 1.1 wherein X=S.

12. A method for the preparation of a compound of formula 1.1.6, 1.2.6, 1.1.7, 1.2.7 by acting a boron tribromide on a compound of the general formulas 1.1.4, 1.2.4, 1.1.5, 1.2.5, respectively.

13. A method for the preparation of a compound of formula 1.1.20, 1.2.22, or a pharmaceutically acceptable salt thereof, in which n=0 and $R^{10}$=$R^{11}$=H, by hydrogenating a compound of the general formula 1 wherein $R^2$=aryldiazenyl, or by hydrolyzing a compound of the general formula 1 wherein $R^2$=acylamino group.

* * * * *